(12) United States Patent
Farah

(10) Patent No.: US 12,029,896 B2
(45) Date of Patent: Jul. 9, 2024

(54) THREAD BIDIRECTIONAL INTERLOCKING OF ELECTRODE LEAD

(71) Applicant: Senso Medical Labs, Ltd., Nazareth (IL)

(72) Inventor: Maroun Farah, Nazareth (IL)

(73) Assignee: Senso Medical Labs Ltd., Nazareth (IL)

( * ) Notice: Subject to any disclaimer, the term of this patent is extended or adjusted under 35 U.S.C. 154(b) by 1079 days.

(21) Appl. No.: 16/300,361

(22) PCT Filed: May 11, 2017

(86) PCT No.: PCT/IL2017/050528
§ 371 (c)(1),
(2) Date: Nov. 9, 2018

(87) PCT Pub. No.: WO2017/195209
PCT Pub. Date: Nov. 16, 2017

(65) Prior Publication Data
US 2019/0160279 A1    May 30, 2019

Related U.S. Application Data

(60) Provisional application No. 62/334,687, filed on May 11, 2016.

(51) Int. Cl.
*A61N 1/05*   (2006.01)
*A61N 1/04*   (2006.01)
(Continued)

(52) U.S. Cl.
CPC ......... *A61N 1/0551* (2013.01); *A61N 1/0472* (2013.01); *D03D 1/0088* (2013.01); *D03D 15/00* (2013.01); *D03D 25/005* (2013.01); *A61B 2562/0209* (2013.01); *A61B 2562/125* (2013.01); *A61N 1/05* (2013.01); *D03D 41/004* (2013.01); *D04C 1/02* (2013.01); *D10B 2401/16* (2013.01); *D10B 2509/00* (2013.01)

(58) Field of Classification Search
CPC ...... A61N 1/05; A61N 1/0551; A61N 1/0472; D03D 1/0088; D03D 15/00; D03D 25/00; D03D 25/005; D10B 2509/00
See application file for complete search history.

(56) References Cited

U.S. PATENT DOCUMENTS 5,311,866 A   5/1994 Kagan et al.
5,330,524 A   7/1994 Mar
(Continued)

FOREIGN PATENT DOCUMENTS

CA   2447239 C   10/2010
CA   2751569 C   3/2015
(Continued)

OTHER PUBLICATIONS

"Integral." Merriam-Webster.com. [https://www.merriam-webster.com/dictionary/integral] 2022. (Oct. 5, 2022) (Year: 2022).*
(Continued)

*Primary Examiner* — Pamela M. Bays

(57) ABSTRACT

The present invention provides interlocked thread electrode leads, methods of fabrication thereof, and thread interlocking machines.

11 Claims, 38 Drawing Sheets

(51) Int. Cl.
  *D03D 1/00*   (2006.01)
  *D03D 15/00*  (2021.01)
  *D03D 25/00*  (2006.01)
  *D03D 41/00*  (2006.01)
  *D04C 1/02*   (2006.01)

(56) References Cited

U.S. PATENT DOCUMENTS

| | | | |
|---|---|---|---|
| 5,569,883 A * | 10/1996 | Walter | A61N 1/056 |
| | | | 607/125 |
| 7,097,451 B2 | 8/2006 | Tang | |
| 7,470,483 B2 | 12/2008 | Yoshida et al. | |
| 7,651,506 B2 | 1/2010 | Bova et al. | |
| 7,835,778 B2 | 11/2010 | Foley et al. | |
| 8,923,984 B2 | 12/2014 | Parker et al. | |
| 10,085,784 B2 | 10/2018 | Ono et al. | |
| 2004/0131920 A1 | 7/2004 | Yoshida et al. | |
| 2007/0106357 A1 | 5/2007 | Denker et al. | |
| 2008/0161893 A1* | 7/2008 | Paul | A61N 1/05 |
| | | | 607/116 |
| 2008/0166681 A1 | 7/2008 | Weinstein et al. | |
| 2008/0196783 A1 | 8/2008 | Van Bruggen et al. | |
| 2010/0070008 A1 | 3/2010 | Parker et al. | |
| 2010/0121421 A1* | 5/2010 | Duncan | A61N 1/05 |
| | | | 607/116 |
| 2012/0232629 A1 | 9/2012 | Bloemer et al. | |
| 2014/0031911 A1* | 1/2014 | Williams | A61N 1/05 |
| | | | 156/51 |
| 2014/0288577 A1 | 9/2014 | Robinson et al. | |
| 2014/0324143 A1 | 10/2014 | Robinson et al. | |
| 2015/0297135 A1* | 10/2015 | Shoshani | A41D 13/1281 |
| | | | 66/202 |

FOREIGN PATENT DOCUMENTS

| | | |
|---|---|---|
| CN | 103157181 A | 6/2013 |
| CN | 103230302 A | 8/2013 |
| DE | 102008040773 A1 | 2/2010 |
| EP | 1094760 A1 | 5/2001 |
| EP | 1094760 B1 | 3/2006 |
| EP | 1731643 A1 | 12/2006 |
| JP | 2000-221 A | 1/2000 |
| JP | 2008542565 A | 11/2008 |
| JP | 2011-15818 A | 1/2011 |
| JP | 5487496 B2 | 5/2014 |
| WO | 2008/048237 A2 | 4/2008 |
| WO | 2010/033370 A2 | 3/2010 |
| WO | 2010/117381 A1 | 10/2010 |
| WO | 2013/075171 A1 | 5/2013 |
| WO | 2013075178 A1 | 5/2013 |
| WO | 2014176118 A1 | 10/2014 |

OTHER PUBLICATIONS

International Search report for PCT/IL2017/050528 dated Sep. 26, 2017 (PCT/ISA/210).
Written Opinion of the International Searching Authority for PCT/IL2017/050528 dated Sep. 26, 2017 (PCT/ISA/237).

* cited by examiner

THREAD BIDIRECTIONAL INTERLOCKING OF ELECTRODE LEAD

FIELD OF THE INVENTION

The present invention relates to the fields of thread interlocking and electrodes produced thereby.

BACKGROUND

Electrical stimulation of bodily parts such as spinal cord, peripheral nerves, cranial nerves, nerve roots, muscles, or brain tissues is used to treat various conditions including, e.g., Parkinson's disease, dystonia, chronic pain, Huntington's disease, bradykinesia, epilepsy and seizures, eating disorders, and mood disorders. For those conditions as well as others, sensing and/or recording electrodes may be utilized for monitoring the electrical activity of the tissues to be treated or studied and commonly to provide a stimulating electric signal to target regions/structures for treatment. Many of the electrodes, whether stimulating or sensing, have similar characteristics.

The electrode leads are commonly implanted in a specific region for providing the treatment and/or monitoring functions, and multiple features and characteristics are desired to exist in the electrode leads for providing proper functionality while mitigating the risk for undesired effects. Some of the desired features and characteristics include small lead size, a multiplicity of small contacts, directionality of sensing and stimulation, structural rigidity and flexibility, cost of manufacturing and others. However, some tradeoffs are commonly made in the electrode leads between the features and characteristics due to general constraints inherent to common physical structure of the leads.

There is therefore a need in the art for electrode lead structures for enabling better tradeoffs to facilitate enhanced features and characteristics.

There are various thread interlocking techniques that are utilized to achieve different biological tissue properties and structures. The most common techniques include breading, weaving, and knitting. In knitting, a yarn is manipulated to be interlocked with itself at various points by creating loops called stiches arranged in a line or tube. The loops are created by manipulating the yarn using needles, and the dimensions of the knitted structure are affected by the dimensions of the needles and the thread (yarn). In breading, multiple threads are interlocked together in an axial progression to create an elongated structure, and the dimension of the threads and their number determines the length of axial progression, and this technique is commonly utilized for manufacturing of ropes and cables. In weaving, two distinct sets of threads are interlocked to form the structure: a first set of threads called warps—vertical threads that are generally aligned linearly; and a second set of threads called weft(s), which includes a thread that is manipulated horizontally to pass between the warps. In weaving, each pass of the weft between the warps forms a beat, and in each beat, the warps are arranged such that the weft would pass either in front or behind a warp, thereby forming desired textile patterns.

Some structures and devices, such as multi-contact electrodes, may benefit from being assembled using thread interlocking techniques, but the amount of threads involved in the process and/or the interlocking procedure itself render these techniques ineffective. Accordingly, the present invention provides methods and devices capable of using large amount of threads as needed, for fabricating any size of structure as needed, while using threads as desired diameters and materials as required in each case.

SUMMARY OF THE INVENTION

The present invention provides electrode leads that are made of a plurality of interlocked filaments having a conductive core coated with a nonconductive coating. The exposed conductive core of the filaments forms at least one 3D distinct conductive mass at the distal end of the electrode, whereas a portion of the filaments with the exposed conductive core are disposed on the circumferential surface of the electrode. This easy fabricated structure enables controlling the size and positioning of the very small contacts on the electrode lead.

The present invention further provides methods for fabricating such electrode leads by interlocking a plurality of filaments, e.g. braiding, knitting, weaving, interwinding, entangling, meshing, or any other method by which the filaments are interlocked or a combination thereof. The structures of the electrodes and electrode leads are unique and render them with improved characteristics such as increased charge capacity, improved directionality, larger contact surface area.

The present invention further provides electrode leads having volume sharing for a plurality of contacts by which directionality and functionality of the contacts can be varied according to need.

In an alternative aspect, the electrodes of the present invention can be used as measurement tools for determining the place or distance from a reference point on the electrode lead based on spacing that is predetermined or known. Using this measurement tool can also measure the distance between the layers in a certain cross section, the diameter of a cross section, or the distance of a point in the cross section related to the reference point in the same cross section. In this way, the width and thickness dimensions of the electrode lead or areas within it can be measured.

In certain embodiments, certain materials can be incorporated/deposited within the electrode lead during fabrication, and may be manipulated/modified after fabrication for achieving a desired functionality and/or structural property, such as: local electric/thermal isolation, forming a medium having desired function, etc.

In certain embodiments, the electrodes of the invention further comprise connectors in which electrical connection terminals are provided.

According to other embodiments, the present invention provides devices, systems and methods for thread interlocking, wherein threads within interlocked thread structures have both vertical portions and horizontal portions, such that a horizontal portion of a thread is configured to pass between vertical portions of other threads and lock therewith. Advantageously, having threads changing orientation from vertical to horizontal within the thread interlocked structure may facilitate generation of accurate structures while utilizing a relatively low amount of threads.

In one aspect, the present invention provides an interlocked thread structure, comprising: (a) a proximal end and a distal end, with a progression axis from the proximal end to the distal end; and (b) a plurality of threads aligned vertically, in parallel to the progression axis, at said proximal end, structured to each have horizontal portions, perpendicular to the progression axis, and vertical portions, parallel to the progression axis, such that a horizontal portion of one thread is configured to pass between vertical portions of other threads, thereby interlocking therewith, wherein a horizontal portion of one or more threads passing between vertical portions of other threads is a beat, and each beat determines a vertical distance along the progression axis between said proximal end and said distal end.

In a specific aspect, the present invention provides an interlocked thread electrode, comprising: (a) a proximal end and a distal end, with a progression axis from the proximal end to the distal end; and (b) a plurality of threads aligned vertically, in parallel to the progression axis, at said proximal end, structured to each have horizontal portions, perpendicular to the progression axis, and vertical portions, parallel to the progression axis, such that a horizontal portion of one thread is configured to pass between vertical portions of other threads, thereby interlocking therewith, wherein a horizontal portion of one or more threads passing between vertical portions of other threads is a beat, and each beat determines a vertical distance along the progression axis between said proximal end and said distal end, wherein at least one of said plurality of threads comprises an electrically conductive filament coated with an electrically isolative layer, and the electrically conductive filament is exposed at predetermined locations for achieving a contact thereat.

In another aspect, the present invention provides a thread interlocking machine for fabricating an interlocked thread electrode, comprising: (a) a plurality of thread carriers, each configured to hold a desired thread, at least one thereof having a conductive core coated with a non-conductive material; (b) at least two cross-track segments, each segment having: (i) a vertical track, defining a vertical movement range of a thread-carrier, and (ii) a horizontal track, defining a horizontal movement range of a thread-carrier (shuttle), such that said vertical track and said horizontal track intersect along the longitude thereof, facilitating an alteration of movement of a thread-carrier between said vertical track and said horizontal track, and the cross-track segments are arranged horizontally to facilitate a movement of a thread carrier from a horizontal track of one cross-track segment to a horizontal track of another segment; (c) a thread base, configured to hold a plurality of threads at a distal end thereof, such that the threads are strained from said thread carriers to said thread base; (d) at least one actuator for moving said plurality of thread carriers and optionally said thread base; (e) at least one means (laser) for exposing said conductive core of said filament(s); and (f) a control unit.

In yet another aspect, the present invention provides a method for fabricating a thread interlocked electrode using the thread interlocking machine of the invention, comprising the steps of: (a) inputting a desired architecture of an electrode to be fabricated; (b) optionally, compiling the desired electrode structure into interlocked digital structure and then into a machine code used to control the interlocking machine; (c) arranging a plurality of thread carriers at vertical tracks of segments of the thread interlocking machine according to the desired architecture; (d) selecting a carrier to function as a weft; (e) moving the weft along the horizontal track to pass between other filaments acting as the warps; (f) optionally, selecting a different thread carrier to function as a weft and switching therebetween; (g) continue moving the selected weft along the horizontal track to pass between the warps; (h) pressing the weft(s) towards the base to define a beat; and (i) terminating the process when the electrode is ready. The above method may further comprise at least one of the following steps: functionalizing at least a portion of the weft, e.g. by removing the coating material to expose the internal conductive material of the thread to create a contact; and terminating a thread when it is no longer needed in the electrode.

In addition to the exemplary aspects and embodiments described above, further aspects and embodiments will become apparent by reference to the figures and by study of the following detailed descriptions.

BRIEF DESCRIPTION OF THE DRAWINGS

FIGS. 11a-11e illustrate electrode leads with markings thereto according to some embodiments.

FIG. 15a illustrates an electrode fabricated from a single thread that splits into several filaments; and FIGS. 15b-15e illustrate an electrode fabricated from a bundle of filaments;

FIG. 17c illustrates a planar electrode lead in accordance with one exemplary embodiment;

FIG. 24a machine with a lowered base; and FIG. 24b machine with a centered base, according to some embodiments;

DETAILED DESCRIPTION

Figure 1:
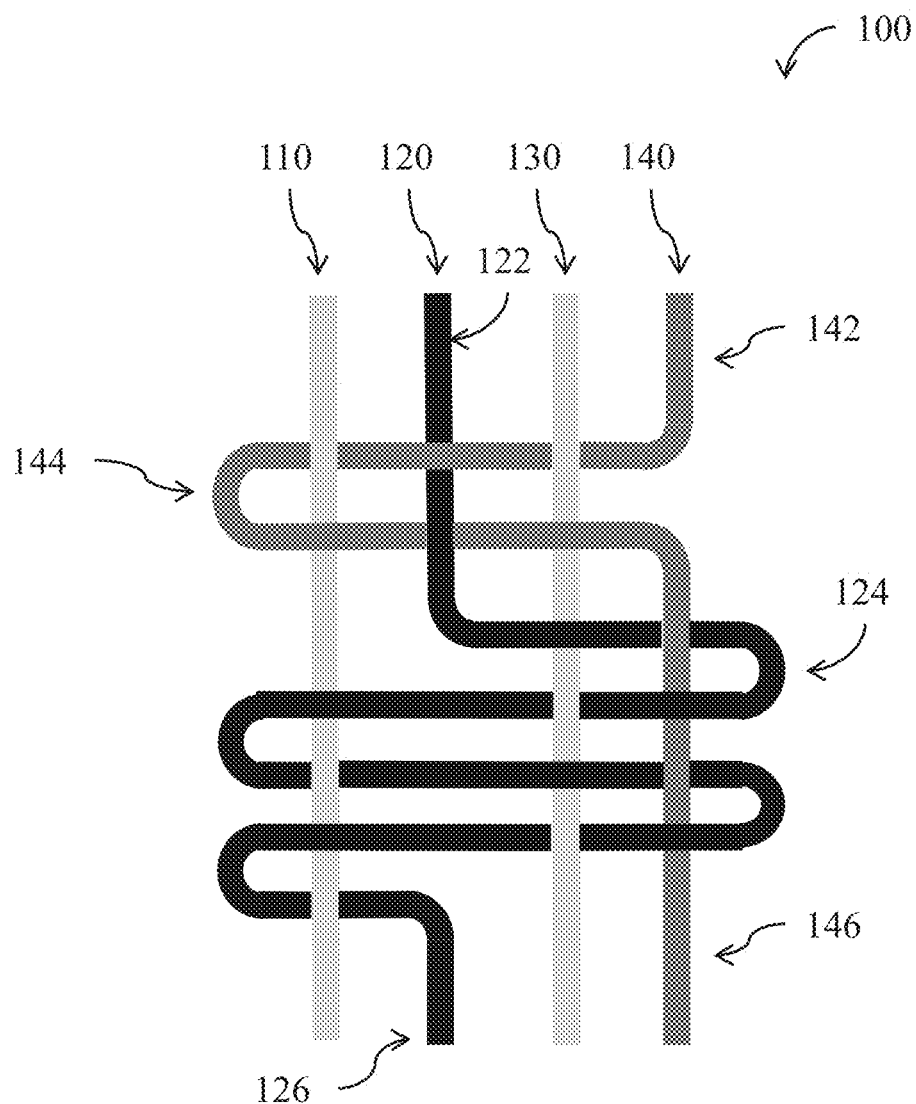
FIG. 1 schematically illustrates an interlocked thread structure of an exemplary electrode lead of the invention.

According to aspects and embodiments of the present invention, leads for electrodes are provided. The embodiments are aimed at construction of leads, which can be custom made, of a plurality of filaments interlocked to form a lead provided with electrodes having contacts in the distal side of the lead. The interlocked filaments can be fabricated using methods such as braiding, knitting, weaving, interwinding, entangling, meshing, or any other method by which the filaments are interlocked or a combination thereof. Any other method by which filaments can be interlocked into a structure of a lead is covered by the scope of the present invention. The electrode is a part of the electrode lead that has a conductive portion that is electrically connected to an electronic module.

According to one aspect of the embodiments disclosed herein, an electrode lead with at least one electrode having a contact surface area that act as an electrically active surface is provided, wherein the electrode occupies a volume associated with the electrode lead's distal portion. The volume the electrode occupies can be either mostly hidden within the volume of the lead in a cavity, hollow, chamber, or a pocket; the electrode can have a contact flush or semi-flush with an outer surface of the lead; or the volume of the electrode can protrude, project, or extend from the outer surface of the electrode lead; or a combination thereof.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

Interlocking threads together to form a structure is used in a wide variety of fields for achieving different characteristics. Examples of such structures include textile, electric wires, ropes, strings/strands and more, and the way the threads are interlocked provides the unique properties, as well as limitation of manufacture.

Common means of thread interlocking include weaving, breading and knitting, with a unique advantage of weaving in terms of special selectivity and resolution, enabling creation of exact patterns in textile, as the distance between warps is determined by the thickness thereof and the weft passing therebetween, and the distance between beats is known and determined by the thickness of the weft(s). The beat is further defined by many other different factors, such as the tension of the threads/yarns, the warp bending over the weft yarns, etc. Accordingly, in certain embodiments, the determination of the weaving structural pattern is carried out by any of the above mentioned mechanisms. This finesse of distance determination and resolution can reach up to microns or even less.

Meanwhile, industries other than textile, rely on various techniques to achieve spatial resolution: some expensive, and include, e.g., photo-lithography and micro fabrication, and others cheaper but with limited resolution and finesse.

One such field is electrodes, specifically invasive multi-contact electrodes, where the exact location and dimensions of electric contacts is of very high importance, the number of desired contacts is high (tens or hundreds), and the electrode is usually a thin elongated structure, enabling hosting a limited amount of electric wires or support structures to deliver the desired functionality while keeping mechanical properties above a desired threshold.

Accordingly, the present invention provides devices, systems, and methods for manufacturing electrodes, wherein the structure of the electrode is made of interlocked threads, the threads having vertical parts (portions), progressing along the elongation of the electrode, and horizontal parts passing between vertical portions of other threads to interlock therewith, and define a beat. The present invention further provides electrodes produced by the devices, systems, and methods of the invention.

Advantageously, having the threads change directionality from vertical to horizontal, enables providing the vertical support structure to function as additional delivery channels for passing the threads (electric wires) to their desired active location, while providing electric contact, thereby enabling the use of multiple electric wires for multiple electric contact. According to some embodiments, the electric contacts are created by uncovering an isolative medium on the electric wires at desired locations. Accordingly, the methods, devices and systems of the invention facilitate production of electrodes having the threads function both as a support (structure) of the electrode, as well as electric conductivity path for reaching the target electric contacts.

It should be noted that the term "vertical" as used herein and throughout the application refers also to interlocking with horizontal threads.

According to some embodiments, upon reaching a determined contact location, the associated electric wire is selected to change interlocking orientation to create a contact at a desired shape and size in the depth of the electrode structure.

In certain embodiments, the provided structure facilitated accurate determination and/or contact location, and dimensions at a resolution based on the thickness of the wires. Alternatively, in certain embodiments, other methods besides thickness, e.g. vision control, structural patterns counting, etc., are used for accurate determination and/or contact location.

According to some embodiments, the interlocking technique of the invention is utilized for manufacturing various structured electrodes having different geometries as desired, e.g. planar, sheet or volumetric shapes.

According to some embodiments of the invention, the interlocked threads are configured to structure a 2-dimensional (or planar) sheet shape. According to alternative embodiments, the interlocked threads are configured to structure a 3-dimensional shape.

In certain embodiments, the electrode produced according to the invention is a part of the electrode lead that has a conductive portion that is electrically connected to an electronic module.

In certain embodiments, an electrode lead produced according to the invention comprises at least one electrode having a contact surface area that acts as an electrically active surface, wherein the electrode occupies a volume associated with the electrode lead's distal portion. The volume the electrode occupies can be either mostly hidden within the volume of the lead in a cavity, hollow, chamber, or a pocket; the electrode can have a contact flush or semi-flush with an outer surface of the lead; or the volume of the electrode can protrude, project, or extend from the outer surface of the electrode lead; or any combination thereof.

The present invention provides an interlocked thread structure, comprising: (a) a proximal end and a distal end, with a progression axis from the proximal end to the distal end; and (b) a plurality of threads aligned vertically, in parallel to the progression axis, at said proximal end, structured to each have horizontal portions, perpendicular to the progression axis, and vertical portions, parallel to the progression axis, such that a horizontal portion of one thread is configured to pass between vertical portions of other threads, thereby interlocking therewith, wherein a horizontal portion of one or more threads passing between vertical portions of other threads is a beat, and each beat determines a vertical distance along the progression axis between said proximal end and said distal end.

In certain embodiments of the interlocked thread structure of the invention, a vertical portion of a thread is a warp portion, and a horizontal portion of a thread is a weft portion, and at least some of the threads are configured to be warps at certain locations, and wefts at other locations.

In certain embodiments of the interlocked thread structure of the invention, when threads pass from being warp to being weft they form a directional contact; the whole time the thread is in weft portion it does not have to form a full wrap around the interlocked core. When a thread pass from being a warp to being a weft it can: (i) form a full circle, i.e. wrap around the entire fabricated interlocked lead or lead core (see e.g. 720 in FIG. 7a); or (ii) does not form a full circle, i.e. does not wrap around the entire fabricated interlocked lead or lead core, but rather wrap only a portion of the warp(s) at a specific area of the fabricated electrode (see e.g. dark thick lines 730 in FIG. 7b), and optionally becomes a full weft, followed by returning to be a warp (see e.g. 126 in FIG. 1).

In specific embodiments of the interlocked thread structure of the invention, the threads are arranged to form a sheet.

In specific embodiments of the interlocked thread structure of the invention, the horizontal portions of a plurality of threads pass through vertical portion of at least one other thread to form one beat.

In certain embodiments of the interlocked thread structure of the invention, the vertical portions of the threads are arranged in a non-linear form, such that a horizontal cross section of the structure forms a two-dimensional shape. In a specific embodiment, the threads are arranged to form an elongated cylindrical shape, such that the axis of the elongated tubular shape is the progression axis between said proximal end and said distal end. In an alternative specific embodiment, the threads are arranged to form an elongated shape, such that the axis of the elongated shape is the progression axis between said proximal-end and said distal-end, and a horizontal cross-section thereof comprises a plurality of vertical thread portions arranged at various radial distances. In a more specific embodiment, said horizontal cross-section comprises a plurality of vertical thread portions arranged at more than one radial distances.

In certain embodiments of the interlocked thread structure of the invention, the horizontal portions of threads and the arrangement thereof between vertical portions is determined for achieving a desired mechanical/structural/functional property.

In certain embodiments, the interlocked thread structure of the invention is an electrode, wherein at least one of said plurality of threads comprises an electrically conductive filament coated with an electrically isolative layer, and the electrically conductive filament is exposed at predetermined locations for achieving a contact thereat.

In specific embodiments, when the interlocked thread structure of the invention is an electrode, the contact is at horizontal portions of said at least one filament.

In certain embodiments of the interlocked thread electrode of the invention, the horizontal portions of a plurality of threads pass through vertical portion of other threads to form one beat.

In specific embodiments of the interlocked thread electrode of the invention, the vertical portions of the threads are arranged in a non-linear form, such that a horizontal cross section of the structure forms a two-dimensional shape, and a horizontal portion of a thread forms a planar (two-dimensional) structure at a certain beat.

In specific embodiments of the interlocked thread electrode of the invention, the electrically conductive filament of said at least one thread is exposed at predetermined locations in horizontal portions, forming a two-dimensional (planar) contact at said predetermined locations.

In other embodiments of the interlocked thread electrode of the invention, a horizontal portion of at least one thread at a plurality of beats forms a three-dimensional structure along and within the electrode.

In certain embodiments of the interlocked thread electrode of the invention, the electrically conductive filament of said at least one thread is exposed at predetermined locations in horizontal portions, forming a three-dimensional (volumetric) contact.

In yet another specific embodiment of the interlocked thread electrode of the invention, the threads form a porous structure, permissive for a flow of bodily fluids therethrough.

Reference is now made to FIG. 1 that illustrates an interlocked thread structure 100, according to some embodiments of the invention. In certain embodiments, structure 100 is made of multiple threads: first—110, second—120, third—130, and fourth-thread 140, which are interlocked together forming the structure 100. In certain embodiments, at least some of threads 110, 120, 130 and 140, include vertical portions, progressing along the longitude of structure 100, and horizontal portions progressing perpendicular to the longitude of structure 100, interlocking with vertical portions of other threads. As illustrated, second thread 120 has a first vertical portion 122, then it changes progression direction to have a horizontal portion 124, interlocking with first—110, third—130, and fourth-thread 140, then returns to vertical progression in a second vertical portion 126.

Generally, multiple threads may have horizontal portions at the same or different longitudes along structure 100. For example, fourth thread 140 begins with a vertical portion 142, then changes direction to progress with a horizontal portion 144, interlocking with vertical portions of other threads, then returning to original position to progress with a second vertical portion 146 thereof.

In certain embodiments, on each horizontal pass/progression of a horizontal portion of a thread, vertical portions of other threads are arranged in an axis perpendicular to both the horizontal progression and vertical progression directions for achieving a desired interlocking path/pattern.

In certain embodiments, at least some threads may progress along the longitude of the interlocked structure till the end thereof, while other threads may be terminated along the way and not participate further in the structure. Such a feature is advantageous when a thread reaches a contact location, and after formation of the contact, the associated thread(s) is no longer in need, and may be terminated, for various reasons, such as reducing the interlocking process complexity, reducing the diameter/cross-section area of the electrode, etc.

Figures 2, 3:
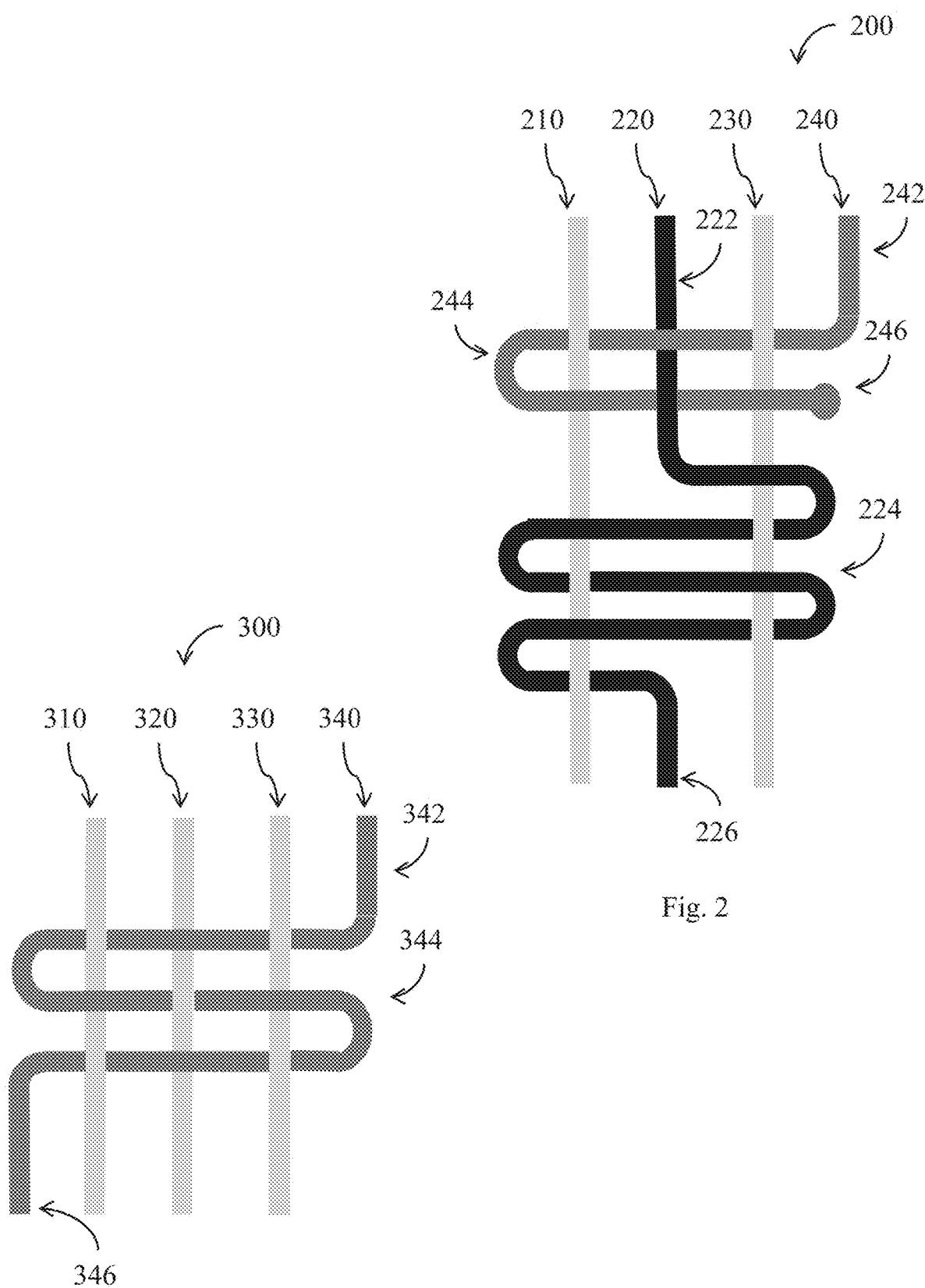
FIG. 2 schematically illustrates an interlocked thread structure with terminated threads, according to some embodiments.
FIG. 3 schematically illustrates an interlocked thread structure with vertical thread repositioning, according to one embodiment of the invention.

Reference is now made to FIG. 2, which schematically illustrates an interlocked thread structure 200 with a terminated thread, according to some embodiments. In certain embodiments, structure 200 includes multiple threads, such as first—210, second—220, third—230 and fourth-thread 240, which have vertical portions and may have horizontal portions, such as first vertical portion 222, second vertical portion 226, and horizontal portion 224 of second thread 220.

Some threads may not participate in the interlocking of structure 200 throughout the whole longitude thereof, as seen, e.g. for fourth thread 240, which has a vertical portion 242, then changes direction to interlock with vertical portions of other threads by horizontal portion 224, and is then terminated at a terminal point 246 thereof.

For achieving desired structures, such as contact shapes, or shifting of thread geometry or the like, threads may have vertical portions at a certain position, then shift to another position by changing the direction to horizontal progression, and when the new position is reached, changing the direction back to vertical progression.

Reference is now made to FIG. 3, schematically illustrating an interlocked thread structure 300 with vertical thread repositioning, according to some embodiments. In certain embodiments, structure 300 includes a first—310, a second—320, a third—330, and a fourth-thread 340, wherein fourth thread 340 begins with a vertical portion 342 at a first vertical progression position, then changes direction to form a horizontal portion 344, and then changes direction back to vertical progression 346 in a second vertical progression position.

In certain embodiments, the interlocked structure according to the invention may be a part of the whole lead, wherein multiple interlocked structures may comprise a single lead.

Generally, a horizontal pass of a horizontal portion of a thread defines a beat, which determines the progression of the interlocking based on various characteristics, such as the thickness of the threads and their plasticity. In certain embodiments, a plurality of horizontal portions of different threads may participate in defining one beat. Such a feature may be beneficial for multiple uses, e.g. for controlling/determining the shape and area of the cross section of the electrode, creating contacts that share the same longitudinal distance, etc.

Figure 4:
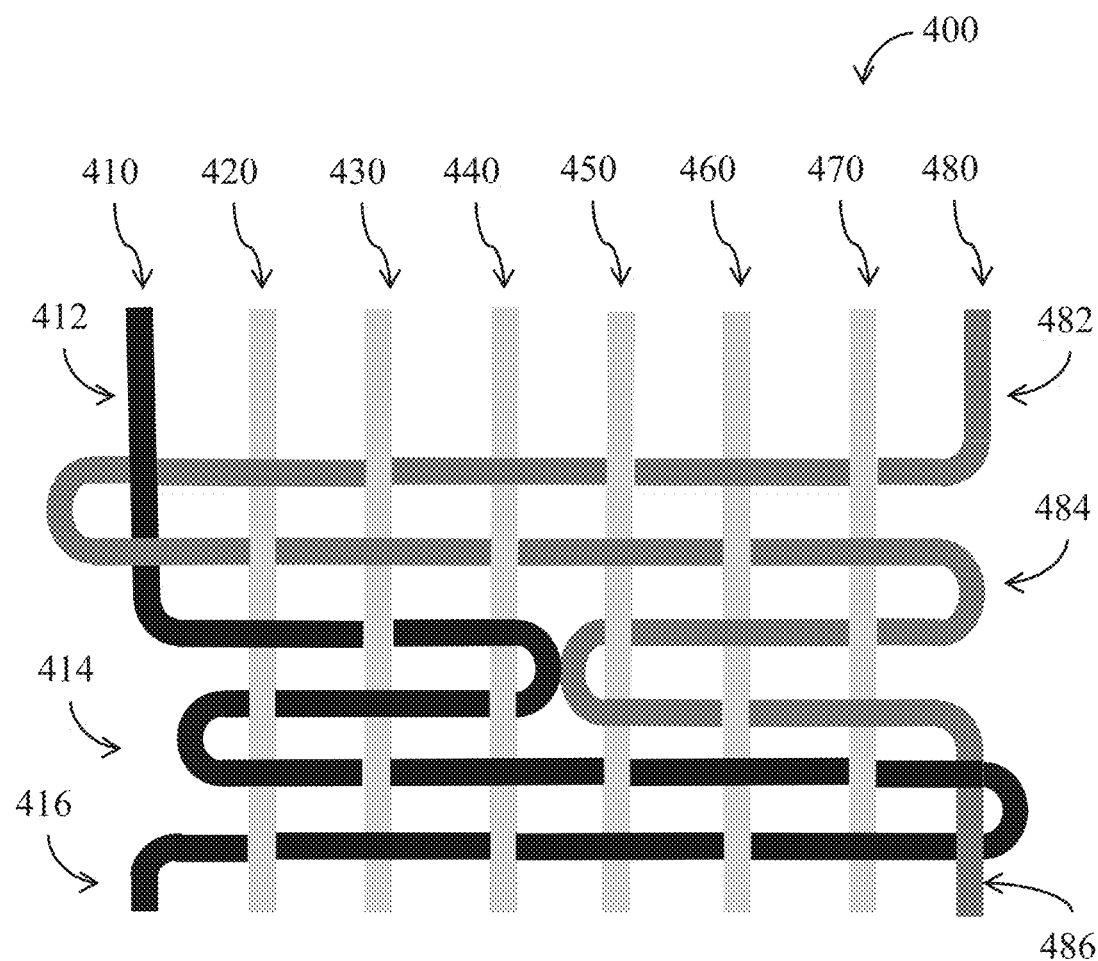
FIG. 4 schematically illustrates an interlocked thread structure with adjacent horizontal portions of different threads, according to an embodiment of the invention.

Reference is made to FIG. 4, schematically illustrating an interlocked thread structure 400, with adjacent horizontal portions of different threads, according to some embodiments. In certain embodiments, structure 400 has multiple threads 410, 420, 430, 440, 450, 460, 470, and 480, wherein each thread has its own path. For instance, thread 410 has a first vertical portion 412, a horizontal portion 414 and a second vertical portion 416, and thread 480 has a first vertical portion 482, a horizontal portion 484 and a second vertical portion 486. As illustrated, horizontal portion 484 of thread 480 and horizontal portion 414 of thread 410, both participate in forming at least one beat, herein illustrated with two beats.

Figure 5A:
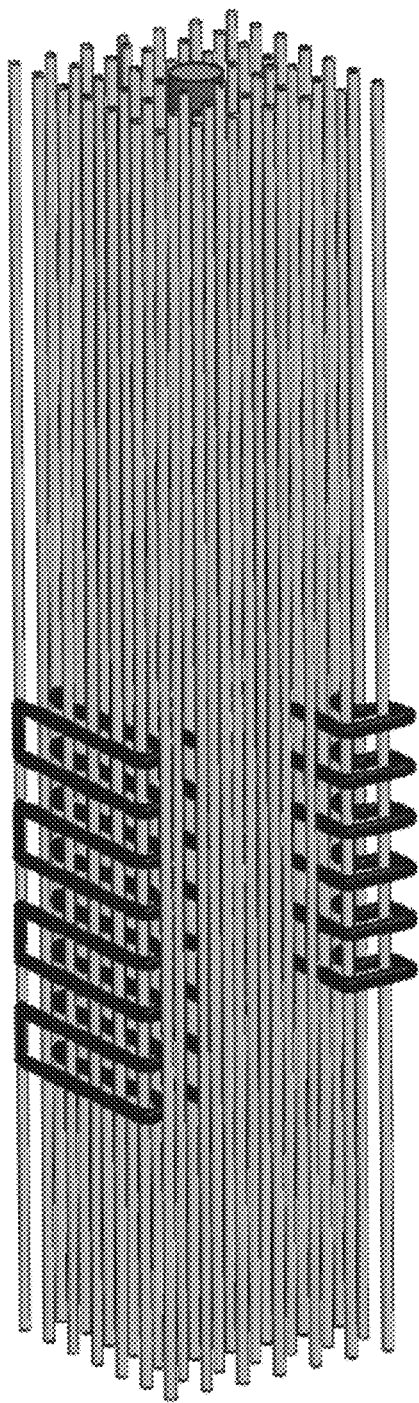
FIGS. 5a-5b schematically illustrate interlocked planar structures, according to some embodiments.
Figure 5B:
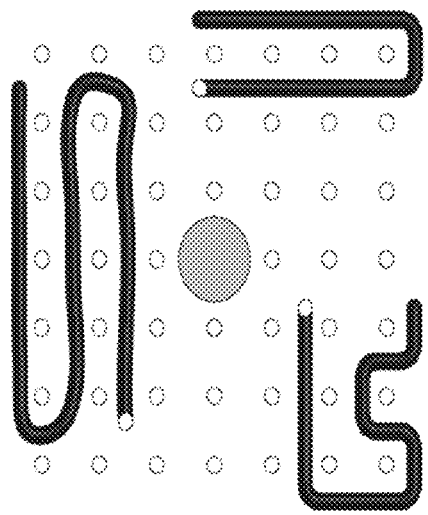

Reference is made to FIGS. 5a-5b, schematically illustrating interlocked planar structures, according to some embodiments of the invention. In some embodiments, the interlocked threads are arranged to form a volumetric structure, such an elongated box, a cylinder, or the like, wherein the vertical portions of threads are positioned at certain locations in space and extending towards a forming end where beats are created with horizontal portions of other threads. According to other embodiments, electrodes with certain shapes may be produced by interlocking threads in methods as described herein or similar thereto, formed to have determined characteristics, both structurally and functionally.

Figure 6:
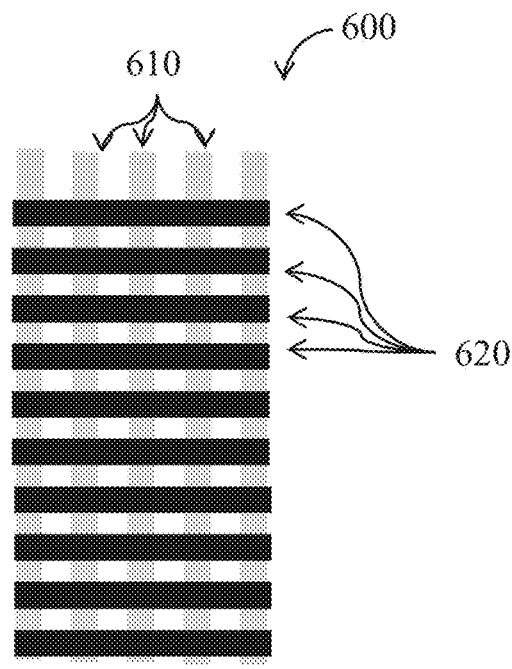
FIG. 6 schematically illustrates fabrication of an electrode with interlocked threads, according to an embodiment of the invention.

Reference is made to FIG. 6 that illustrates an electrode 600 produced with interlocked threads. In certain embodiments, electrode 600 has an elongated shape, made of vertical portions of threads 610 and beats formed from horizontal portions of threads 620. In certain embodiments, a number of threads in electrode 600 may be selected for forming contacts at certain positions on the surface of electrode 600 as well as volumetrically shaped within the body/volume of electrode 600 by interlocking the functionalized thread in a desired way with other threads.

The term "functionalized thread" and abbreviations thereof as used herein, refer to threads that at least a portion thereof was functionalized, e.g. by: (i) removing the coating material to expose the internal conductive material of the thread to create a contact; (ii) incorporating/depositing specific material(s) within the electrode lead during fabrication, followed by manipulating/modifying to obtain a desired functionality and/or structural property.

Figure 7A:
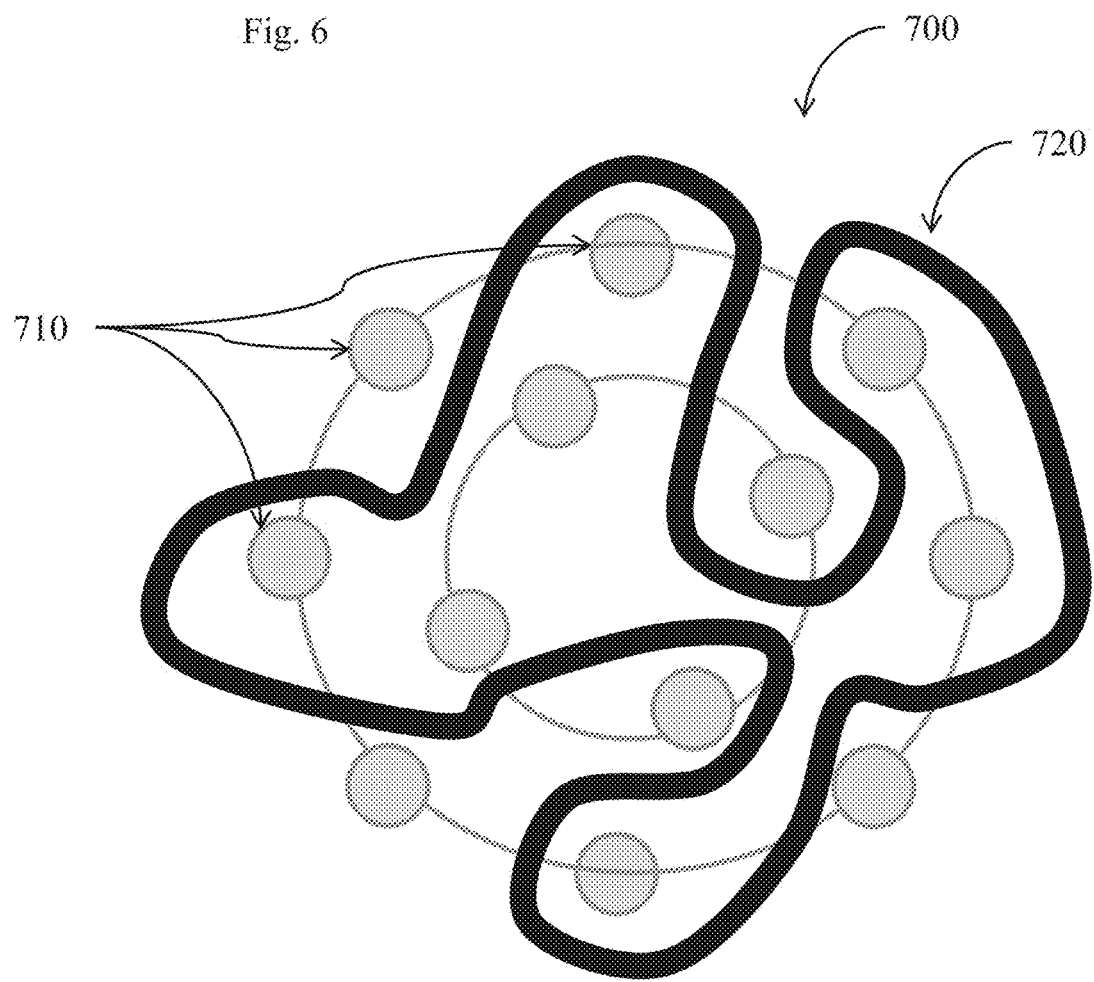
FIGS. 7a-7c schematically illustrate horizontal cross-sections of exemplary electrodes, according to some embodiments.
Figure 7B:
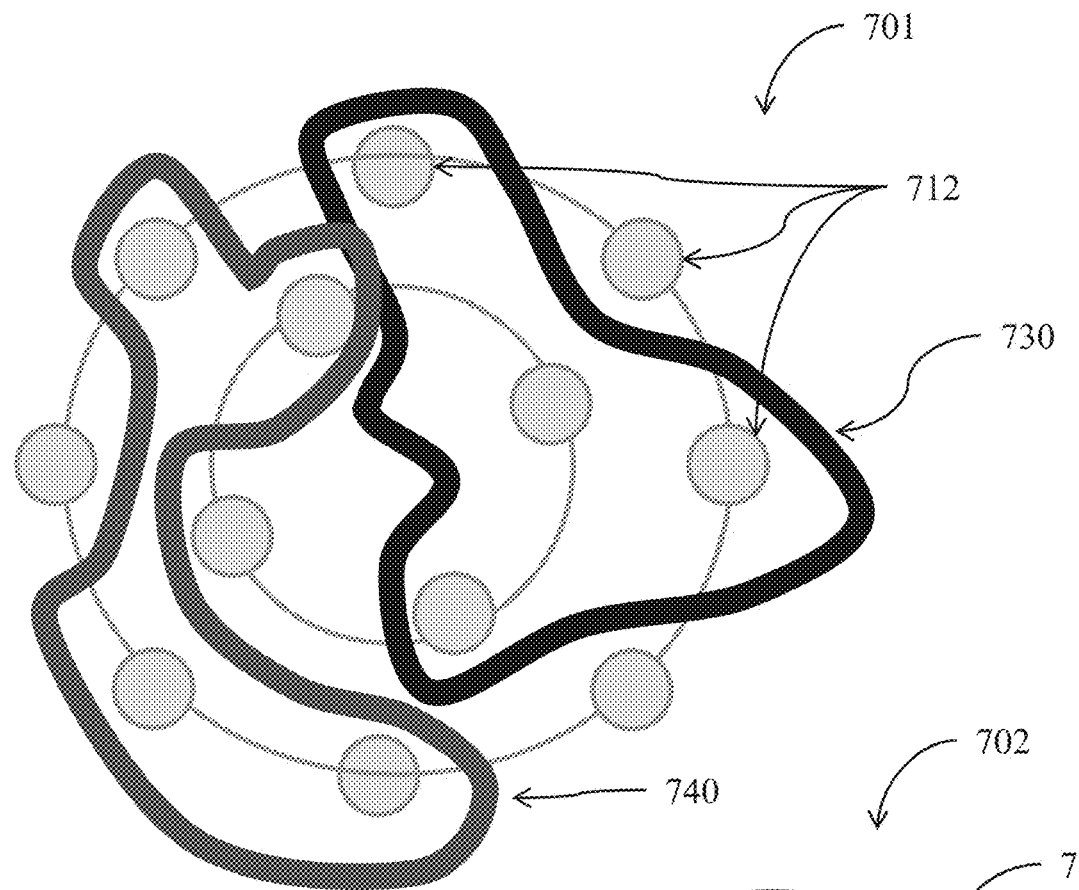
Figure 7C:
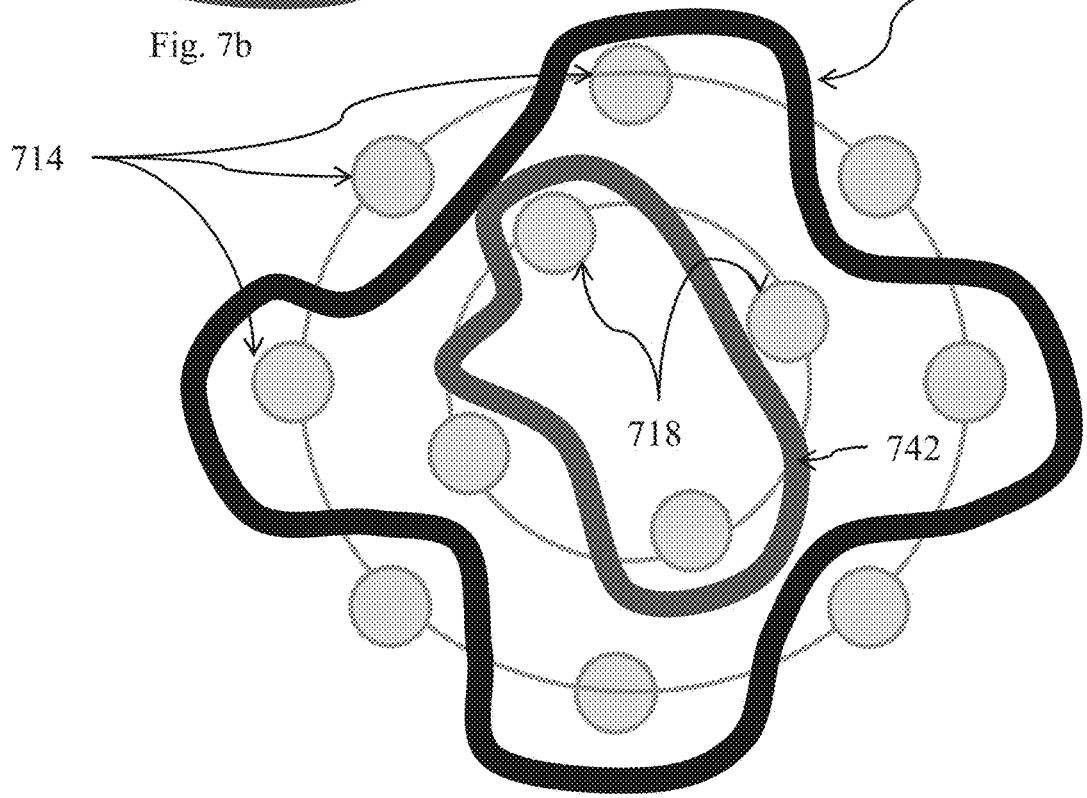

FIGS. 7a-7c schematically illustrate various horizontal cross-sections configurations of electrodes of the invention. FIG. 7a illustrates a cross section 700 of an electrode, wherein a single horizontal portion 720 of a thread forms a beat by passing and interlocking with vertical portions of other threads 710 arranged at certain positions in space to define the shape of the electrode. FIG. 7b schematically illustrates a cross section 701 of an electrode, wherein two horizontal portions of different threads, such as horizontal portion of thread 730 and horizontal portion of thread 740 forms a beat by passing and interlocking with vertical portions of other threads 712 arranged at certain positions in space to define the shape of the electrode. FIG. 7c illustrates a cross section 702 of an electrode, wherein two horizontal portions of different threads, such as horizontal portion of thread 732 and horizontal portion of thread 742 form a beat by passing and interlocking with vertical portions of other threads. Specifically, as illustrated, horizontal portion of thread 732 is configured to pass and interlock with vertical portions of outer layer threads 714, and horizontal portion of thread 742 configured to pass and interlock with vertical portions of inner layer threads 718.

It is noted that the closed circular shapes of the horizontal portions of threads are brought for illustrative purposes, and commonly, each beat, or each horizontal portion participating in a beat, would have an entry point to the beat, which is where the pass of the horizontal portion begins in the particular beat, and an exit point, which is the position of the thread when the particular beat formation is finished.

Figure 8A:
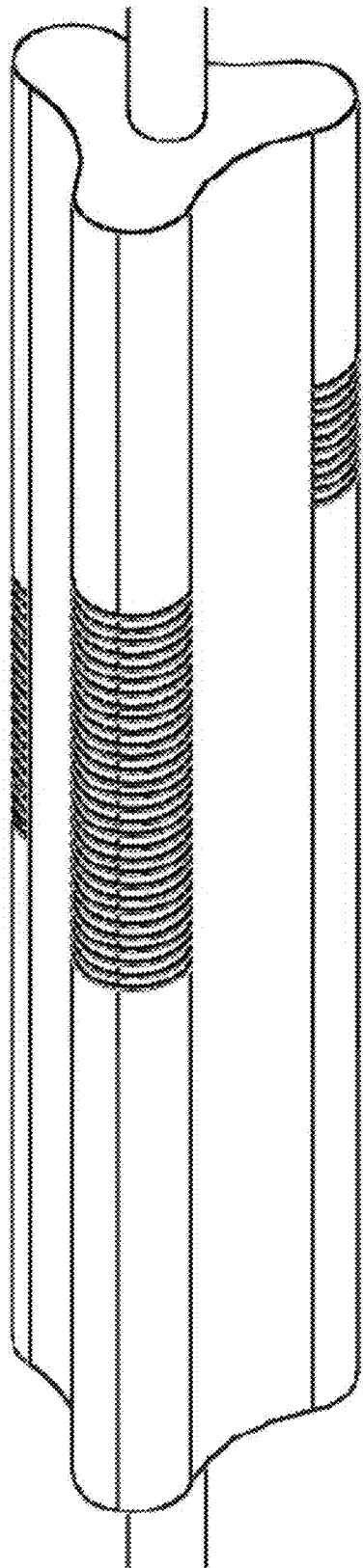
FIGS. 8a-8d schematically illustrate various possible shapes of an electrode according to the invention.
Figure 8B:
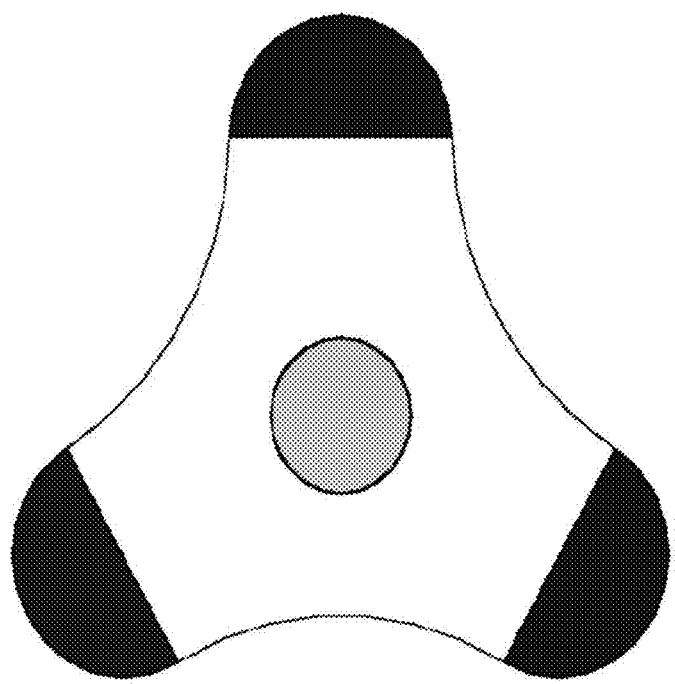
Figure 8C:
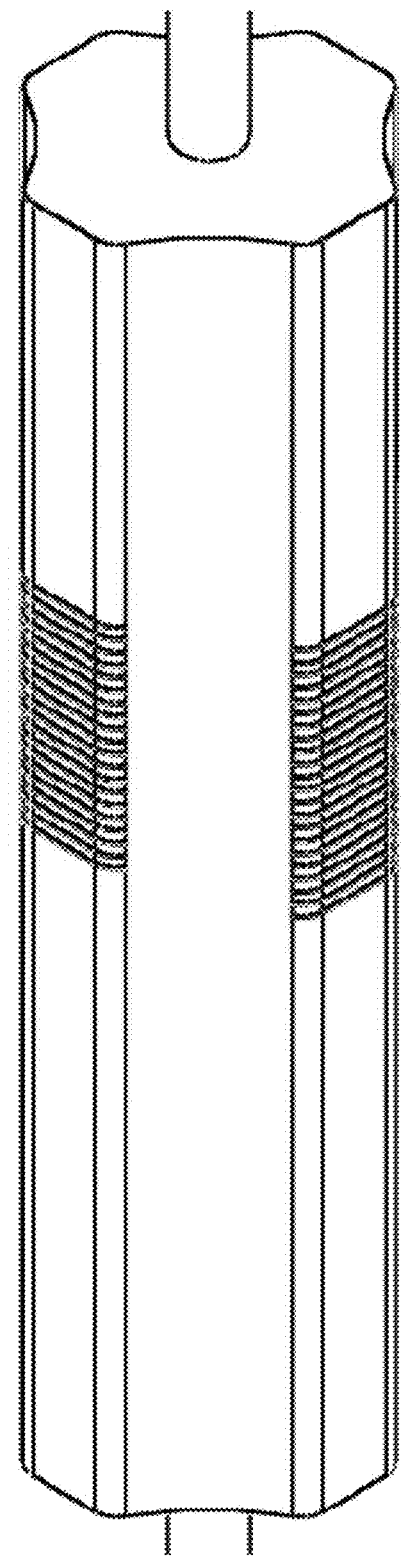
Figure 8D:
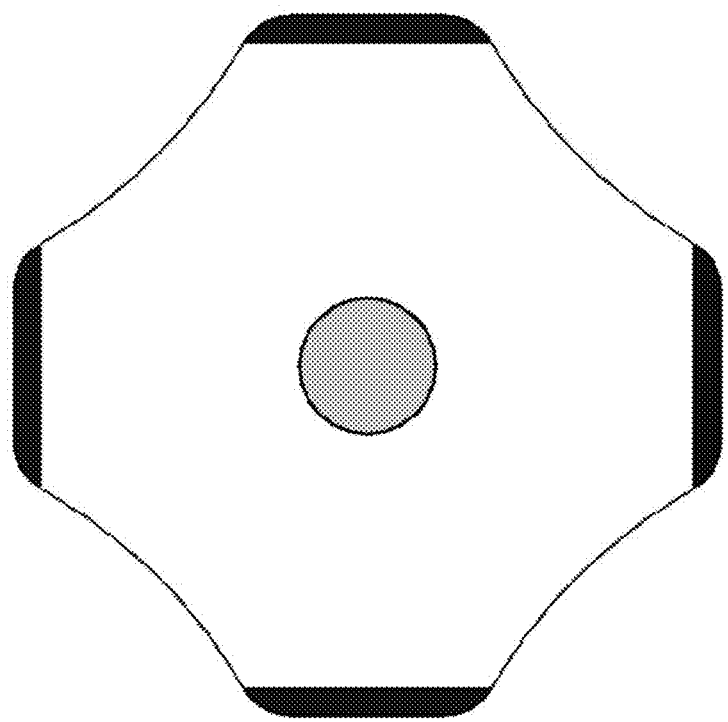

In certain embodiments, electrodes produced according to the invention may be in any shape, size and length, and can be fabricated and designed according to specific needs. For instance, the electrode may be rectangular, triangular, round or star-shaped. FIGS. 8a and 8c schematically illustrate two possible shapes of such electrodes fabricated according to the teachings of the invention. FIGS. 8b and 8d are cross-view of each electrode, respectively. In other embodiments, the electrode can be planner, have a single- or multi-tip end, have a single electric contact or many, etc.

According to some embodiments, threads may be interlocked and functionalized at certain locations on the surface of the electrode structure and/or within the volume thereof to achieve desired characteristics and functionalities.

Reference is now made to FIGS. 9a-9e, which schematically illustrate electrodes 1100 with multiple contacts, according to some embodiments. As seen, an electrode 1100 may include contacts having different shapes and sizes, at different positions, e.g. a first rectangular contact 1102, second 1104 and third 1106 contacts positioned in close proximity at the same vertical length, and an oval contact 1108. In certain embodiments, the shape of the contacts are arbitrary and amorphous 1110, 1112.

In certain embodiments, an electrode lead 1100 is made of a plurality of conductive filaments that are coated with non-conductive material wherein some weaved filaments having their coating removed and conductive part exposed, act as electrode contacts 1102-1114. The electrodes 1100 have a surface that flushes with the outer surface of the electrode lead.

Figures 9A, 9B:
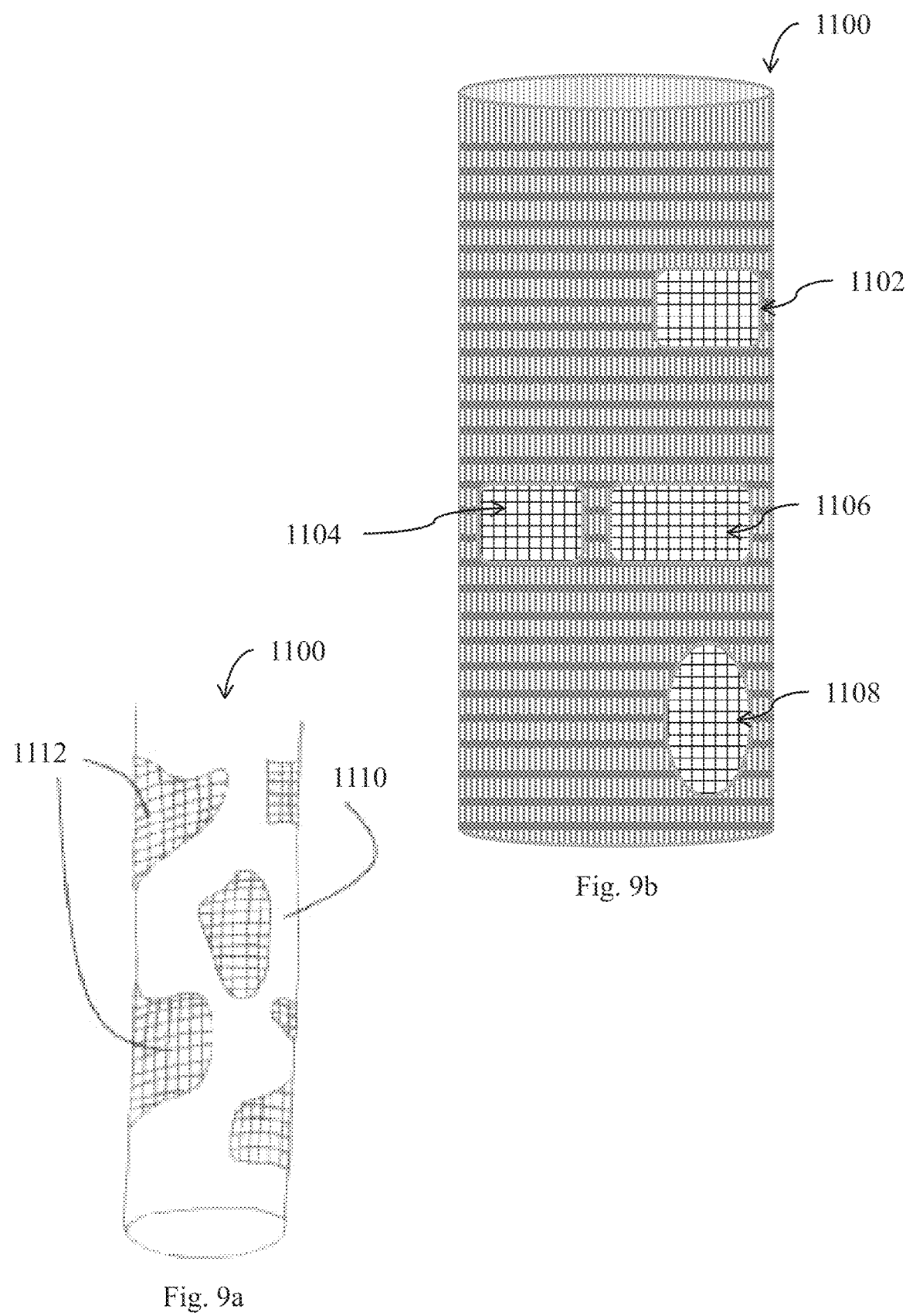
FIGS. 9a-9e schematically illustrate weaved layered electrode leads with multiple contacts, according to some embodiments.
Figure 9C:
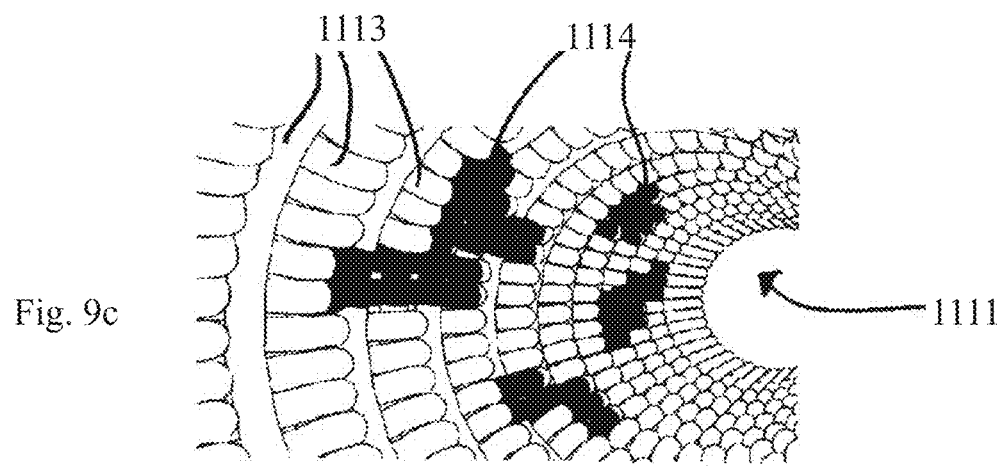
Figure 9D:
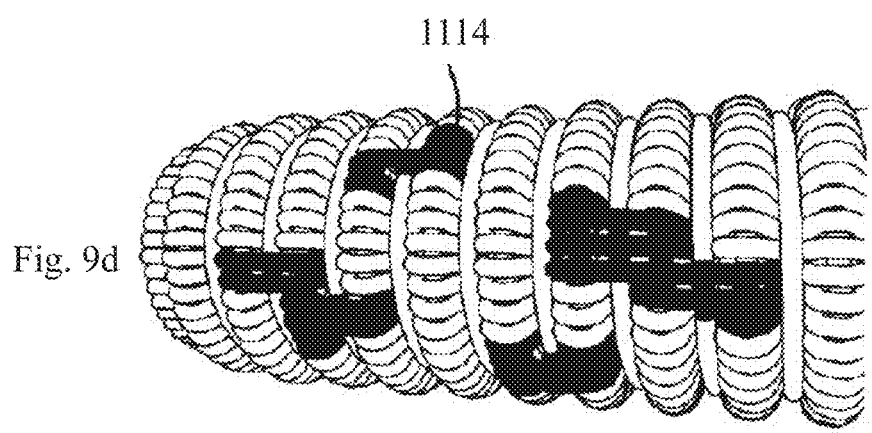
Figure 9E:
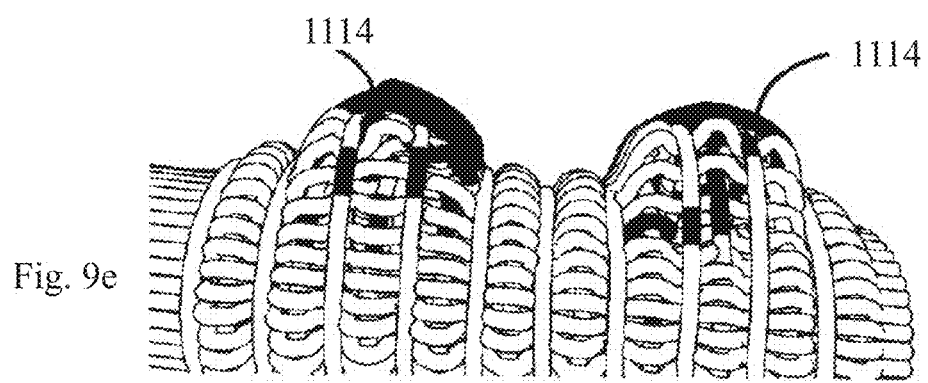

FIGS. 9c-9e illustrate schematic drawings of distal portion of electrode leads according to exemplary embodiments in different view angles. FIG. 9c illustrates a view of a portion of the distal side of an internal surface of an electrode lead 1111 wherein an electrode 1114 is provided within a volume in the electrode lead. The electrode lead is a structure of interlocked filaments 1113 that can be fabricated using methods such as braiding, knitting, weaving, interwinding, entangling, meshing, and a combination thereof.

In FIG. 9d, an electrode lead is depicted. However, the electrodes 1114 in the distal portion of the lead are designed to have at least one surface that is flush with the outer surface of the lead. In the architecture shown in FIG. 9e, the electrodes 1114 protrude from the outer surface of the electrode lead. In this way, electrodes with larger exposed surface 1114 and different directionalities can be fabricated. One of the advantages of this architecture in which the electrode protrudes of the electrode lead is that the diffusion of the fluids between the filaments is increased and therefor the capacity of the current can be higher.

Optionally, the electrode comprises filaments made of conductive material coated by a nonconductive material. In order to form contact surfaces within the lead that are capable of transferring electrical signal to the electronics module (or vise-versa), a portion or a segment of the nonconductive coating is removed from the filament so as to expose the inner conductive material. The coated conductive filaments are integrated within the woven, knitted, or other such structure while parts of their coating are being removed during fabrication of the structure. The contact surface area of the electrode is a cumulative electrically active surface made of several adjacent exposed areas of several filaments.

In certain embodiments, a thread used by the method and thread interlocking machine of the invention is made of biocompatible materials, such as: non-conductive polymers used for the structure; isolated and non-isolated carbon fibers/nanotubes; pl-ir coated wires with parylene-C or other polymers; coated platinum wire; metal plated wires with insulated coatings; enhanced wire cores with proper surface treatment e.g. TIN coating; Black Platinum; and PDMS that are coated with an insulation layer.

In certain embodiments, since the electrode lead is made of filaments, it is possible to design the distance between the filaments to be such that the bodily liquids in the vicinity of the electrode lead are electrically interacting with the contact surface area of the exposed filaments of the electrode that is positioned within the lead structure.

In tissue stimulation or sensing, the interaction between the electrode contact and the tissue happens in the metal-to-tissue interface, and it is affected by the total contact area. The more surface area of the contact the less impedance the more charge capacity it is possible to send to the tissue through the lead. In sensing the more surface area of the contact, the less the impedance of the contacts, the better quality of the recorded signals. In order to shape the electrical field and send it towards desired brain regions, it is desirable that an electrode lead comprises as many individually driven tiny electrode contacts as possible, optionally each tiny contact prefers a certain direction. Tiny contacts have smaller surfaces, and accordingly the present invention provides electrodes with many contacts that have preferred directionality while at the same time have a very large surface area of the electrode tissue interface and thus a greater charge capacity. This is accomplished by the creation of volume contacts that have increased surface areas that can be created by various methods as described herein.

Optionally, the lead can be designed and fabricated to have a volume such as a pocket or a void, and the contact is inserted/provided to within the volume after the lead is fabricated. According to some embodiments, the electrode may be separately fabricated and can be designed in a similar manner as the lead or using other fabrication methods.

According to some embodiments, after inserting the electrode into its designated area/volume, it is integrated with a structure of the lead and is electrically connected to the electronics module. Alternatively, the contact is made of at least one conductive filament that is wrapped within the void.

In certain embodiments, the depicted architecture of the electrode contacts of the invention are volumes that are mostly embedded within the lead structure with portion of their volume surfaces in direct contact with the tissue around the electrode lead. These contacting surfaces render the electrode contact its preferred directionality while the electrode contact volume contributes towards improved electrode contact performance.

In certain embodiments, the electrode lead of the invention is specifically designed according to need by designing and establishing specific architectures of the integration and ordering of the filaments establishing the electrode's body within the structure of the electrode lead.

Figure 10A:
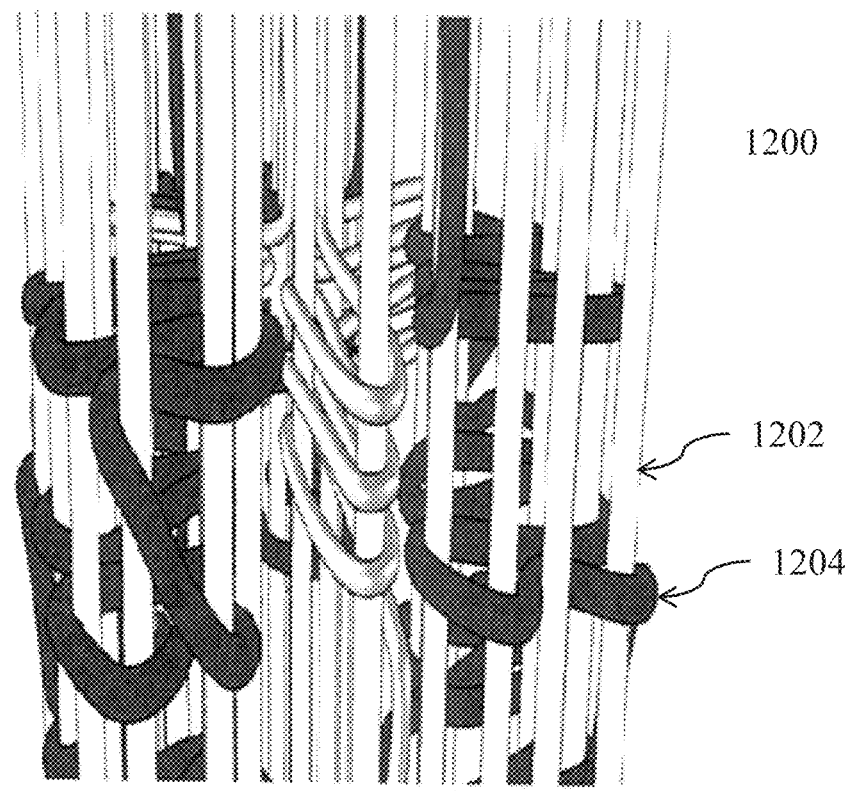
FIGS. 10a-10e schematically illustrate single thread electrode in a lead.
Figure 10B:
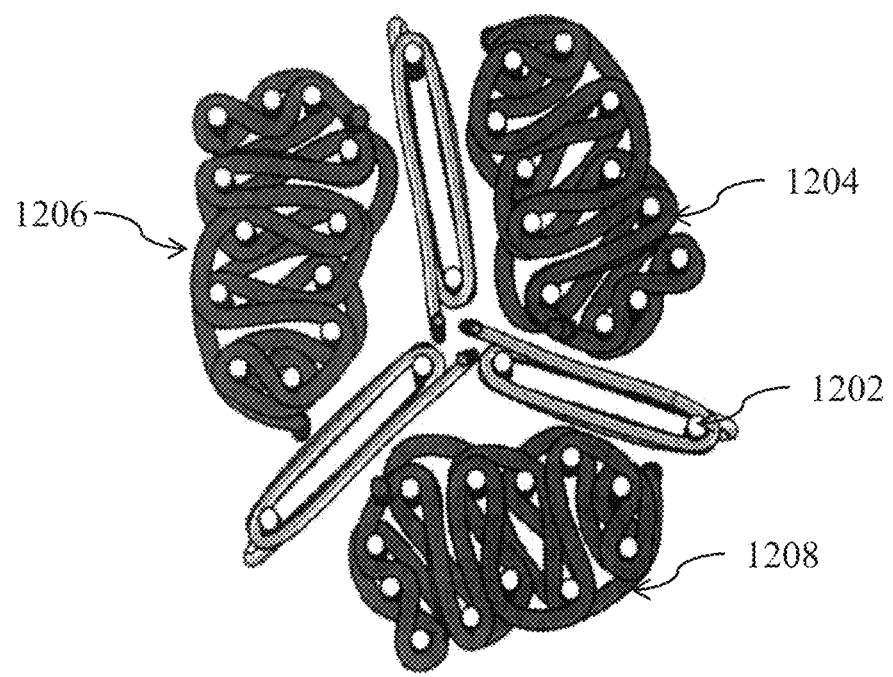
Figure 10C:
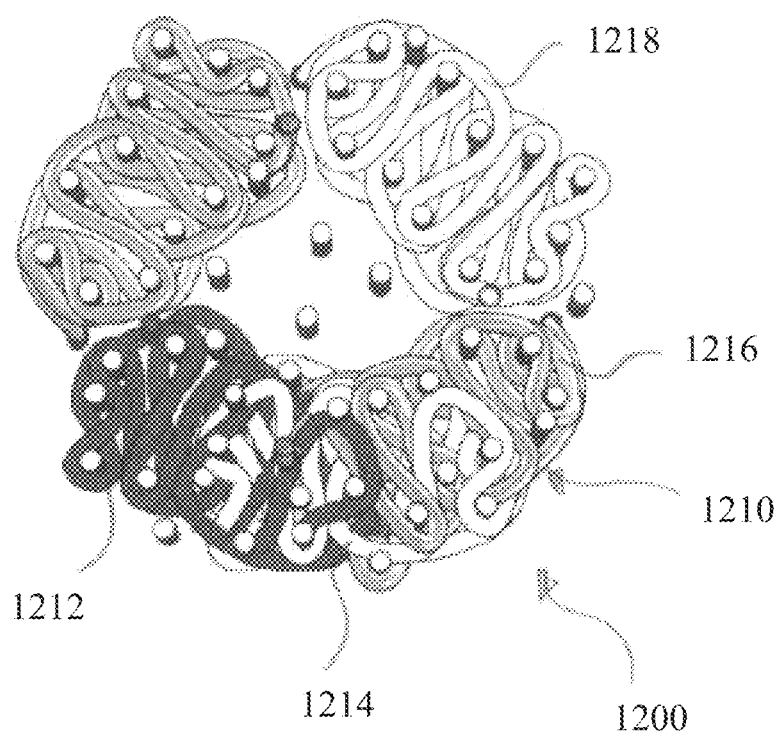

Reference is made to FIGS. 10a-10c, which schematically illustrate single thread electrode in a lead in accordance with an exemplary embodiment (FIGS. 10a and 10d) and a cross sectional view thereof (FIGS. 10b and 10e, respectively) showing three separated electrodes across the cross sectional area of the lead.

As seen in FIG. 10a, lead 1200 is made of interlocked non-conductive filaments 1202, ordered in an interlocked structure. In a certain predetermined area, a conductive single thread 1204 is provided with a predetermined outer surface that flushes with an outer circumferential surface of the electrode lead 1200. In this way, the single thread 1204 establishes a contact surface that is manageable and controllable. Thread 1204 is folded and entangled about several vertical filaments 1202 and several beats so as to establish an area of exposed conductive material that establishes the electrode contact active surface area. As seen in a cross sectional view of an electrode lead shown in FIG. 10B, more than one electrode can be positioned in a certain cross section: three single thread electrodes, 1204, 1206 and 1208 are shown to occupy a volume in the same cross sectional area of the electrode lead. It is clearly seen that the threads are folded and entangled about the vertical filaments 1202. It should be cleared that the folding about the vertical filaments are shown in the figure only due to clarity of figures issue and the folding can be about all types of filaments that establish the structure of the lead.

Notably, as shown in FIG. 10b, each of the electrode contacts is provided with an isolated conductive filament that passes electric signals to or from an electronics module (not shown). Such single thread electrode contacts can be distributed in the electrode lead in a custom-made manner according to need. Moreover, more than a single thread can be used for one electrode or more than one. Accordingly, an electrode thread can be folded about other filaments such as nonconductive filaments that are coated and conductive filaments. The entanglements and folding can be about other filaments that are interlocked and form the base structure of the lead.

In certain embodiments, the thread that forms the folded electrode can be made of at least one of the filaments that establishes the base structure of the electrode lead that is being folded about the structure. When said filament is made of coated conductive material, then at the folded area constructing the electrode contact area, the coated isolating material is being removed, prior to the folding and weaving of the filament in place, in order to expose the conductive material that forms the contact.

In certain embodiments, such folded area made of at least one thread can is integrated within an electrode having a regular structure as used in the industry. Alternatively, it is combined in other electrode structures.

In certain embodiments, electrodes are structured to have one or more coaxial layers. According to some embodiments, some layers are movable longitudinally in relation to others. According to other embodiments, an electrode includes two-, three-, four-, or five layers. or more. According to some embodiments, the positioning of the layers may be adjusted for achieving different functionalities, or alternatively for tuning/amending one or more functionalities such as a directionality of an electric and/or a magnetic field.

FIG. 10c illustrates another cross sectional view of an electrode lead according to the invention having volume sharing electrodes. The electrode lead 1200 is provided with a volume 1210 in which more than one contact is placed. A first electrode contact 1212 is provided with a plurality of contact surfaces electrically connected to an electronics module. A second electrode contact 1214 with a plurality of contact surfaces that are also electrically connected to the electronics module. An electrode contact 1216 with a plurality of contact surfaces is provided as well, wherein the metals of these contacts do not necessarily shorted. As illustrated, all three contacts are having a shared volume of the volume 1210 they are occupying in the electrode lead. One of the advantages of using such architecture is using the same volume at the same time for stimulating a tissue and sensing it, e.g., without increasing the size of the lead. It should be noted that the electrodes can be used for sensing, stimulating or any other combination between those two options. This brings about some other possibilities of utilizing the electrode lead. Other electrodes such as electrode 1218 can be provided in its own volume. Another advantage is the ability to change the directionality of the electrode. By using an electrode lead 1200 while using the three electrodes as sensing/stimulation electrodes, one can simultaneously move the directionality of the sensing or stimulating electrode by starting with one electrode, then moving to the other electrode and continue to the next. The resolution of the directionality of the electrodes when they share the same volume can be fine-tuned.

It should be noted that the contacts in the volume can be fully overlapped if, e.g., the architecture of the electrodes is by interlocked filaments then the filaments of the three electrodes can be overlapped. It is possible to combine the any of the architectures described herein: for instance, an electrode can partially be made of filaments and partially made of a sponge-like or porous material. This enables to fully control the directionality of the electrode.

According to another aspect, an electrode lead is provided having on its surface multiple guiding-marks having a predetermined or known spacing therebetween. The guiding marks can be used as a measuring means and are configured to facilitate measuring a distance from a reference point on the electrode lead to another spot.

Figure 11A:
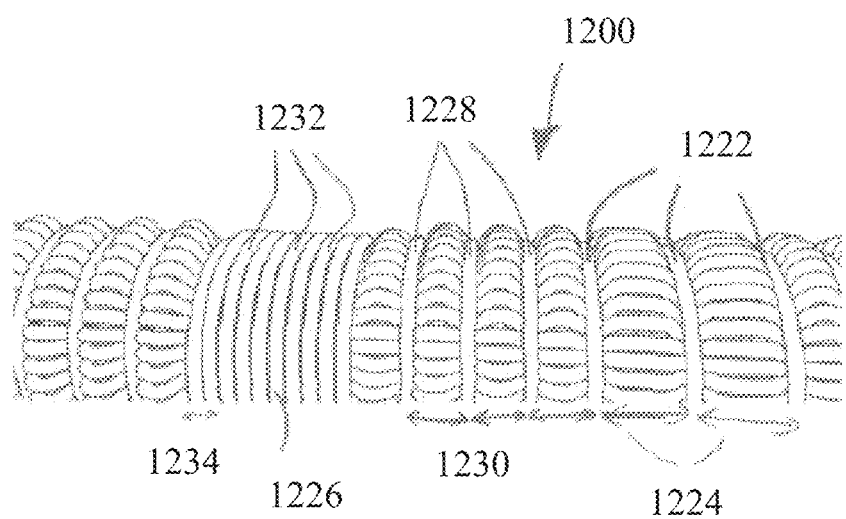

Reference is now made to FIG. 11a illustrating an electrode lead 1200 with markings onto it according to an exemplary embodiment. In specific embodiments, the electrode lead 1200 is provided with markings 1222 that are of constant dimensions and are distant from one another by a certain predetermined and constant distance 1224; markings 1228 that are of constant dimensions and are distant from one another by a certain predetermined and constant distance 1230; and markings 1232 that are of constant dimensions and are distant from one another by a certain predetermined and constant distance 1234. In this way, a known reference point 1226 on the electrode lead 1200 can be used to measure a distance from the reference point 1226 to another point on the electrode lead or outside of it. Other usage of such a design can be for placing the electrode lead in a certain location in a bodily part, exposing a contact in a position that is custom-made, deploying masking material, etc.

The multiple guiding-marks can preferably be predetermined filaments that form and design patterns of the material that forms the electrode. The markings can be fabricated on the electrode lead during fabrication of the lead or afterwards, according to need. The markings can be deposited in the electrode lead using a method that will be explained herein after.

Figure 11B:
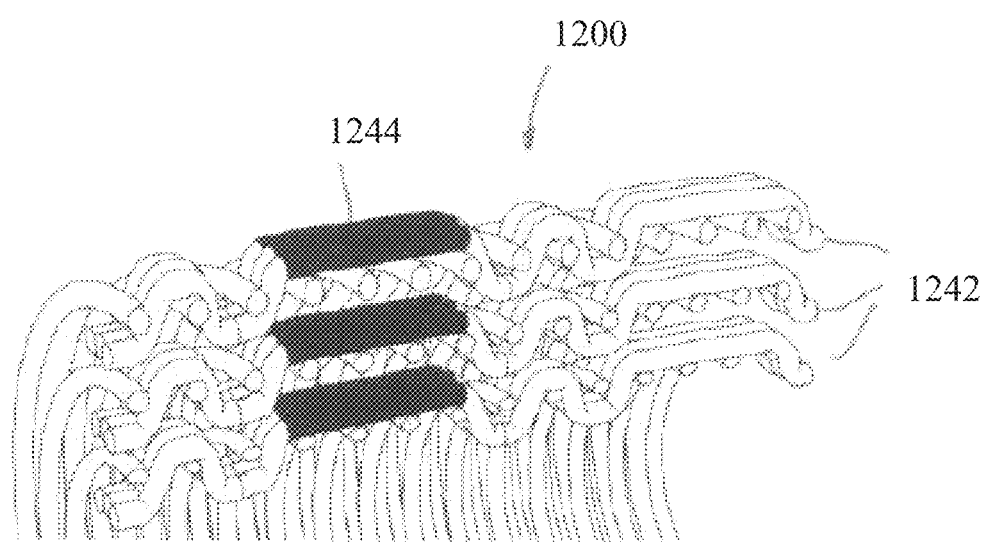

Reference is now made to FIG. 11b illustrating an electrode lead 1200 with markings onto it according to another embodiment. In certain embodiments, the electrode lead 1200 is made of layers 1242, some of which are marked 1244. In this way, measurements can be performed also in the inner structure of the electrode lead. Notably, these structures can be connected together to form one 3-dimentional structural electrode.

In another aspect, the electrode may comprise a deposition of material(s) within the structure of the electrode lead. The material(s) can be inserted to within the electrode lead structure during fabrication, construction, or manufacture of the electrode lead. The deposition material(s) is positioned within the structure of the electrode lead at predetermined location within the electrode lead structure and optionally, at predetermined times during the manufacturing process. Optionally, the deposited material(s) is post treated so as to form a change or transformation of the deposited material(s). Accordingly, after manufacturing the electrode lead the deposited material is treated to form a medium capable of achieving a desired property or function.

Figure 11C:
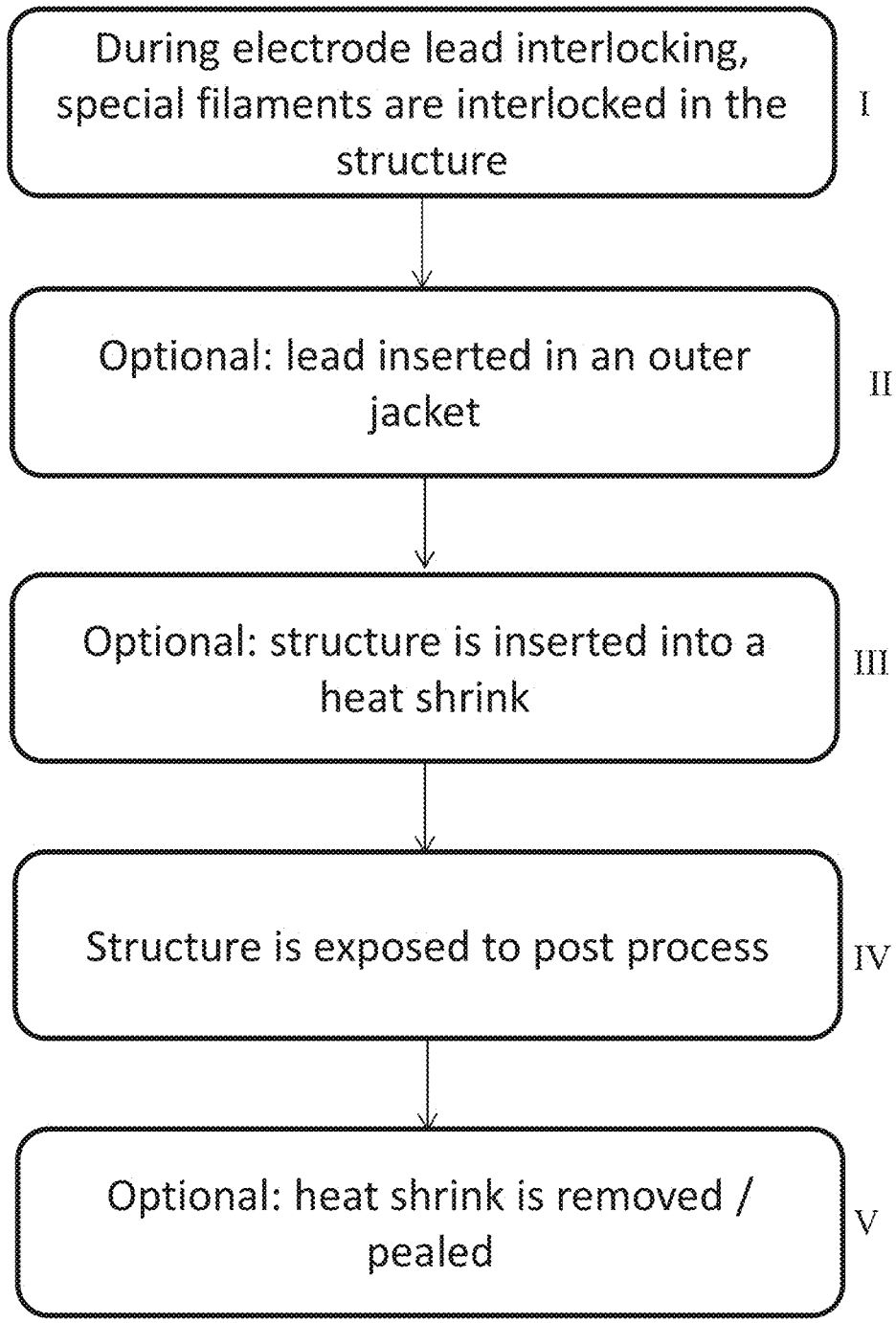

FIG. 11c is a block diagram of a method by which deposition can be performed in accordance with certain embodiments: during the electrode lead's fabrication process, functional filaments or bulks can be interlocked within the structure of the lead (I). Optionally, the whole lead may be inserted into an outer jacket (II) that can remain after the lead is ready or removed thereof. Then, optionally, the complex of the electrode lead and the outer jacket can be inserted into a heat shrink, i.e. a structure that shrinks when heated (III), followed by subjecting the entire complex, optionally with said heat shrink, to post process (IV). As mentioned herein before regarding the jacket, the heat shrink as well can be removed or pealed after the post process (V).

Figure 12A:
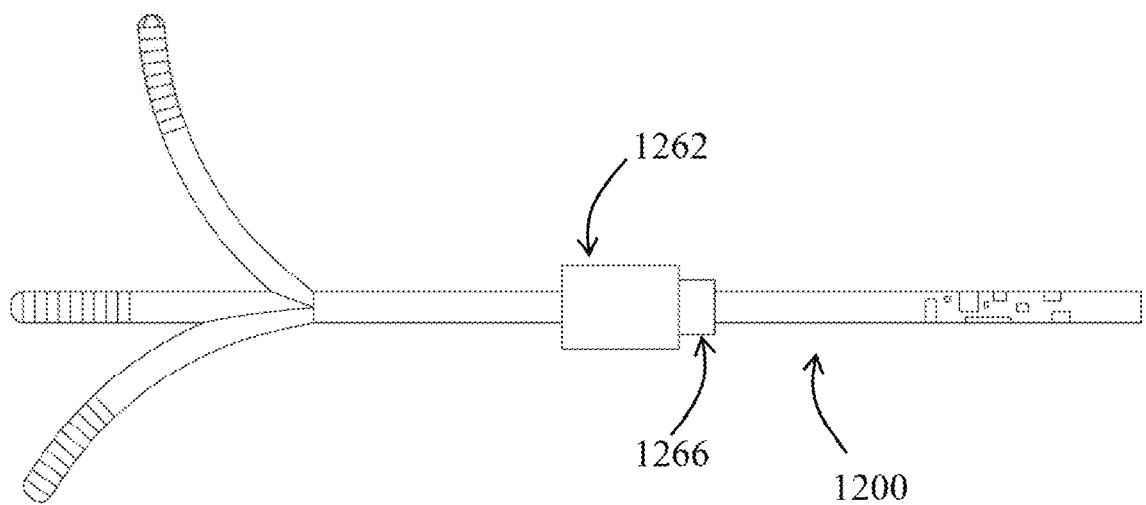
FIGS. 12a-12g illustrate electrode leads with a barrier portion in accordance with an exemplary embodiment and a method of fabricating same.

In certain embodiments, the electrode lead of the invention is fabricated with a barrier portion. Reference is made to FIG. 12a illustrating an exemplary electrode lead of the invention with a barrier portion, and to FIGS. 12b-12e illustrating a method of fabricating same.

In some applications, the distal side of the lead is implanted in a place having a different environment pressure than the proximal side of the lead, where it is desirable that the lead body does not introduce a leakage path that violates this difference between the areas. Alternatively, since the lead body is built from interlocked fiber that enables a path for fluids to pass between a distal- and proximal-side of the lead, the electrode lead's body may be formed such as to form a barrier: As illustrated in FIGS. 12b-12e, a post process is carried out for melting special filaments or an outer jacket using an external heat shrink, into the lead structure, thus filling the gaps in the structure and creating a barrier that prevents any pressure or fluidic leakages between the two sides of the barrier. Notably, this barrier can be produced by any suitable method, e.g. injection molding over the filaments.

In certain embodiments, heat shrinks (either pealable or permanent) are used and placed around the lead and/or the jacket, so that they shrink after application of heat, thus forcing melting of the special filaments or jacket, and creating a desired barrier. After this action, the heat shrink can be removed or can remain permanently as part of the lead body.

Figure 12B:
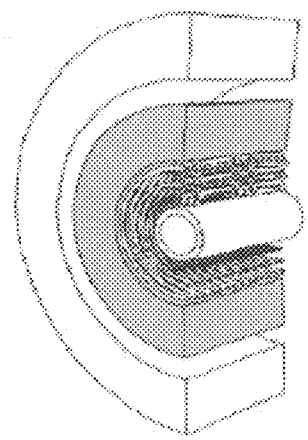
Figure 12C:
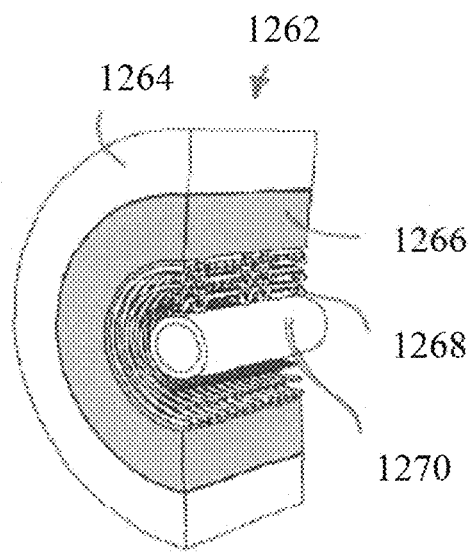
Figure 12D:
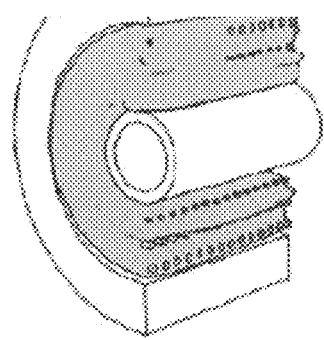
Figure 12E:
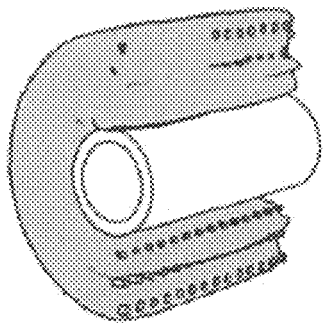

FIG. 12a illustrates an electrode lead 1200 with a barrier area 1262 provided with a jacket 1266 and a heat shrink 1264. One possible method by which the barrier structure can be formed is by including during the fabrication process a bulk of functional material such as a polymer 1266 in a state that can be molten afterwards. The polymer 1266 is integrated within the structure of the lead adjacent to filaments 1268. Alternatively, the polymer 1266 can be a hollow tube of a functional polymer that is inserted around the lead at the desired barrier location. After finalizing the fabrication of the electrode lead, the portion that needs to be enforced, is covered, e.g., by a jacket of polymer 1266 and optionally a heat shrink 1264 (FIG. 12b). Then, the full structure is built (FIG. 12c). The electrode lead is then subject to heat in order to let the polymer 1266 to melt into the filaments 1268 (FIG. 12d), and then the heat shrink is removed (FIG. 12e). FIG. 12a shows an electrode lead having a distal- and proximal end, an outer jacket wraps over the lead at a desired location(s), and then the complex is wrapped inside a heat shrink 1264; FIGS. 12b-12c are a zoom-in cross section along lead axis of the lead area incorporating the intended barrier, showing an inner guiding tube 1270 usually incorporated inside electrode leads. FIG. 12d illustrates how when the complex is exposed to appropriate heat causing the heats shrink to start shrink over the outer jacket. As heat accumulates, the outer jacket starts melting into the interlocked lead body thus forming a barrier. Finally, as shown in FIG. 12e, the heat shrink is removed/peeled away. In certain embodiments, the outer jackets are patterned, and have various opening/holes/different jacket thickness along the axis or circumference, so that when it is reflowed the pattern updates the lead composition accordingly.

Figure 12F:
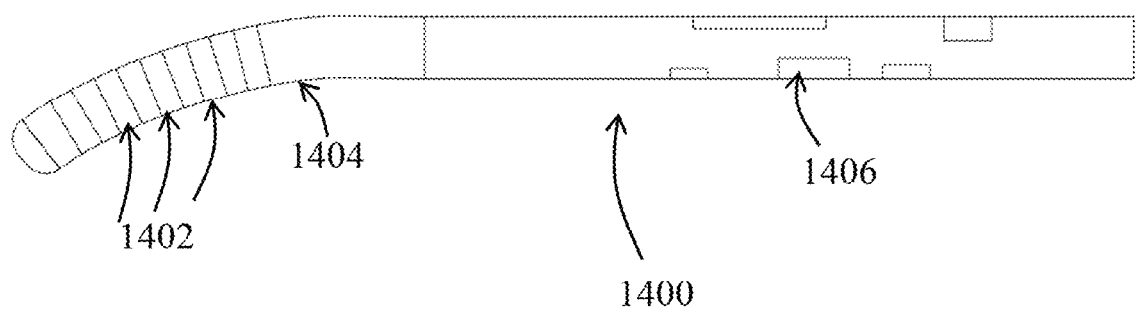
Figure 12G:
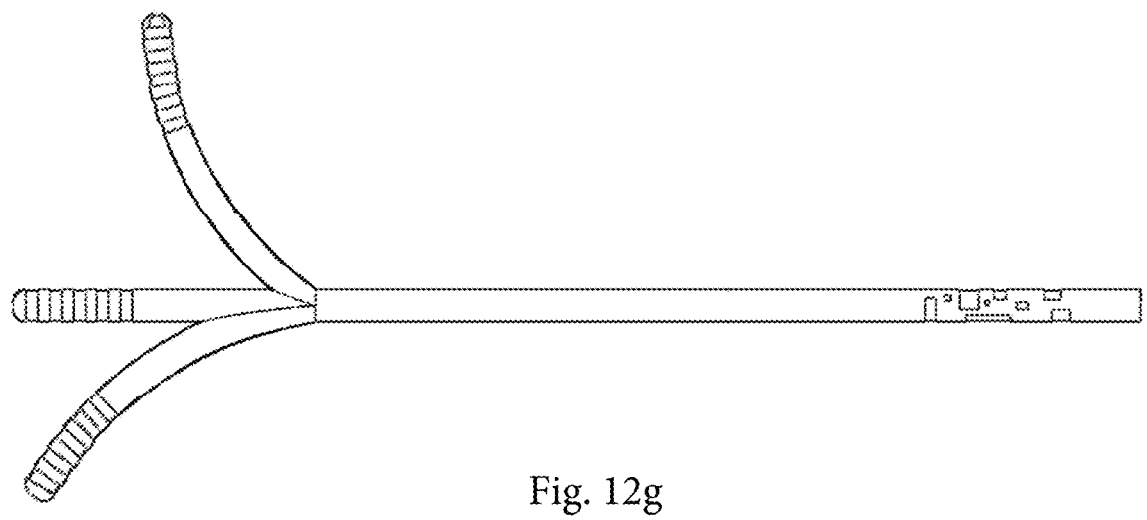

FIG. 12f illustrates an electrode lead with electrical connection terminals in accordance with an exemplary embodiment, showing: a lead 1400 with many electrode contacts 1402 at its distal end, each one connected with at least one conductor 1404 to a proximal lead conductive area 1406 that behave as connection terminals. FIG. 12g illustrates an electrode lead with electrical connection terminals in accordance with another exemplary embodiment, showing that the proximal end of the lead can be also split (during fabrication) into more than one distal ending, thus allowing accommodating as many connection terminals as possible. This feature further allows it to be compatible with multiple mating connectors. These conductive volumes can be in the form of coiled conductive filaments at each connection terminal or of any other configuration.

In certain embodiments, the deposited material(s) renders the electrode lead with several properties or functions such as isolation between contacts, robustness, erection of the electrode structure, masking some parts of the electrode lead for further manufacturing steps, patterning within the electrode, performing markings as discussed herein, etc.

In certain embodiments, the invention provides electrode connection terminals. The method of the invention enables to create and build volume conductive areas, which can also be used to supply electrical connection terminals, so that a mating connector will connect each conductive area, which behaves as a connection terminal to an individual channel in the electronics sensing or stimulation circuit.

Figure 13A:
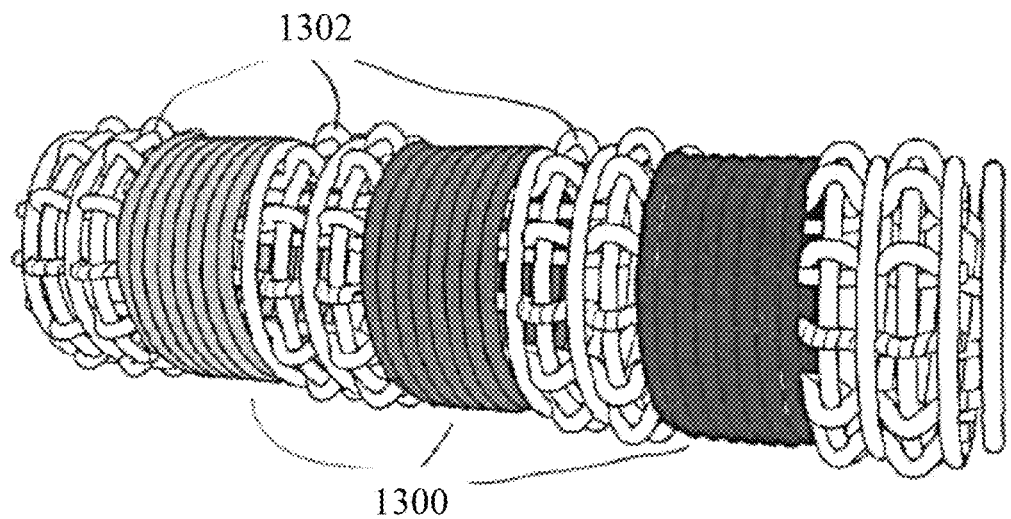
FIGS. 13a-13c illustrate electrical connection terminals in accordance with the invention.

FIG. 13a shows one option of connection terminals 1300 that are in the form of coiled exposed filament/wires wrapped around the lead circumference forming separate connection terminals that are not in contact with each other. Three contacts are shown that are separated by non-conductive areas 1302 allowing enough space so that no electrical short is formed between them. Each contact is optionally connected through a conductor to an electrode contact at distal side of the lead. The connection terminal can assume any conductive mass volume shape, and the mating connector terminal may be female, male, or pins that punch into the conductive terminal volume, etc.

Figure 13B:
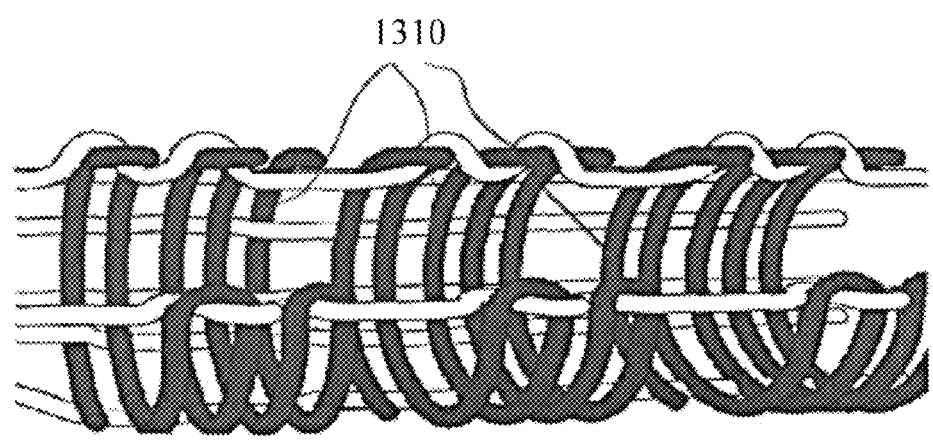
Figure 13C:
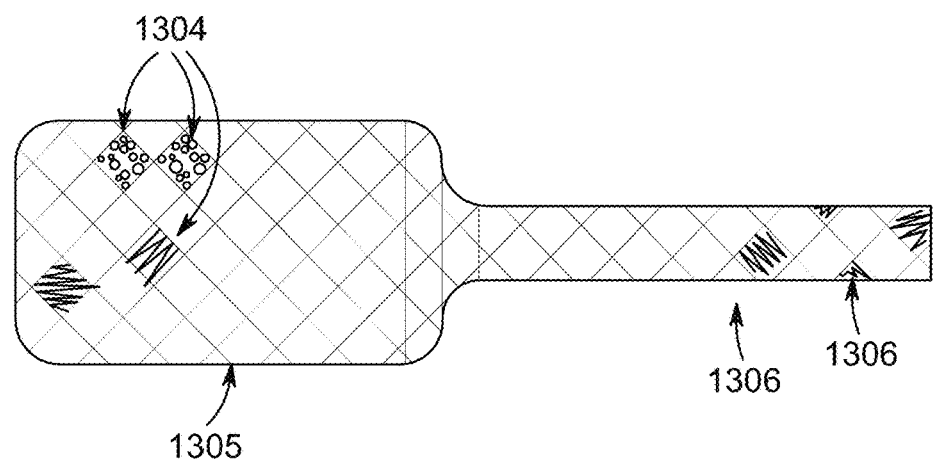

The connector could be internally positioned behaving as a female connection terminal or external behaving as a male connection terminal. FIG. 13b shows a connector terminal in female configuration. Three internal connection terminals 1310 behave as connection terminals that at one side can connect to a mating male connector and at the other side connected to electrode contacts through a conductor, or actually forming part-of the electrode contact, i.e. the same wire that forms the electrode contact and the electrode connector. FIG. 13c illustrates the lead distal end 1306 that includes electrode contacts 1308 while at the lead proximal end 1305, the connection terminals 1304 assume a planar configuration. These are conductive volumes that span through the thickness of the lead proximal end. The mating connector can have pins or protrusion that when clamped to the terminal connections at the proximal side of the lead will punch-in or penetrate-into the corresponding terminals conductive areas.

The mating connector could be a linear female that mates to connection terminal described in FIG. 13*a* or male mating connecting to terminal connections as described in FIG. 13*b* or even a clamp that clamps as described in FIG. 13*c* over the electrode connector terminal. Forming female's connector that have the ability to squeeze over male mating connectors, can be accomplished by interlocking/weaving/braining etc. the single connection terminal area by special patterns that allow flexibility and elasticity of the structure. When inserting the male connector, it will force the female contact to expand, while at the same time the female connector becomes more tensed thus pushing over the male elements in the connector. This behavior can also be accomplished by interlocking the conductor filaments that form the female contact area with elastic filaments: the electrode will be weaved with an internal diameter that is less than the outside diameter of the male contact, so that when the male connector is inserted into the lead distal end containing the female contact, the female connector flexible/elastic structure will expand while continuously pushing on the male connector.

Figure 14A:
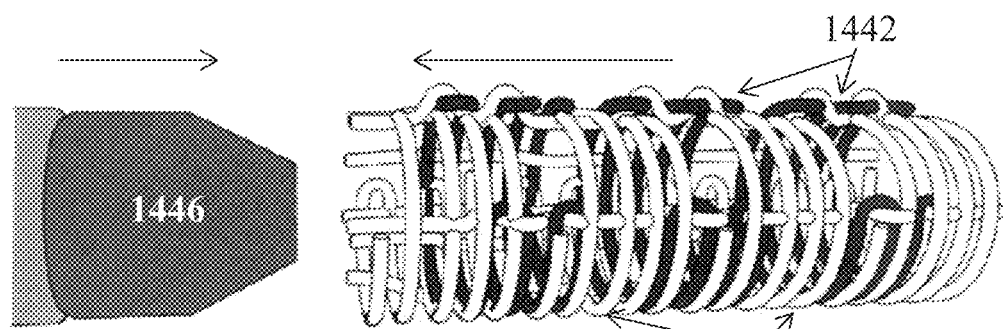
FIGS. 14a-14d illustrate insertion of a male mating connector into a female lead connector.
Figure 14B:
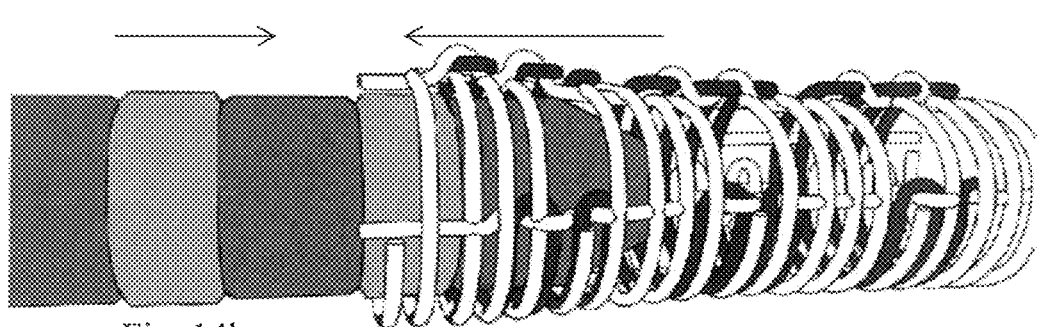
Figure 14C:
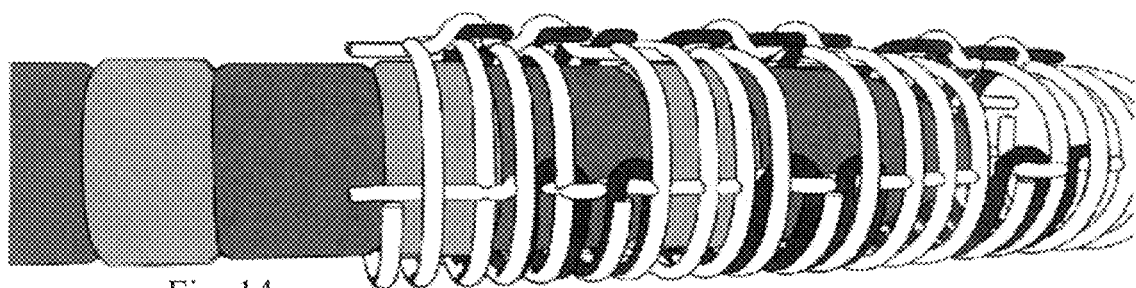
Figure 14D:
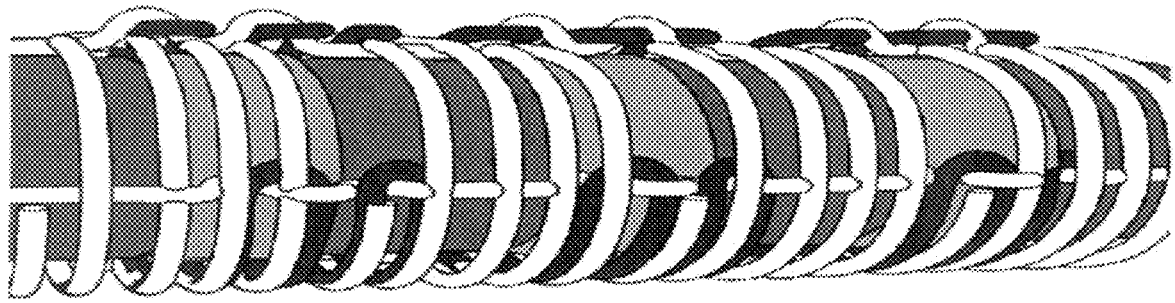

Reference is now made to FIGS. 14*a*-14*d* illustrating insertion of a male mating connector into a female lead proximal end that accommodates the female connection terminals 1442 elastic filaments 1444. Other types of filaments not shown can also be interlocked. As the male connector 1446 is advanced into the structure of the lead, the lead expands due to the elastic filaments used. FIG. 14*d* shows that each male connection terminal in the male connector 1446 is connected with appropriate female terminal 1442 while the structure at the proximal lead end keeps squeezing on the male connector and thus supplying a more reliable electrical connection between the male and the female connectors.

In certain embodiments, a bulk material can form an electrode. The bulk material can be deposited during manufacturing of the electrode using any method, e.g. braiding, knitting, weaving, interwinding, entangling, meshing, or any combination thereof. In certain embodiments, the deposited material is a bulk of material that contains a second compound that upon triggering forms a desired porous material. In other embodiments, the deposited material is a polymeric isolated material that can be deposited in areas that establishes an end of an electrode thread. In a post treatment of the electrode, e.g. radiation, temperature change, adding a cross linker, etc., the polymer is forced to capture exposed conductive threads of the electrode so as to isolate them from the environment. Optionally, the deposited material comprises threads or filaments.

Figure 10D:
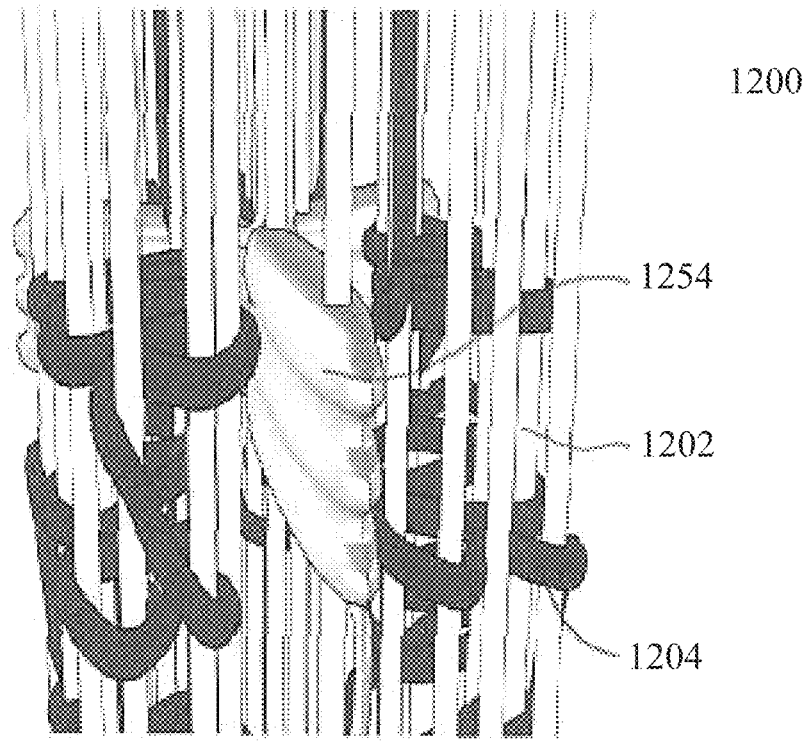
Figure 10E:
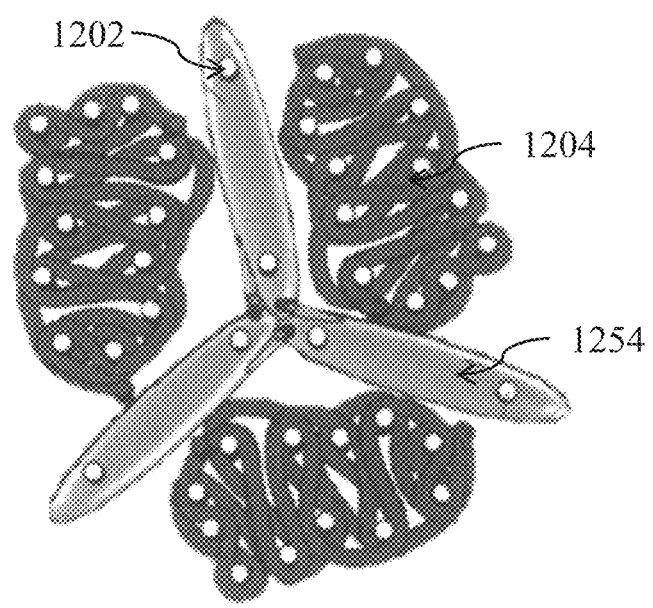

Reference is now made to FIGS. 10*d*-10*e* illustrating cross sectional and side views of the functional filaments of FIGS. 10*a*-10*b* after post treatment. The interlocked electrode lead 1200 shown in FIGS. 10*a*-10*b* may be provided with electrodes 1204 between which functional filaments 1254 such as filaments made of a polymer that can be melted. Both types of filaments of threads are interlocked within a structure of vertical filaments 1202. Other filaments can be incorporated within the structure. After the structure of the electrode lead is finalized, the electrode lead is subject to post treatment such as heat, radiation, etc., that changes the state of the functional polymeric filaments to become a melt that holds together the elements that were interlocked with it. FIGS. 10*d*-10*e* depict the formation of insulation areas inside the lead or electrode body, which can, e.g., separate between conductive areas. One of the ways to accomplish this is by using polymeric filaments arranged and interlocked inside the lead body as to form a separation barrier between different lead areas. These pores and spaces formed inside the interlocked barrier could be closed by a post process over the electrode lead, for example applying enough heat as to melt and reflow these filaments in order to close gaps formed within the interlocked structure. These filaments can be designed to melt in a temperature that is less than the temperature threshold for the reflow or corruption of all the other components and raw materials of the lead.

Figure 15A:
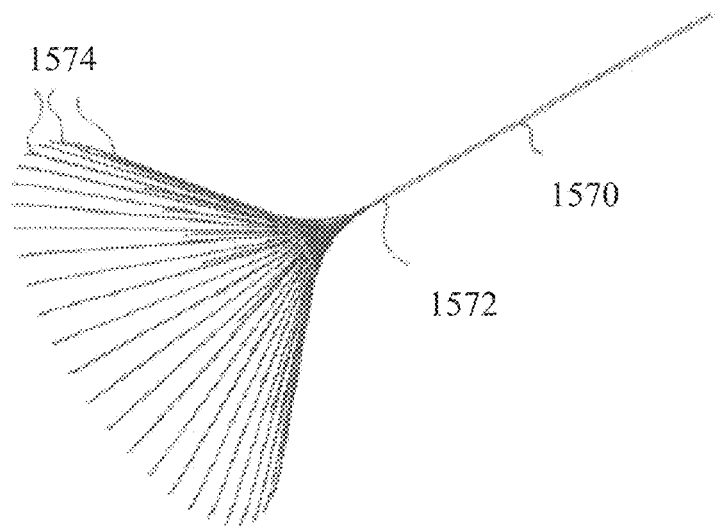
FIGS. 15a-15e illustrate various possibilities of a bundle of threads exposed in a predetermined architecture.

In certain embodiments, the present invention provides a method of forming a lateral extension of exposed conductive filaments that can act as an electrode in an electrode lead. FIG. 15*a* illustrates an electrode contact fabricated from a single thread or filament that splits into several filaments. A single thread or filament 1570 is made of a conductive core coated with a nonconductive material. In a predetermined point 1572 on the thread filament 1570, the conductive material is being exposed and split into a plurality of filaments 1574 that comprises the electrode that can be integrated within an electrode lead.

In other embodiments, a bundle of filaments can be extended in a predetermined area and exposed therein so as to form an electrode contact. As seen in FIGS. 15*b*-15*e*, a bundle of filaments 1550 in which the filaments are made of a conductive core coated with nonconductive material is held together. In a predetermined zone/area of the bundle 1552, the bundle is allowed to be loosened and the filaments are allowed to be laterally extended. In this area 1552, the nonconductive coating is removed from the conductive core of the filaments so that the loosened filaments act as electrode contacts. Such bundles may be integrated within an electrode lead that is fabricated using methods such as braiding, knitting, weaving, interwinding, entangling, meshing, or any combination thereof. The integration of at least one such bundle into an electrode lead can be implemented into any possible electrode lead architecture, e.g. as those in FIG. 9. One example of forming such lateral extension of filaments in a bundle 1550 is to press the bundle from both sides of the lateral extension towards each other so that the filaments are forced to extend aside in this loosened area.

Figure 15B:
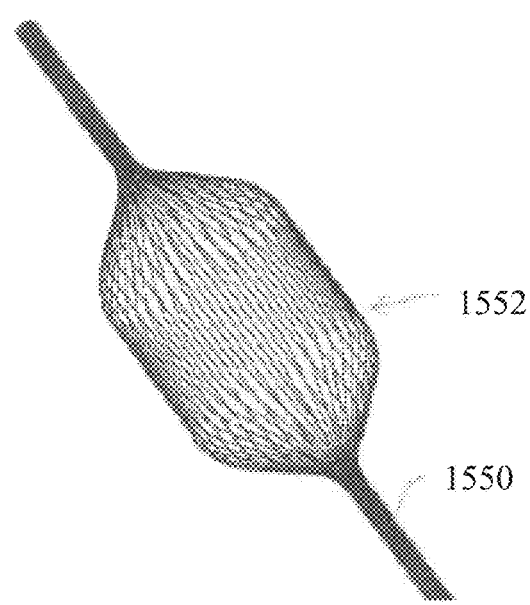
Figure 15C:
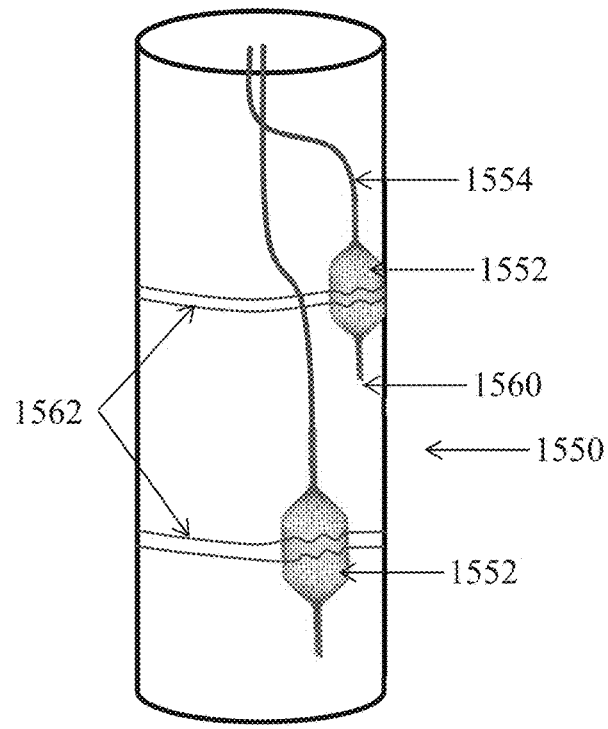

FIG. 15*c* schematically illustrates an electrode lead 1550 with integrated electrode contacts of FIG. 15*b*. As illustrated, the electrode lead 1550 incorporates at least two electrodes 1552, wherein the electrodes are electrically connected to an electronics module (not shown) through the bundle of threads 1554 that is isolated or through a single relatively thick isolated thread. The interlocked structure of the electrode lead 1550 is represented by filaments 1562. Notably, only a few filaments are presented in the drawing so as to clearly show the structure of the electrode lead, however, it should be understood that this is only a representation and the electrode lead is made of a great amount of interlocked filaments.

In certain embodiments, the end of the electrode contact 1560 is coated with an isolating material, which may be deposited by any suitable method.

In certain embodiments, the electrode provided herein comprises a volumetric-contact occupying a predetermined volume. In alternative embodiments, the volumetric-contact has a porous structure with multiple conductive surfaces therein, for facilitating delivery of an electric signal to or from a fluid environment in the vicinity of the electrode contact via the multiple conductive surfaces within the volume of the volumetric-contact. Integrating such volumetric contacts in an electrode lead to within the disclosed architectures or other architectures even further increases the contact surface area of the electrode, by which increase the charge capacity.

Figure 15D:
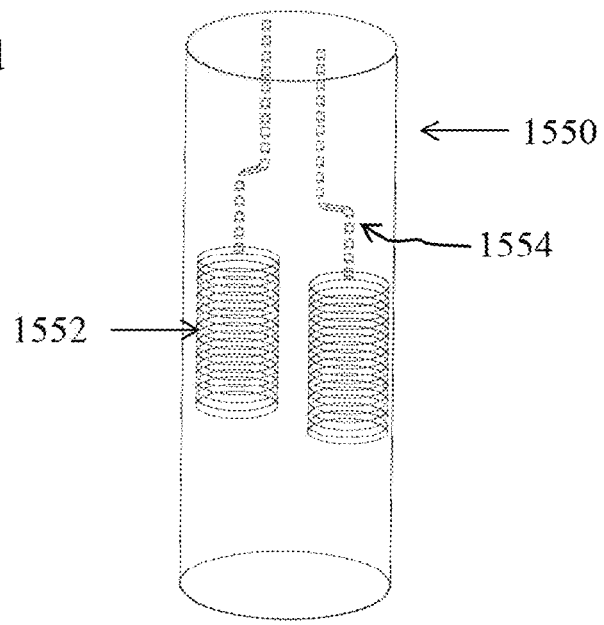
Figure 15E:
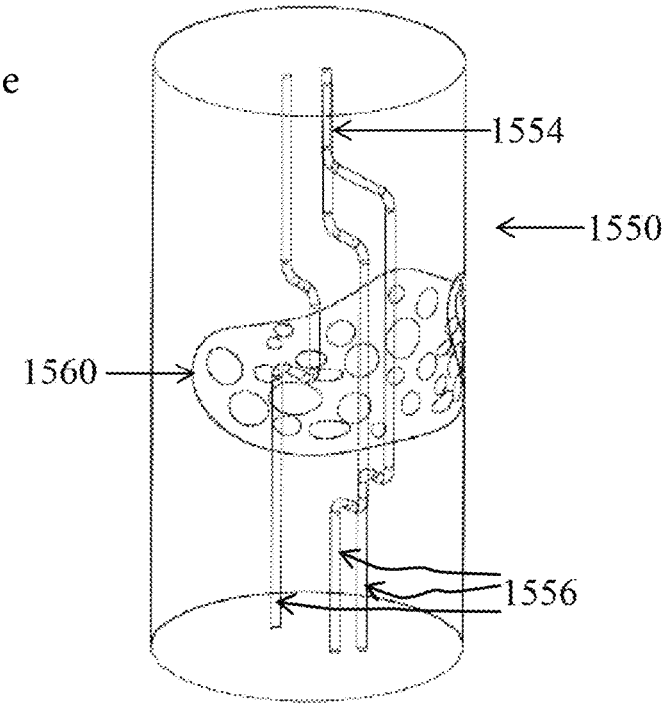

FIGS. 15*d* and 15*e* illustrate electrode lead with integrated sponge-like or porous electrode, respectively, according to an exemplary embodiment. FIG. 15*d* shows a sponge-like bulk 1552 made of conductive material integrated within an electrode lead 1550, wherein the sponge-like bulk 1552 acts as an electrode that is electrically connected to a conductive wire 1554 electrically connected to an electronics module (not shown). The sponge-like bulk 1552 can be integrated within an electrode lead by incorporating it, e.g., within the filaments 1556 that make the electrode lead structure. The bulk 1552 can be integrated within the structure or the electrode lead or independently. FIG. 15*e* illustrates electrode lead with integrated porous 1560 electrode according to an exemplary embodiment. In a specific embodiment, the porous bulk 1560 has relatively large surface area that can act as active surface area for transmitting signals.

In accordance with specific aspects of the invention, and due to the unique architecture of the lead, it is possible to fabricate an electrode lead having a volume that employs volume sharing. An electrode is provided with a first contact having a structure occupying a defined space (surface or volume) to form conductive surfaces with a plurality of voids therein, and a second contact with at least one conductive surface, being at least partially interlocked with the first contact to occupy at least one of the plurality of voids within the structure of the first contact, such that there is no direct electric contact between the at least one conductive surface of the second contact and the plurality of contact surfaces of the first contact.

Figure 16A:
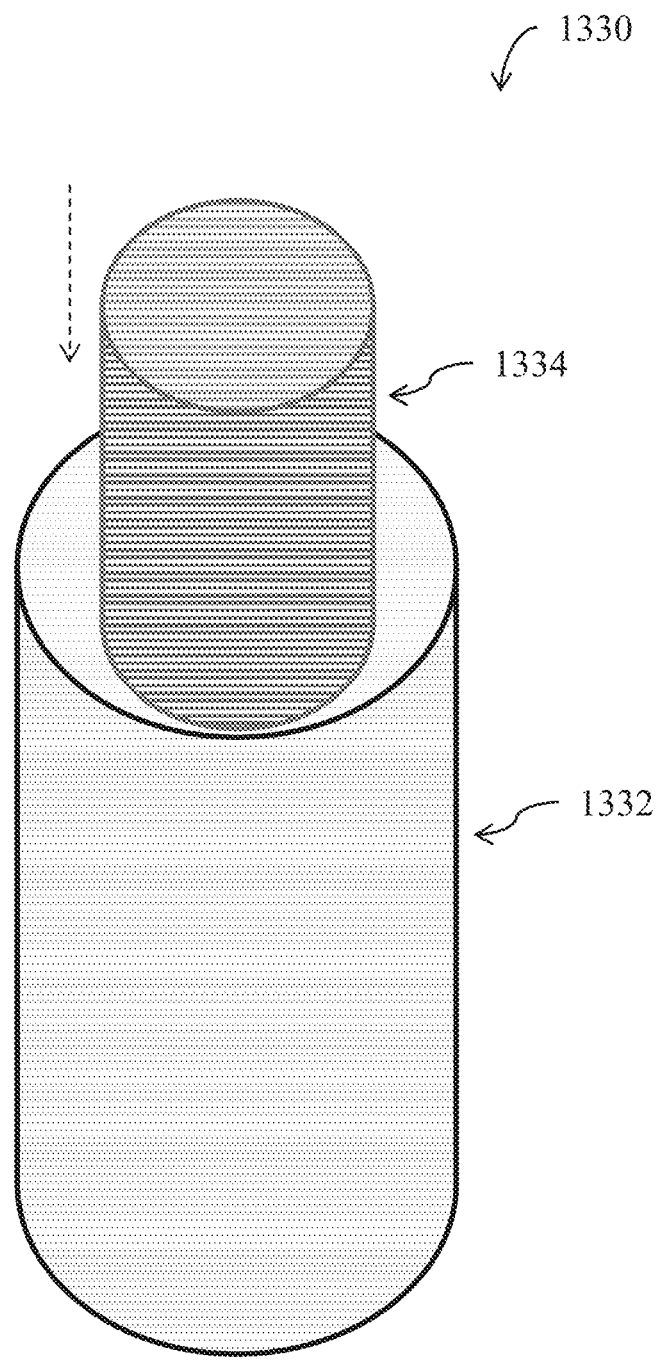
FIGS. 16a-16c schematically illustrate electrodes with an inner layer and an outer layer, according to some embodiments.

Reference is now made to FIG. 16*a*, which schematically illustrates an electrode 1330 with an inner layer 1334 and an outer layer 1332, according to some embodiments. In certain embodiments, outer layer 1332 and inner layer 1334 are formed together in the same process, or alternatively, independently formed and assembled/introduced at a later stage. In other embodiments, inner layer 1334 and outer layer 1332 may be structurally bound with one another, or structurally independent.

In certain embodiments, an electrode of the invention has an aperture made on the surface thereof, or a cavity within the volume thereof. In other embodiments, an aperture on the surface or outer layers of an electrode is utilized for introducing objects from within the structure of the electrode and protrude outside the outer surface to reach certain location, for example within the body of a subject, or to achieve certain functionality, such a contact shape or positioning, or for example to achieve an anchoring of the electrode at a desired location/position after insertion.

Figure 16B:
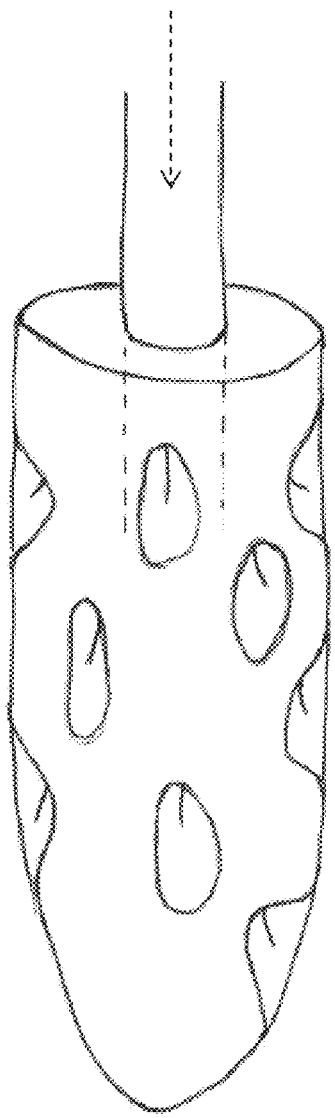
Figure 16C:
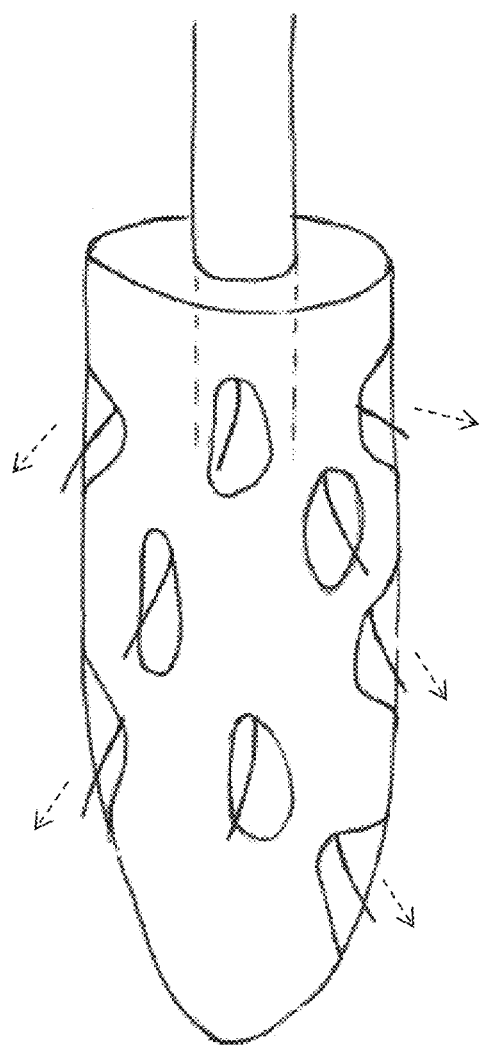

As seen in FIGS. 16*b*-16*c*, the apertures could be created by the same interlocking process, as well as an inner structure, e.g., micro electrodes could be created inside the internal moving part protruding inside the aperture in the outer layer and in some cases not protruding outside the external layer. Such that when desired, the inner structure can move inwardly while forcing the microelectrodes to move inside the aperture and protruding in micro-steps into the tissue, such that the apertures form guides guiding the protruding internal elements through the outer layer and into the tissue. In other cases, other leads built within internal layers can protrude through the aperture and into the tissue. One of the advantages of this structure is its ability to control the exact protrusion pace of the internal layer protruding elements into the tissue, in addition to its ability to retract all these elements back into the lead structure when desired so that no protrusion of internal elements is protruding through the external surface of the lead. Another advantage of using the above mentioned structure is its ability to protect the electrodes' leads during insertion of the electrode lead into the final implantation place: after insertion of the electrode into place, the inner elements (which are the actual electrodes or other sub-leads that have electrodes) are pushed forward into the tissue in fine steps. Moreover, said structure provide an additional mean for further fine adjustments of the inner electrode after implantation of the electrode in place, e.g. in cases where a more ideal stimulation or monitoring position in the tissue is desired. In addition, if a need to explant the lead is desired, the inner structure is first adjusted to force the protruded parts to retract into the lead structure not leaving any protrusion beyond the outer layer, and afterwhich the lead is explanted without injuring the tissue during extraction.

In certain embodiments, the electrode lead of the invention comprises multiple layers, such that when the inner layer moves, i.e. extending outwardly from the outer layer, electrode contacts or another structure(s) residing at the inner layer protrude from the outer layer. Alternatively, movement of a layer enables electrode contacts or another structure(s) residing at the inner layer, to protrude from the outer layer through predetermined holes within said outer layer. This feature can be used, e.g., at the connector of the electrode to connect it to another device.

Figure 17A:
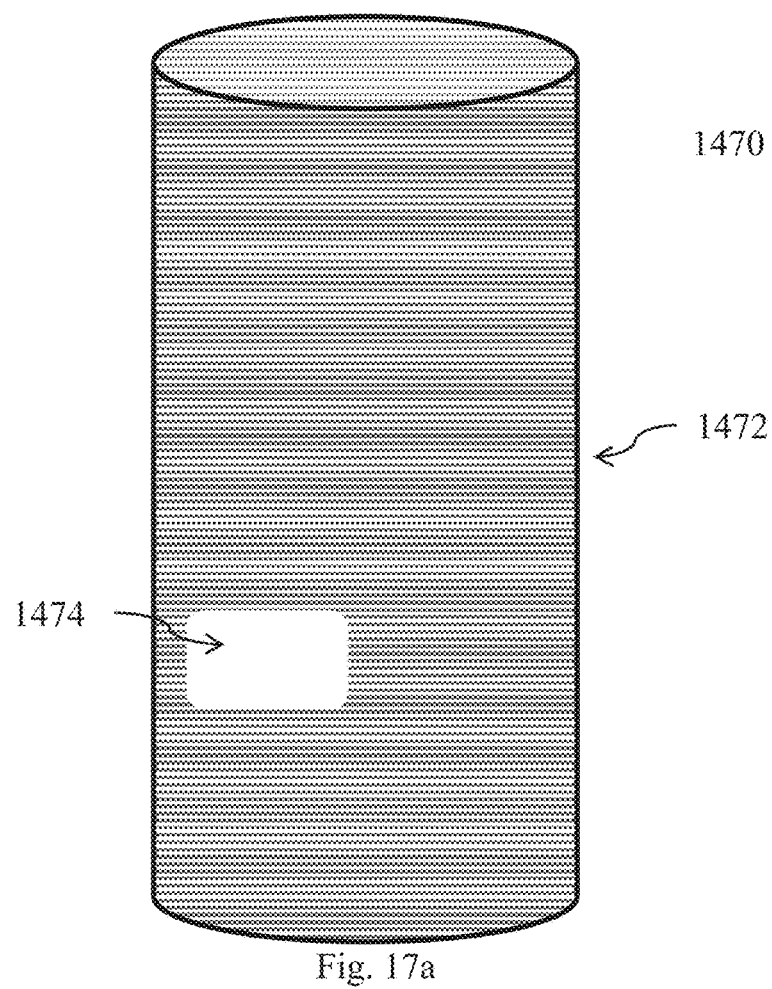
FIGS. 17a-17c schematically illustrate an electrode with an aperture in the outer layer thereof, according to some embodiments.
Figure 17B:
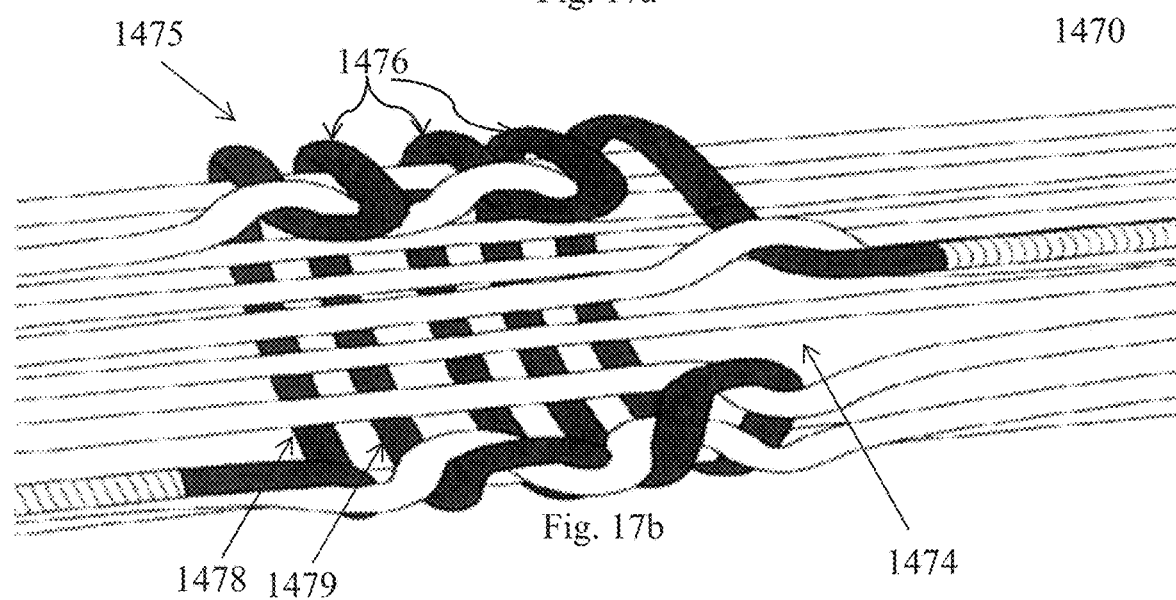

Reference is now made to FIGS. 17*a*-17*b*, which schematically illustrate an electrode 1470 with an aperture 1474 in its outer layer 1472, according to some embodiments. In certain embodiments, an aperture 1474 may be formed for structural and/or functional purposes that are determined by the shape thereof. Such functional properties may be formation of a cavity within the body of the electrode for increasing flow of body fluids therein, e.g., in case of a contact within the volume of the electrode. Alternatively, such cavity or aperture may be formed to achieve certain directionality of electric and or magnetic field. In certain embodiments, aperture 1474 may be utilized for introducing objects, tools, structures or the like to the external surrounding environment of the electrode 1470.

FIG. 17*b* further illustrates an example on how it could be possible to create volume areas that are EMI (electromagnetic interference) compatible. The conductors inside each of the volumetric contacts could assume a track that increases immunity of the electrode area to EMI interference, e.g. does not coil all the way around the electrode circumference, or does not form loops, but rather is weaved/braided/interlocked in a way that have areas of the conductor laid in a configuration that cancels other areas in the same conductor. This way, when inside a magnetic field, opposite configurations will be induced by opposite electrical currents thus cancelling each other's contributing to substantial decrease electromagnetic interference. FIG. 17*b* shows a conductive mass that can be an electrode contact or a connection terminal 1457 that have an exposed metallic inner layers 1476, due to a certain necessity to fold the filament, the folding is configured such that no loop created by the folding filament is opposite in its direction to the other one, thus creating electromagnetic interference immunity. As seen in FIG. 17*b*, filament 1478 is foiled once clock-wise and then counter-clock-wise 1749 so that each fold oppose the other. These configurations could also be assumed to any part in the electrodes lead when and where it is desired to create electromagnetic compatibility or in order to cancel electromagnetic induced currents into filaments with metallic cores.

Figure 17C:
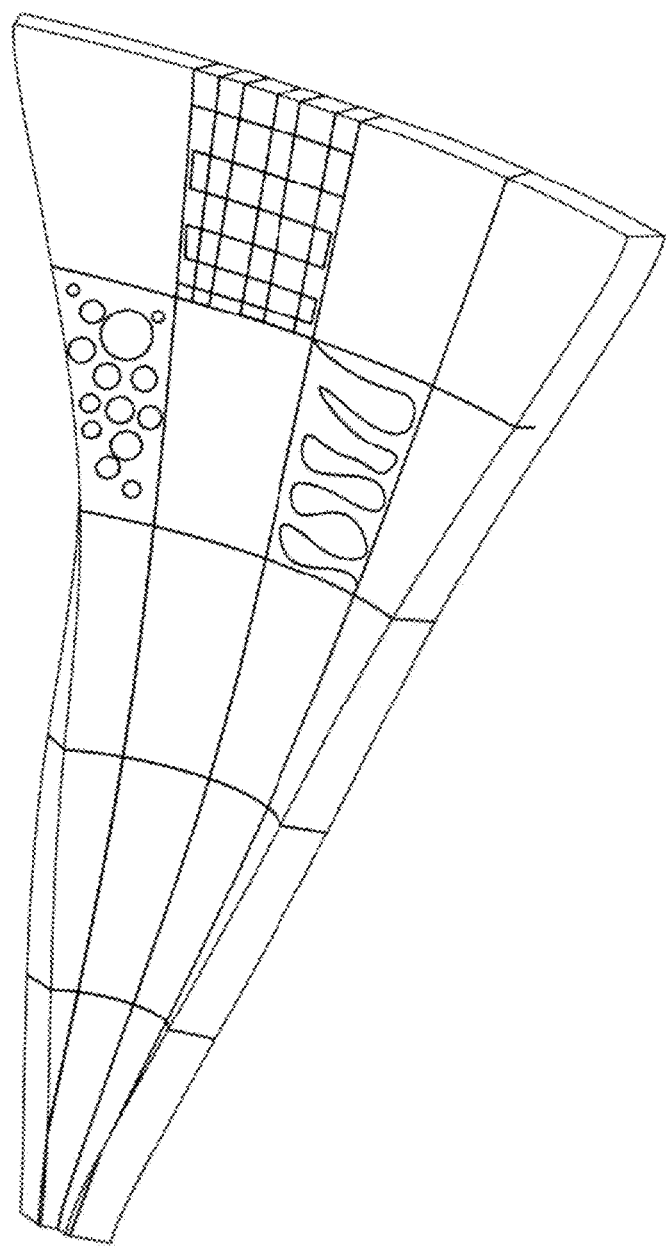

FIG. 17c shows an electrode that have a more planar structure, having incorporated inside it conductive areas (black color) according to the different aspects of the invention. Such an electrode structure can also be fabricated using the methods described herein and having similar features as described and mentioned herein.

The present invention further provides a thread interlocking machine, configured to carry multiple threads, and interlock them such that a thread may be positioned to function as a warp at certain times/locations, and as a weft at others.

In certain embodiments, a thread is held and provided to interlocking by a thread carrier, which is configured to hold the associated thread at a certain tension or tensions, and to be released controllably for forming the interlocked structure. In specific embodiments, the carrier is configured to be movable in at least two directions: a vertical direction—when used in forming a warp within the structure, and a horizontal direction-when used in forming a weft within the structure and/or for relocating the horizontal position thereof to form a warp at a different horizontal position. In other specific embodiments, the vertical movement of carriers is used in determining the interlocking pattern, while the horizontal movement of the carrier(s) is used to create a beat in the structure.

In certain embodiments, the thread interlocking machine of the invention includes a plurality of vertical tracks to facilitate vertical movement of several carriers, and at least one horizontal track to facilitate horizontal movement of at least one carrier at a certain time. In specific embodiments, the carriers are configured to controllably change their movement pattern by leaving a vertical track to move in a horizontal track, and also to move from the horizontal track to a vertical track.

In certain embodiments, the threads are held and controllably provided at one end by the carriers, and at the other end thereof at a base location where the interlocking of the threads takes place to form the structure.

Accordingly, the present invention provides a thread interlocking machine for fabricating an interlocked thread electrode, comprising: (a) a plurality of thread carriers, each configured to hold a desired thread, at least one thereof having a conductive core coated with a non-conductive material; (b) at least two cross-track segments, each segment having: (i) a vertical track, defining a vertical movement range of a thread-carrier, and (ii) a horizontal track, defining a horizontal movement range of a thread-carrier (shuttle), such that said vertical track and said horizontal track intersect along the longitude thereof, facilitating an alteration of movement of a thread-carrier between said vertical track and said horizontal track, and the cross-track segments are arranged horizontally to facilitate a movement of a thread carrier from a horizontal track of one cross-track segment to a horizontal track of another segment; (c) a thread base, configured to hold a plurality of threads at a distal end thereof, such that the threads are strained from said thread carriers to said thread base; (d) at least one actuator for moving said plurality of thread carriers and optionally said thread base; (e) at least one means (laser) for exposing said conductive core of said filament(s); and a control unit.

In certain embodiments, the thread interlocking machine of the invention is a radial weaving machine.

In certain embodiments of the thread interlocking machine of the invention, the vertical track comprises a plurality of pre-defined positions for anchoring said thread carriers.

In other embodiments of the thread interlocking machine of the invention, the actuator moves each thread carrier, independently from other thread carriers (from one position to another).

In certain embodiments of the thread interlocking machine of the invention, the control unit is designed to: (a) receive data regarding the length of the electrode and the weaving pattern and locations of the exposed filaments, (b) control the movement of the thread carriers from one station to the other; (c) control the movement of the shuttle; and (d) control the activation of said means for exposing the conductive core of said filament(s).

In specific embodiments, the electrode fabricated by the thread interlocking machine of the invention is an interlocked thread electrode of the invention.

In certain embodiments, the present invention provides a cross-track segment configured for facilitating a controlled movement of a thread carrier in the thread interlocking machine of the invention, comprising at least two cross-track segments, each segment having: (a) a vertical track, defining a vertical movement range of a thread-carrier, and (b) a horizontal track, defining a horizontal movement range of a thread-carrier, such that said vertical track and said horizontal track intersect along the longitude thereof, facilitating an alteration of movement of a thread-carrier between said vertical track and said horizontal track, wherein the cross-track segment is further configured to be arranged horizontally with another cross-track segment, to facilitate a movement of a thread carrier from said horizontal track of the cross-track segment to a horizontal track of the other cross-track segment.

Figure 18:
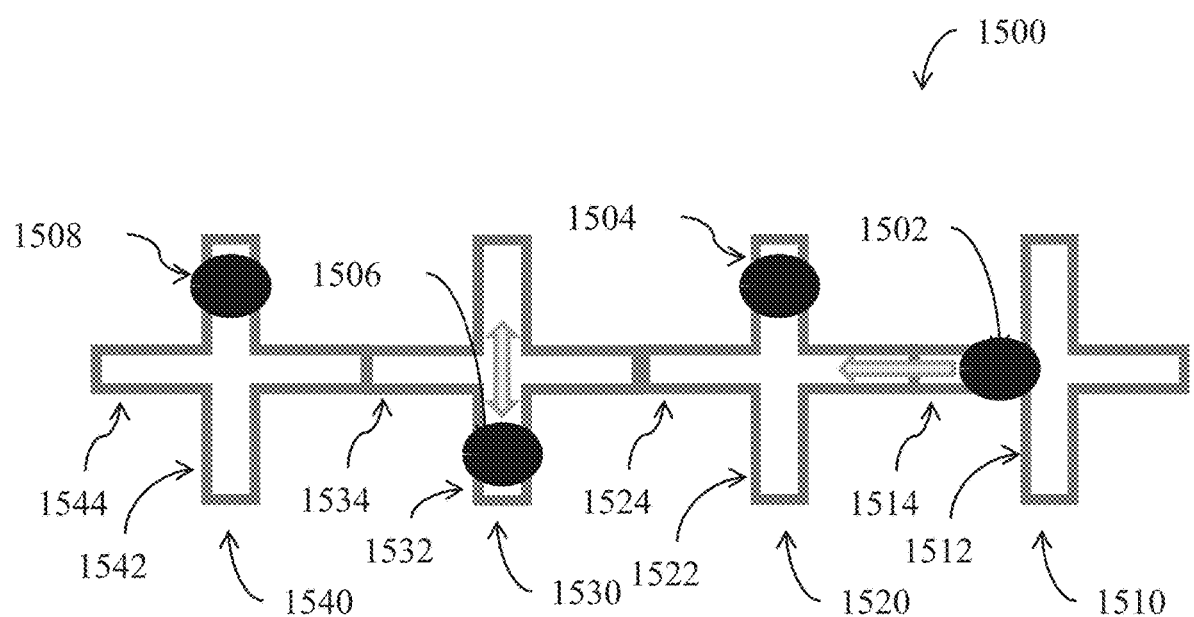
FIG. 18 schematically illustrates a multi-segment system for thread interlocking, according to some embodiments.

Reference is now made to FIG. 18 schematically illustrating a multi-segment system 1500 for thread interlocking, according to some embodiments of the invention. As illustrated, the system 1500 may include a first segment 1510 with a first vertical track 1512 and a first horizontal track 1514, a second segment 1520 with a second vertical track 1522 and a second horizontal track 1524, a third segment 1530 with a third vertical track 1532 and a third horizontal track 1534, and a fourth segment 1540 with a fourth vertical track 1542 and a fourth horizontal track 1544 (etc.). In specific embodiments, the segments are structured such that first—1514, second—1524, third 1534, and fourth-horizontal track 1544 are aligned to form a continuous or semi continuous horizontal track to allow for a carrier horizontal movement therein. According to some embodiments, a first carrier 1502 is illustrated moving in the horizontal direction, functioning as a weft, while a second—1504, a third—1506, and a fourth-carrier 1508 are positioned within second—1522, third—1532, and fourth-vertical track 1542, respectively, at certain locations, either above or below the horizontal track, functioning as warps. In specific embodiments, within each segment, the intersection of the horizontal track and the vertical track is configured to allow transitioning of a carrier from the vertical track to the horizontal track, and vice-versa.

In certain embodiments, a carrier may include actuators for moving it within a track or between tracks, or alternatively, the machine may include independent actuators configured to be at least at sometimes mechanically and/or electrically/electromagnetically/magnetically associated with a carrier to controllably actuate a movement thereof within a track or a transition thereof between different tracks. In specific embodiments, the thread interlocking machine of the invention may have a horizontal actuator(s) configured to controllably move carriers in the horizontal track(s), and vertical actuators configured to controllably move carriers in the vertical tracks. In yet other specific embodiments, the vertical and horizontal actuators are configured to allow for transferring the mechanical/electrical/magnetic connection/association of carriers therebetween. In specific embodiments, a horizontal actuator has one form of connection/association with carriers, while a vertical actuator has a different form of connection/association with carriers. In specific embodiments, the horizontal actuator (interchangeably referred to herein as shuttle) is configured to form a mechanical connection with carriers, while a vertical actuator is configured to form a magnetic connection with carriers.

In certain embodiments, each carrier further comprises at least one mechanism to change the tension of the thread it holds. In a specific embodiment, this mechanism is an array of springs, each producing a different tension, so that when the shuttle reaches and holds a specific carrier, and connects to it mechanically or electronically; it forces the carrier to switch between different springs thus changing the tension of the thread. In another specific embodiment, the tensioning mechanism is the actual incorporation of the motor/servo inside the carrier, which creates a variable tension on the thread, and is controllable by the machine controller. In other embodiments the means to switch the tension of a carrier can be wirelessly or through other mechanical mechanism that is available at the vertical or horizontal tracks or segments.

Figure 19:
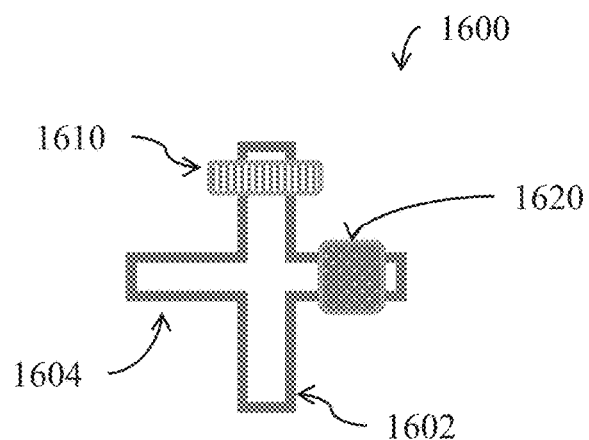
FIG. 19 schematically illustrates a back view of a segment, according to some embodiments.

FIG. 19 illustrates a back view of a segment 1600, according to the invention, which comprises a vertical track 1602 and a horizontal track 1604, where a magnetic actuator 1610 is positioned to move along vertical track 1602 and a shuttle 1620 is configured to move along horizontal track 1602. In specific embodiments, a vertical track may include a station or stations, which are mechanisms to hold a carrier at a desired vertical position along the vertical track while not associated with a horizontal actuator. Advantageously, holding a carrier at a station may allow for the vertical actuator to handle the vertical movement of other carriers while the rest of the carriers within the associated vertical track are positioned in determined locations.

According to some embodiments, one vertical track may be configured to house at least one, at least two or more carriers at a given time. According to some embodiments, at least some of these carriers may be held in position by stations. In specific embodiments, each vertical track is configured to house one, two, three, four, five, six, seven, eight, nine, ten or more carriers at a given time. In other specific embodiments, each horizontal track is configured to house one, two, three, four, five, six, seven, eight, nine, ten or more carriers at a given time.

Figure 20A:
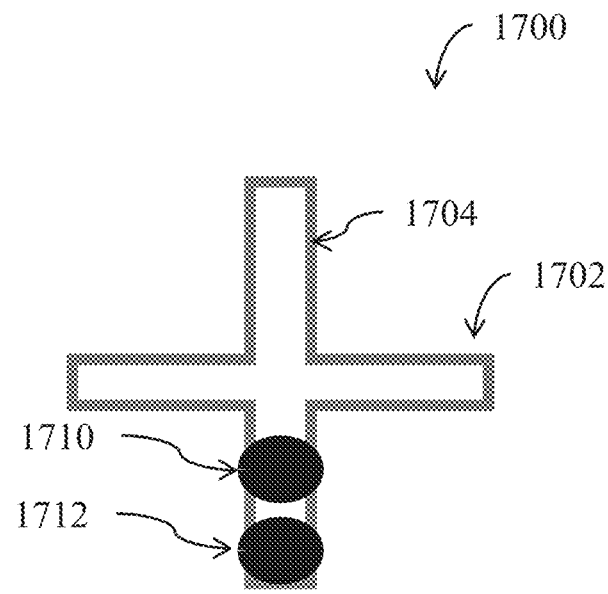
FIGS. 20a-20b schematically illustrate a segment with vertical actuators at different positions, according to some embodiments.
Figure 20B:
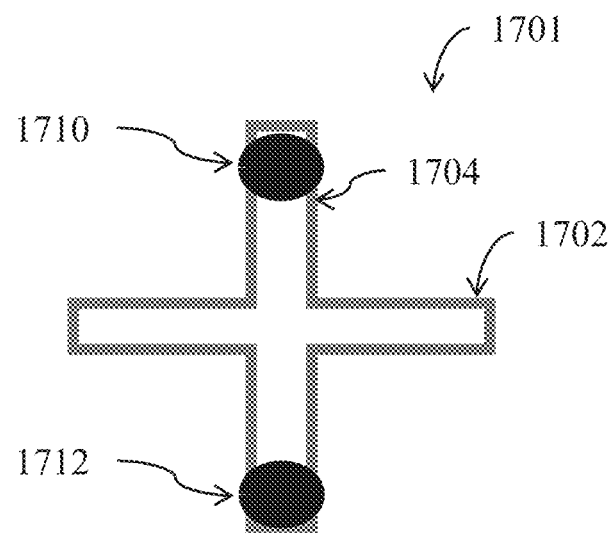

FIGS. 20a-20b illustrate a segment with vertical actuators at different positions, according to some embodiments. FIG. 20a illustrates a segment 1700 with a vertical track 1704 and a horizontal track 1702, wherein a first carrier 1710 and a second carrier 1712 positioned below horizontal track 1702. FIG. 20b illustrates another possible configuration of a segment 1701 having a vertical—1704 and a horizontal track 1702, wherein a first carrier 1710 is positioned above horizontal track 1702, and a second carrier 1712 is positioned below horizontal track 1702.

Figure 21:
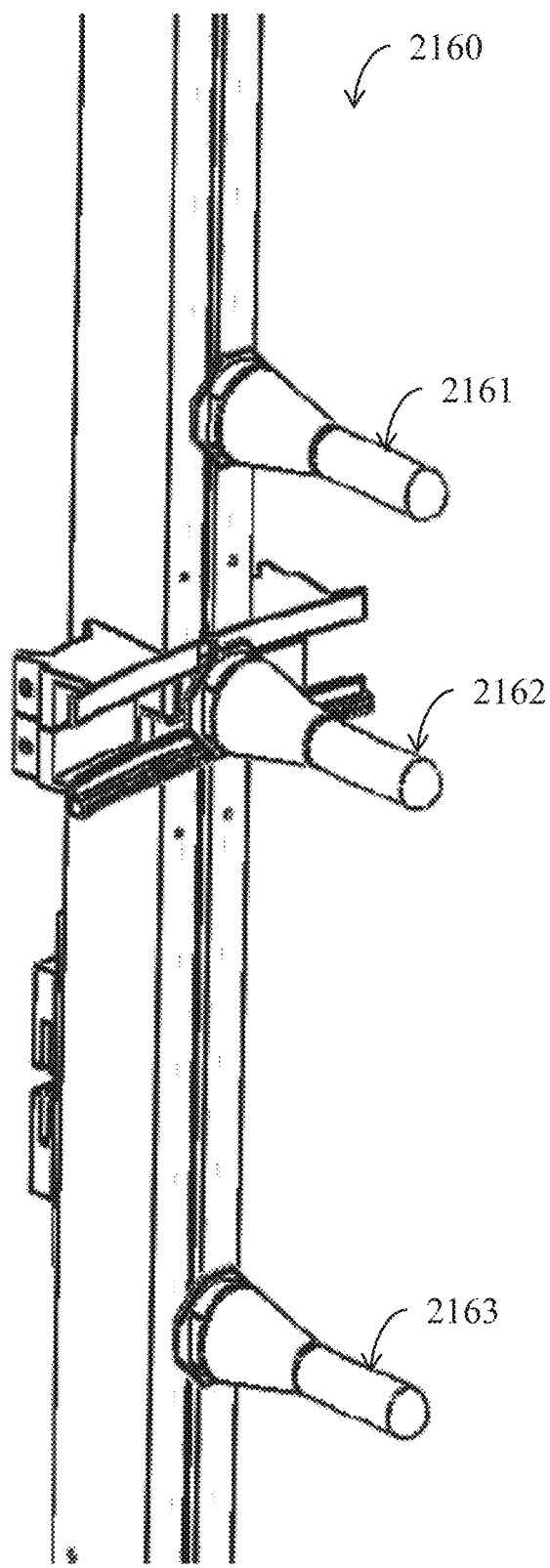
FIG. 21 illustrates a segment with vertical actuators at different positions, according to some embodiments.

FIG. 21 schematically illustrates a single segment 2160 within a thread interlocking machine of the invention, showing three carriers 2161,2162,2163 spread across the vertical track, wherein the middle carrier 2162 is positioned at the vertical track ready to be moved vertically by the vertical actuator(s).

Figure 22A:
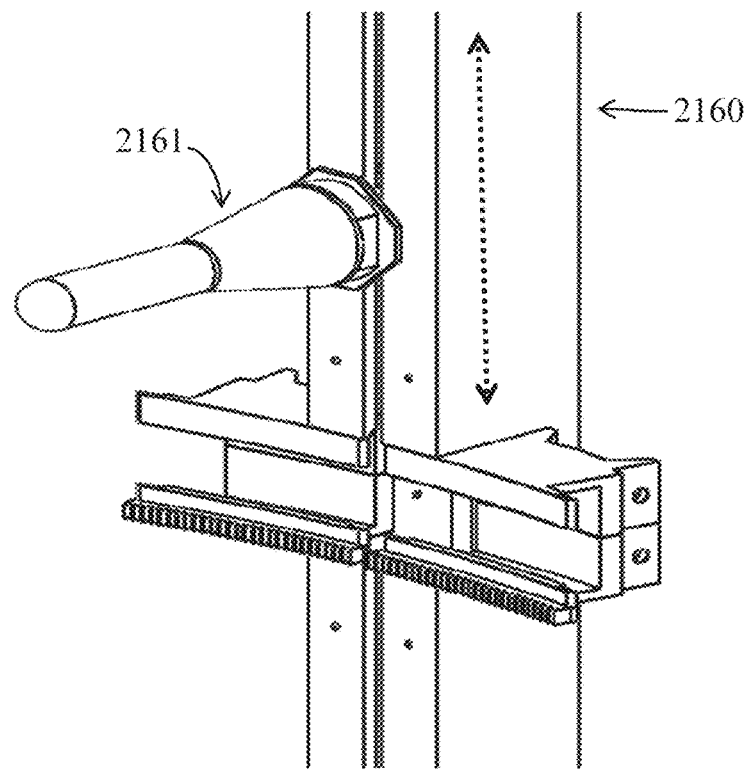
FIGS. 22a-22c illustrate the back side of a segment and the movement of a carrier between horizontal and vertical tracks.
Figure 22B:
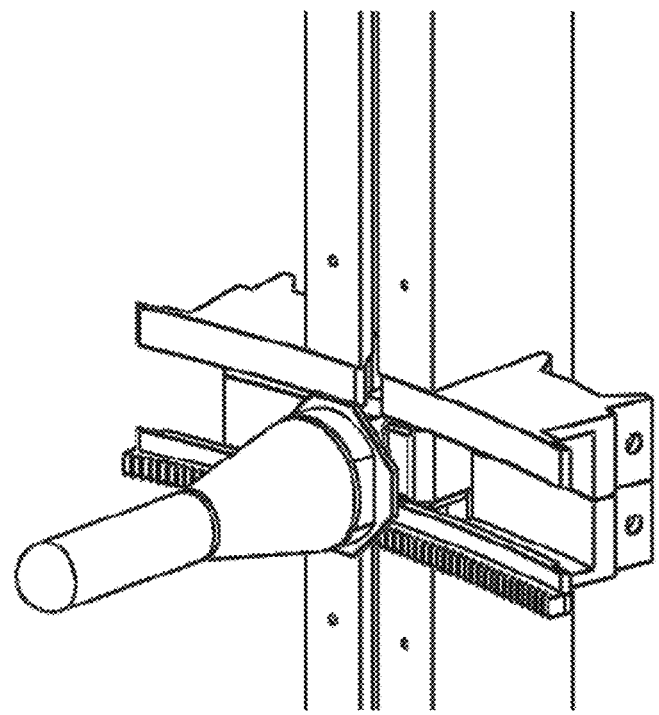
Figure 22C:
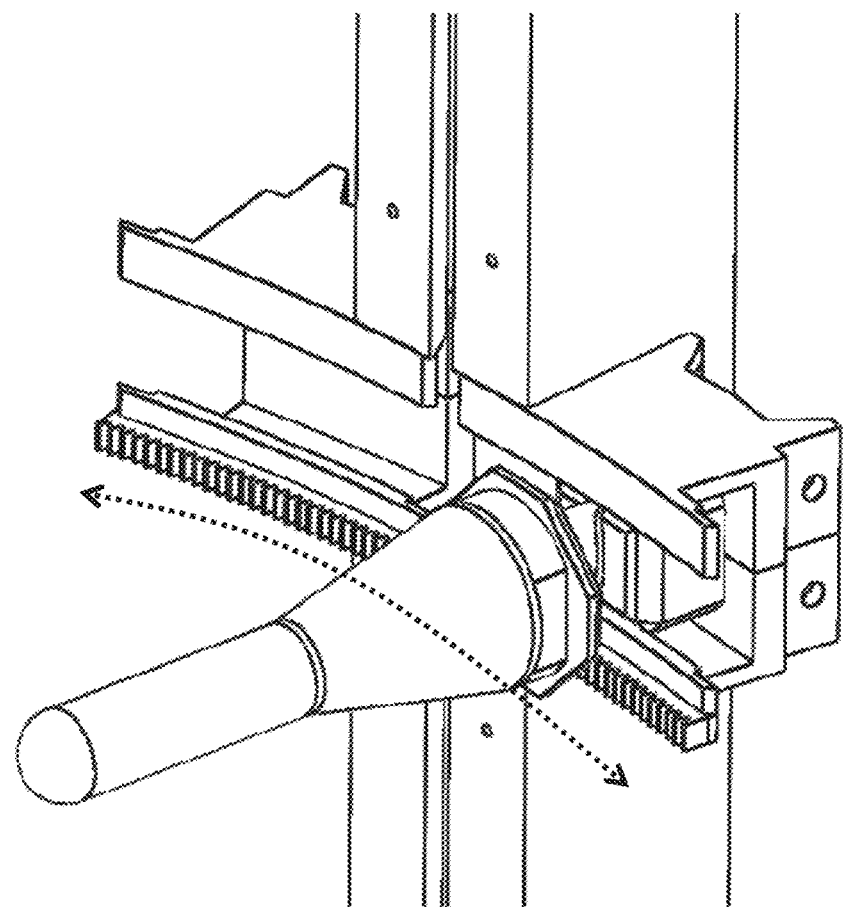

FIGS. 22a-22c illustrate a single segment 2160 of a thread interlocking machine of the invention, wherein a carrier 2161 moves from the horizontal track (FIG. 22a) to the vertical track (FIG. 22b), and then moves vertically (FIG. 22c). In certain embodiments, this movement can be reversed, i.e. from a vertical track to a horizontal track and then horizontal movement.

Figure 23:
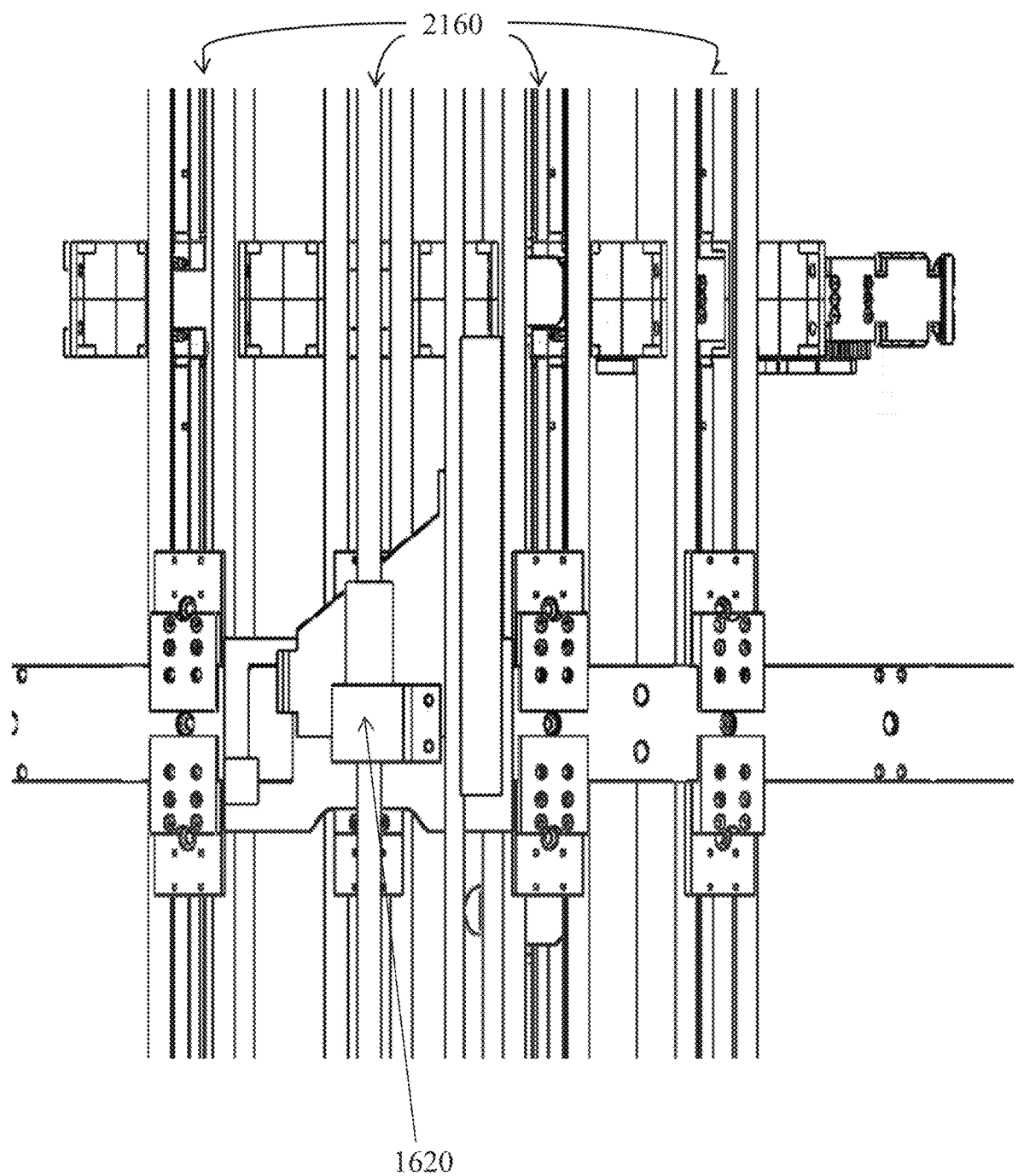
FIG. 23 illustrates the back side of several segments with vertical actuators and shuttle, according to some embodiments.

FIG. 23 schematically illustrates a few parallel segments 2160 in a thread interlocking machine of the invention, illustrating possible locations of the vertical actuators and shuttle 1620, according to a specific embodiment of the invention. In certain embodiments, the segments 2160 are aligned to form a continuous or semi-continuous circular/closed horizontal track, where a carrier may cyclically move along the horizontal track. In specific embodiments, in such a cyclic configuration, the forming location of the interlocked thread (or pint or base) is positioned within, optionally at the center of (FIG. 24b) the circle between the carriers, or along an axis passing within the circle (FIG. 24a).

Figure 24A:
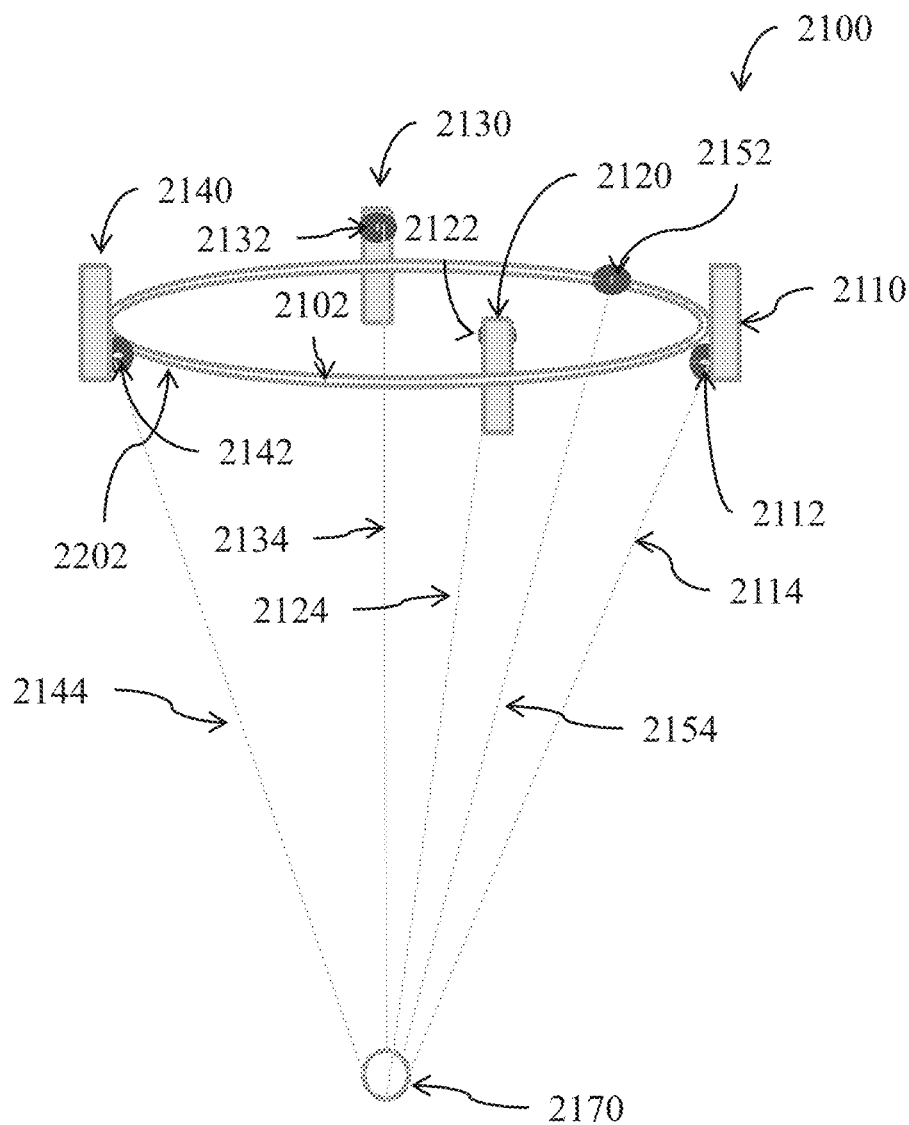
FIGS. 24a-24b illustrate thread interlocking machines.
Figure 24B:
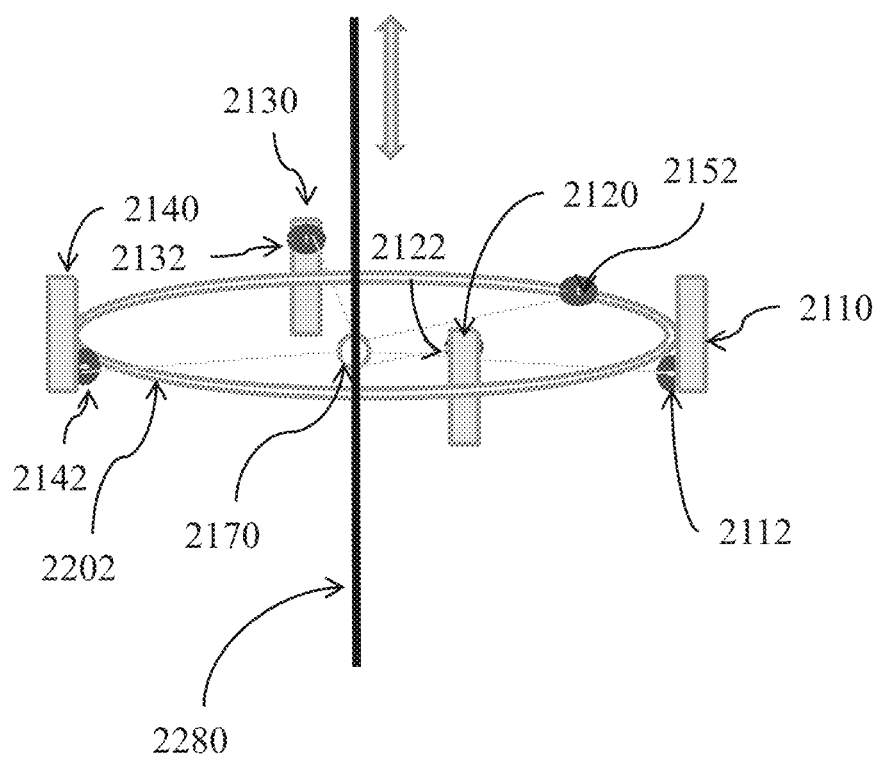

FIGS. 24a-24b illustrate two possible configurations of a thread interlocking machine of the invention: FIG. 24a illustrates a thread interlocking machine 2100 with a lowered base 2170; and FIG. 24b illustrates a thread interlocking machine with a centered base 2270. As shown, the thread interlocking machine 2100 comprises a plurality of segments 2110, 2120, 2130, 2140 arranged in a circle, wherein each segment holds a carrier 2112, 2122, 2132, 2142 while a single carrier 2152 serves as a shuttle (or being held by the shuttle) while moving around on a horizontal track 2202. As explained herein, the carrier serving as a shuttle can be changed with any other carrier, thereby enabling complexed interlocking structures and horizontal and vertical weaving of the same thread.

The core stabilization/weaving point of the electrode within the thread interlocking machine of the invention is the place where the actual weaving/interlocking is taking place. This is a point in the electrode where the weaving threads meet/brought together. In specific embodiments, this point remains at the same height during the whole process of weaving/interlocking the electrode. In an alternative embodiment, this point can be moved up and down in order to create other patterns during weaving or in order to advance or remove the lead from the weaved/fabricated structure.

In certain embodiments, the way this weaving point is held at exact position is by adding new beats of threads onto the core and then pulling the whole structure up by an actuator, such as a core actuator.

In certain embodiments, immediately above the weaving point, the interlocking lead is held inside a tube, and immediately bellow the weaving point the electrode core is held inside another stabilizing tube, thus stabilizing the weaving point. Threads from all the carries meet at the weaving point between the stabilizing upper and lower tubes. this helps in forming a contra-force to the force that is being applied by the tensed threads, and also contributes to the accuracy of the fabricated structure.

Figure 25A:
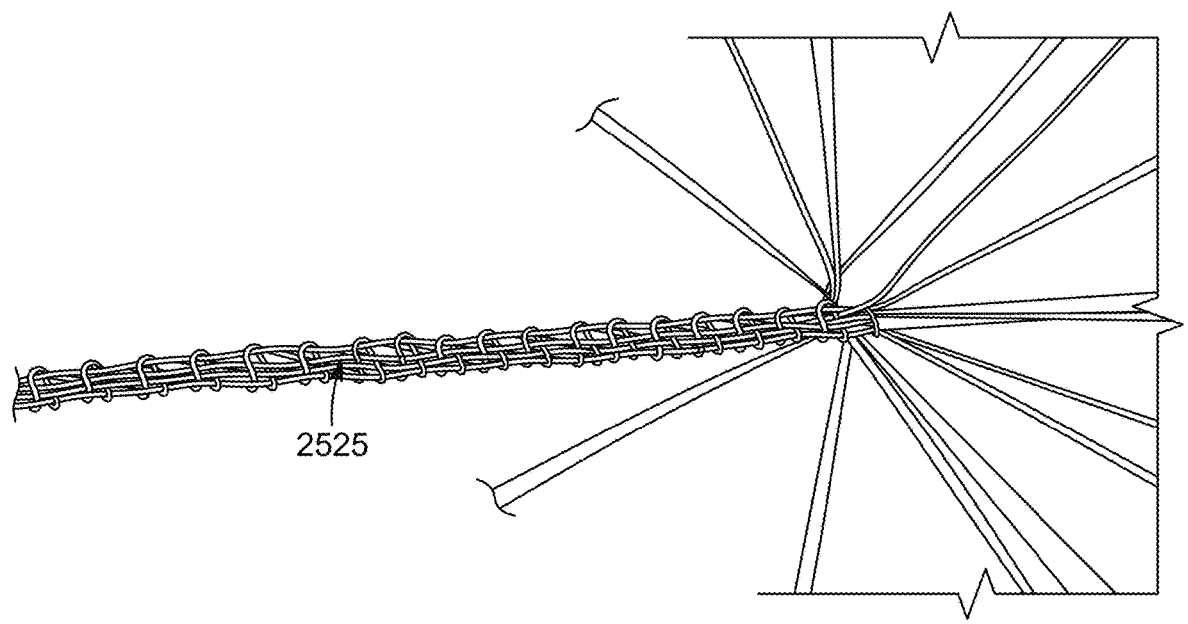
FIGS. 25a-25b are pictures showing actual fabrication of electrodes according to embodiments of the invention.
Figure 25B:
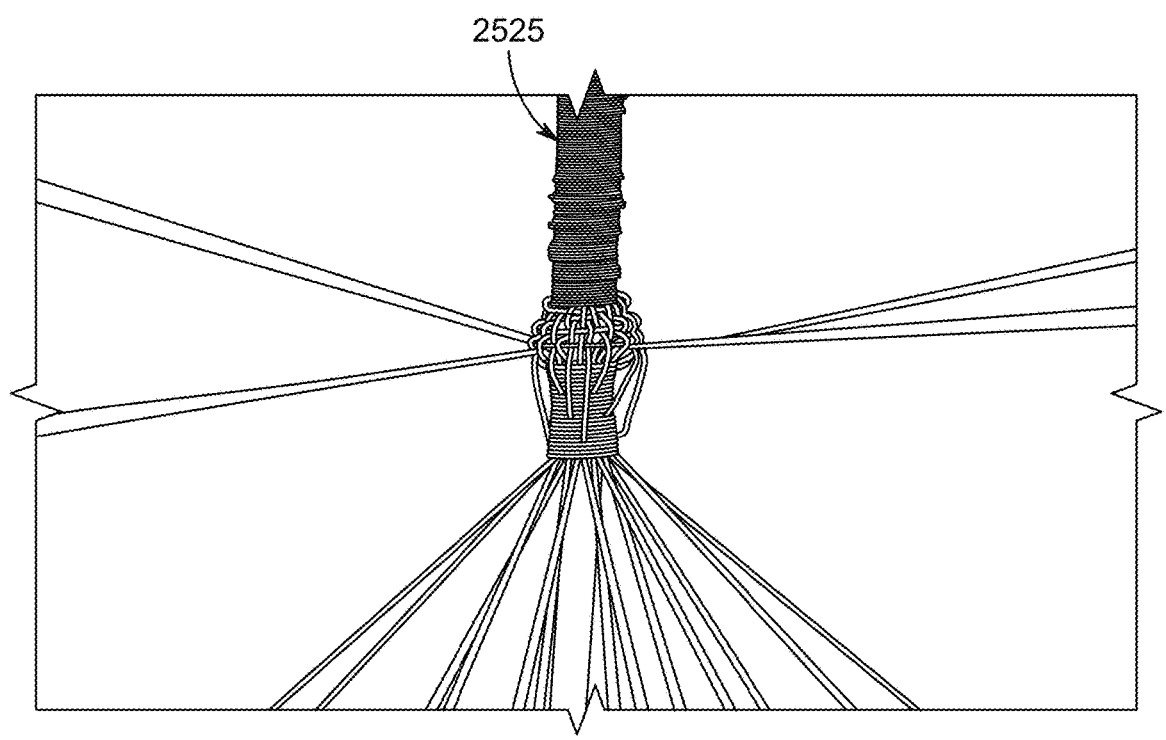

FIGS. 25a and 25b show pictures of real-time fabrication of an electrode 2525 by a thread interlocking machine according to the invention. The pictures were taken during fabrication of an interlocked thread fabricated with a thread interlocking machine having a centered base as illustrated in FIG. 24b.

Figure 26:
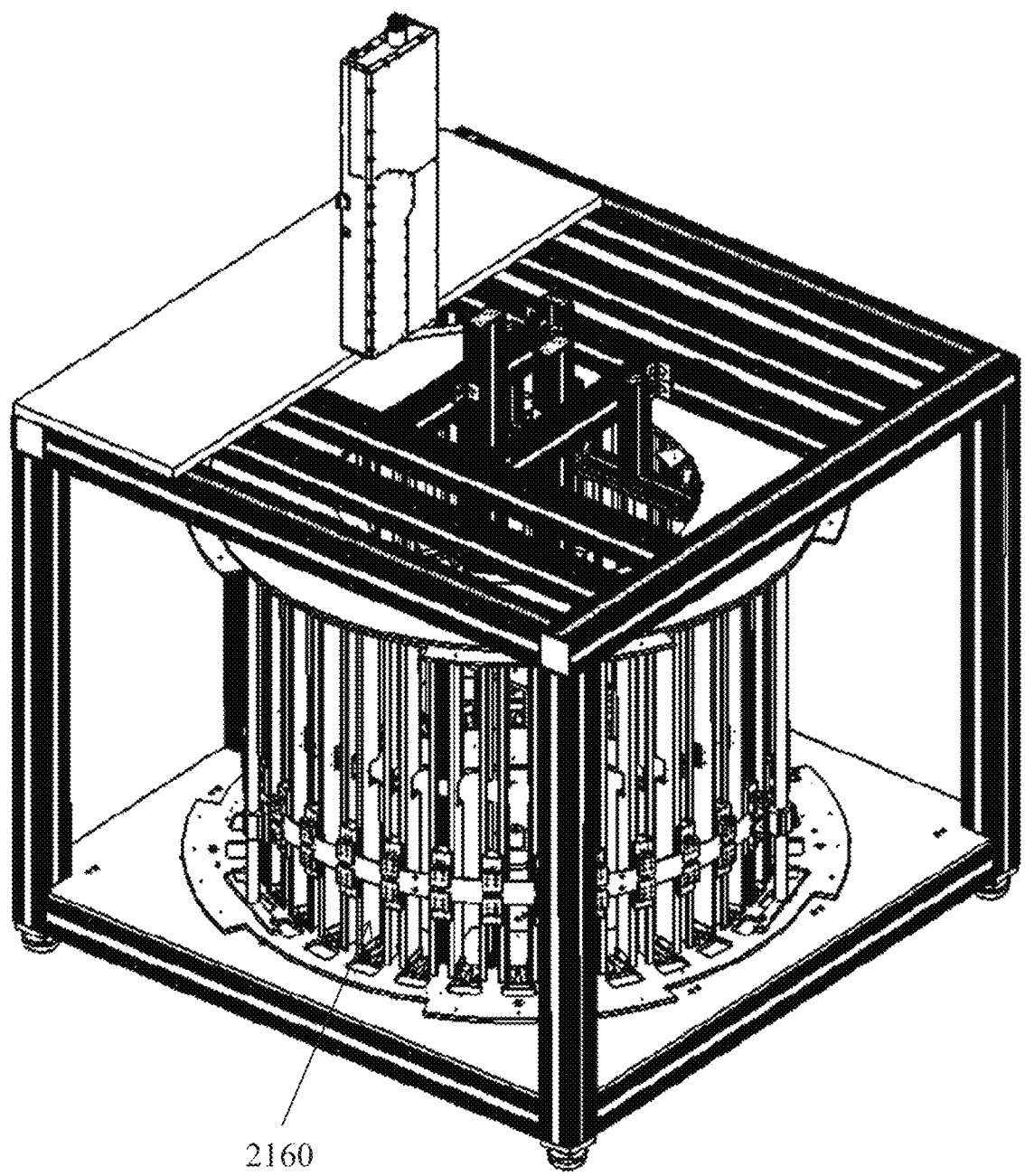
FIG. 26 illustrates one possible configuration of a thread interlocking machine of the invention.

FIG. 26 demonstrates one possible configuration of a thread interlocking machine of the invention, shoeing a circle-shaped arrangement of segments 2160.

The present invention further provides a method for fabricating an electrode by thread interlocking using the thread interlocking machine of the invention, said method is based essentially on fabricating a flat electrode structure while warps are becoming wefts, and vise-versa, in a controlled manner according to a predetermined desired architecture of the electrode.

In certain embodiments of the method and thread interlocking machine of the invention, the changing of warps to wefts, and vise-versa is carried out by changing latitudinal and vertical locations of different carriers (threads), therefore converting a carrier from weft forming thread to a weft forming thread, or vise-versa.

In certain embodiments, each carrier comprises a roll of filament with desired properties, e.g. diameter, material, strength, conductivity, etc.; a thread tension-generator for maintaining a desired tension of the thread; and means for integrating with the shuttle, such as a magnet or electric magnet.

Figure 29:
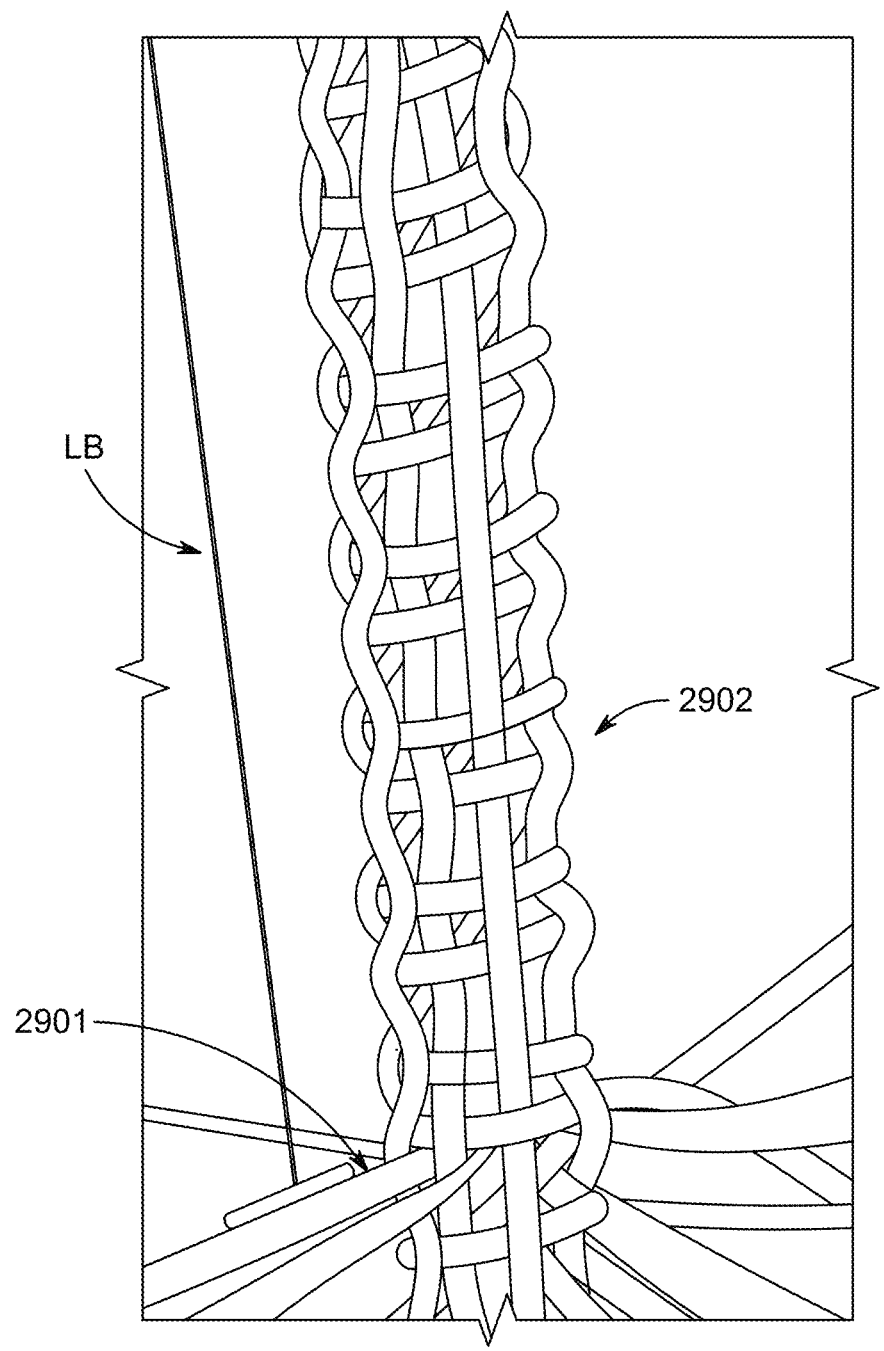
FIG. 29 illustrates the exposure of the inner conductive core of a thread prior to its interlocking into the electrode structure.

One important aspect of the invention is the ability of the machine to expose/functionalize the threads at accurate places while the weaving is in progress. The exposure of the thread insulation could be done in one laser progression, functionalizing a certain length of thread needed to form an electrode contact. This is used before folding/interlocking the exposed thread in 3D into the actual volume contact of the fabricated electrode as shown in FIG. 29. Accordingly, in certain embodiments, the electrode fabrication method of the invention comprises a step of exposing the thread insulation in one laser progression, thereby functionalizing a certain length of a thread needed to form an electrode contact, before folding/interlocking the exposed thread in 3D into the actual volume contact of the fabricated electrode.

As seen In FIG. 29, just before the thread/wire is interlocked into the probe structure, a laser beam LB exposes small regions 2901 in the thread/wire (resolution could be as small as ~7 um). A computer controls when and where the laser conducts ablation of the thread/microwire insulations. After the wire is interlocked, the exposed site functions as a contact area 2902 e.g. as a micro/macro stimulation or recording site. The same method is used to expose larger surfaces for macroelectrode contacts, for example to be used in macro-stimulation.

In certain embodiments, during weaving, ideally before the folding of the thread, or before interlocking the thread into the structure, the thread carrier is brought by the shuttle actuator or by any other means to a position in the horizontal track where the thread is within the laser beam range. Then, the controller instructs the laser to functionalize a portion of the thread that is equal to the total length of the same thread that is needed to create the conductive contact.

In another configuration, the laser functionalizes small portions of a thread at a time each time the thread is brought to the laser range. In this way, the laser beam might be fixed to a certain focal point and the thread is brought to that specific point. Alternatively, e.g. as in the previous configuration, the machine will have the ability to change the focal point/position of the laser and thus able to accelerate the functionalization process. This could be accomplished, e.g., by a galvanometer mirror or XY stage.

Accordingly, in certain embodiments, the thread interlocking machine of the invention further comprises means for functionalizing a thread, i.e. exposing its inner conductive core, such as a laser unit/system capable of exposing a portion of the inner conductive core of a thread according to predefined design of the electrode. In certain embodiments, said laser unit is affixed in place and the portion of the thread that needs to be functionalized is brought in front of the laser to allow removal of the external non-conductive coating. Alternatively, the laser unit is movable and can be brought in front of the portion of the thread that needs to be functionalized. In specific embodiments, the laser unit is movable but the final alignment of the thread portion in front of the laser unit is achieved by dual movement of the laser unit and the carrier/shuttle holding the thread that needs to be functionalized.

In certain embodiments, the intensity of the laser can be modified according to need, e.g. according to the thickness of the non-conductive layer of the thread and/or the physical properties of the inner conductive core thereof.

In another embodiment, functionalization is done through using threads that have insulated coating that is sensitive to certain light wavelength, using a laser with the same light wavelength to functionalize desired parts of the threads, then interlocking the thread into the interlocked lead. A post-processing method could also be used (e.g. electrochemical) on the interlocked lead in order to remove the parts of the coatings that were treated with the laser beam, a process that falls within lithography using laser beam.

After the functionalizing of the thread, the thread is interlocked into the fabricated electrode, thus forming a contact/conductive area at a desired location at the electrode. Accordingly, the process of specific functionalization of certain thread portions and then interlocking the threads into the final electrode enables the formation of isolated contact areas isolated from one another by non-functionalized threads interlocked therebetween, thus enable fabricating special designed electrode according to specific needs, such as desired stimuli locations, physiology of a patient, intensity of the signal to pass through, etc.

In certain embodiments, the thread interlocking machine of the invention further comprises a reed. As evident and explained herein, after a horizontal thread is placed in the fabricated electrode structure, there is a need to push a horizontal portion thereof by a special mechanism up towards the weaving point. This is done while the horizontal wire is tensed. A reed could be made from very fine wires/yarns/sheets that are strong enough and do not bend when pushed against the horizontal wires. In specific embodiments, the reed is not part of the final interlocked lead. In alternative specific embodiments, the reed is part of the threads that are interlocked in the lead. An example of a reed is two wires that are not assembled/interlocked within the structure and attached to a mechanism that can bring them into the fabricated structure in between the interlocked threads. Accordingly, pushing a horizontal thread into and towards the weaving point, then said wires descend down so that they do not interfere with the other threads when weaving continues.

One of the advantages of the thread interlocked machine and system of the invention, is its ability to customize the electrode lead as it is being build. Once the machine finishes building the electrode, it can immediately start building a second electrode. Accordingly, the finished electrode lead is cut from the fabricated structure, while the machine continues building the next electrode lead.

In certain embodiments, the setup of the machine of the invention, including all the carriers, threads, and materials therewithin, is done only once-prior to activation of the machine, or is done when there is a need to replace/recharge the threads as needed.

The present invention further provides a method for fabricating a thread interlocked electrode using the thread interlocking machine of the invention, comprising the steps of: (a) inputting a desired architecture of an electrode to be fabricated; (b) optionally, compiling the desired electrode structure into interlocked digital structure and then into a machine code used to control the interlocking machine; (c) arranging a plurality of thread carriers at vertical tracks of segments of the thread interlocking machine according to the desired architecture; (d) selecting a carrier to function as a weft; (e) moving the weft along the horizontal track to pass between other filaments acting as the warps; (f) optionally, selecting a different thread carrier to function as a weft and switching therebetween; (g) continue moving the selected weft along the horizontal track to pass between the warps; (h) pressing the weft(s) towards the base to define a beat; and (i) terminating the process when the electrode is ready.

In certain embodiments, the method of the invention further comprises at least one of the following steps: (i) functionalizing at least a portion of the weft, e.g. by removing the coating material to expose the internal conductive material of the thread to create a contact; (ii) functionalizing at least a portion of the warp portions of the threads, e.g. by removing the coating material to expose the internal conductive material of the thread to create a contact; and (iii) terminating a thread when it is no longer needed in the electrode.

Figure 27:
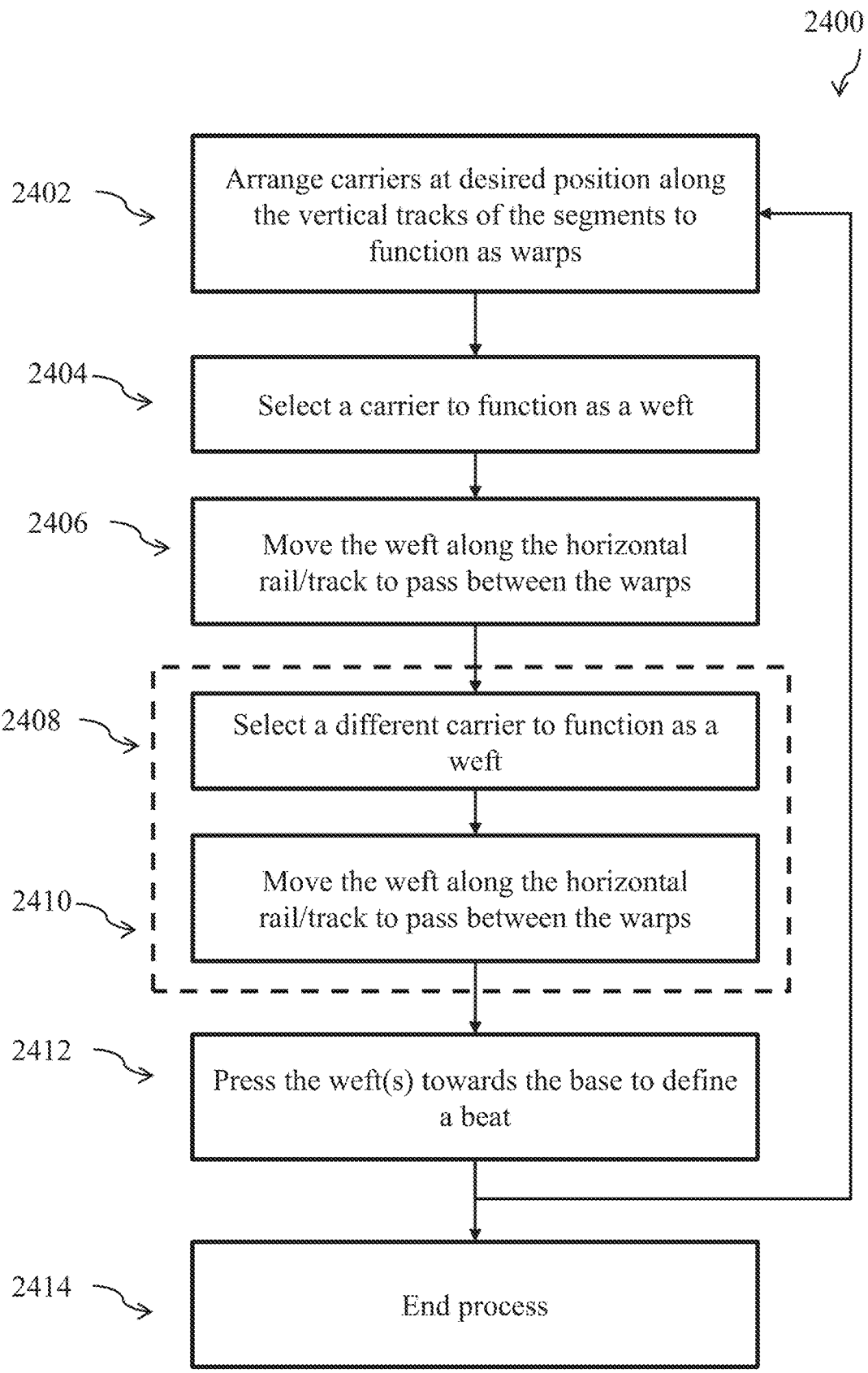
FIG. 27 schematically illustrates a method for thread interlocking, according to some embodiments.

FIG. 27 schematically illustrates a method for thread interlocking using the thread interlocking machine of the invention, the method comprising the steps of: arranging carriers, holding desired filaments at desired positions along the vertical tracks of the segments to function as warps 2402 according to a predefined architecture; selecting a carrier to function as a weft 2404; moving the weft along the horizontal rail/track to pass between the other filaments acting as the warps 2406; optionally, selecting a different carrier to function as a weft and switching therebetween 2408 in order to meet the desired structure outlined by the predefined architecture; continue moving the weft along the horizontal rail/track to pass between the warps 2410; pressing the weft(s) towards the base to define a beat 2412; and terminating the process when the electrode is ready 2414.

In other embodiments, the electrode architecture or cad design is inputted into a special compiler that compiles the electrode structure thus turning it into a digital form that describes the structure in threads, lengths, exposure places, materials deposition, interlocking form and any other mechanism and ability described in this invention. This compiler can find the properties of each desired contact, and then determine the thread exposure length needed in order to create the desired contacts by exposing thread/coated wire. For example, the total surface facing the tissue of the original contact could be determined: the compiler determines the length of a thread that is needed to be exposed in order to create a volume contact with the same or better exposed surface. The compiler also determines when the appropriate thread be used to form the contact, when functionalization would be activated over the same contact, which vertical or horizontal thread it will interlock with, and how the thread is to be folded in 3D to form the final volume contact. Alternatively or in addition, instead of surface area, the impedance of the original contact is calculated, followed by calculation of a comparable impedance of a volume contact, thereby extracting the exposure, folding and interlocking parameters. The compiler may further determine the interlocking structure flexibility, length, width, cross section, connection terminals that will be created by the interlocking machine.

In certain embodiments, the compiler, or a corresponding computing element receives data regarding the designated implantation destination, e.g. from a MRI, CAT or CT scans, and together with the desired treatment/parameters, determines the overall structure of the final electrode lead, including the type of threads that need to be used, the location of the contact areas, the functionalizing of each portion of the various threads, etc. This enables the easy and fast fabrication of customized electrode leads.

In another embodiment, another compiler is used to turn/compile the digital structure into machine code that controls the weaving process: once the interlocking machine is setup, the machine code will run sensing control signals to the interlocking mechanism, thus controlling the machine automatically or semi-automatically building desired interlocked leads as described in this invention.

Figure 28:
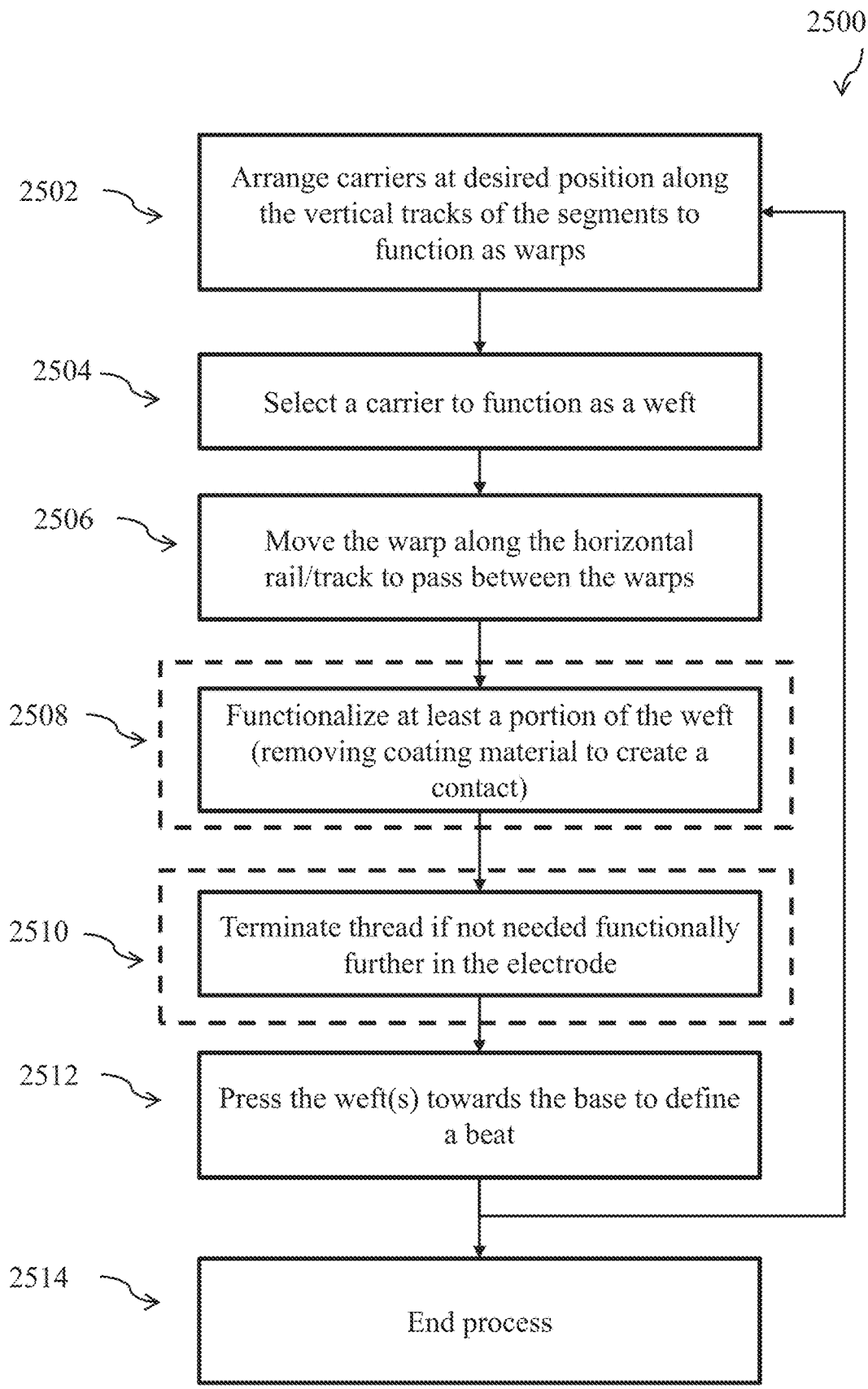
FIG. 28 schematically illustrates an additional method for thread interlocking, according to some embodiments.

FIG. 28 schematically illustrates yet another alternative method for thread interlocking using the thread interlocking machine of the invention, the method comprising the steps of: arranging carriers, holding desired filaments at desired positions along the vertical tracks of the segments to function as warps 2502 according to a predefined architecture; selecting a carrier to function as a weft 2504; moving the weft along the horizontal rail/track to pass between the other filaments acting as the warps 2506; optionally, functionalizing at least a portion of the weft, e.g. by removing the coating material to expose the internal conductive material and thus create a contact 2508; optionally, terminating a thread if it is no longer needed in the electrode 2510; optionally, selecting a different carrier to function as a weft and switching therebetween in order to meet the desired structure outlined by the predefined architecture; continue moving the weft along the horizontal rail/track to pass between the warps; pressing the weft(s) towards the base to define a beat 2512; and terminating the process when the electrode is complete 2514.

It should be noted that the thread interlocking method according to the invention by using the thread interlocking machine of the invention uses functionalization means, such as heat and laser systems for functioning each thread as it interlocked/weaved and prior to the final formation of the electrode—according to predefined electrode architecture. For instance, a laser may be used to expose the inner conductive core of a portion of a thread extending from a carrier that acts as a shuttle and wraps other threads at the fabricated electrode. Alternatively, the laser may be used to expose the inner conductive core of a portion of a thread extending from a carrier located at the surrounding segments that provide threads for the base of the fabricated electrode. Moreover, the laser can expose the inner conductive core of any portion of any thread-either the weft or the wrap, or both, all depending on the predefined electrode architecture. The exposure of the inner conductive core or the various threads enables the formation of an electrical contact area at the precise desired point having desired shape and electrical properties obtained by the shape and depth of the fabricated contact area (e.g. conductivity, electric field, etc.).

In certain embodiments of the method of fabricating an interlocked electrode lead according to the invention, the setup of the thread interlocking machine, including placing and adjusting the carriers, threads, and materials therewithin, is done only once—prior to activation of the machine. Alternatively, it is done when there is a need to replace/recharge the threads as needed, e.g. when a different type of thread is needed, or when a thread is torn or ends.

Accordingly, in certain embodiments, the method of fabricating an interlocked electrode lead according to the invention, enables the fabrication of multiple electrodes without stopping the machine. This is due to the ability of the interlocking machine of the invention to customize the electrode lead as it is being build, and its ability to cut each electrode once it is done, therefore clearing the way for the fabrication of the next electrode. In specific embodiments, the method is for fabricating a plurality of identical electrodes. In other specific embodiments, the method is for fabricating a plurality of different electrodes. In both cases, without the need to stop the machine for adjustments or modifications.

Additional inventive concepts of the present invention include:

A—Volumetric contact: an electrode with at least one contact, the contact having a "conductive volume-space", which may either protrude/project/extend from the electrode, be formed within the electrode as a cavity/hollow/chamber/pocket therein, or a combination thereof.

B— Volume sharing: having more than one contact placed within the same volume, having a shared volume to more than one contact, or a plurality of contacts being at least partially spatially-interleaved in the same space/volume.

C— Contact placement: determining the place/distance from a reference point based on the thread count, wherein the spacing between threads/beats/weaving—patterns is predetermined/known.

D—deposition of material: deposition of a support/isolation threads/material within the electrode during the forming/fabrication/printing/weaving process, and treating/transforming the deposited threads/material to form a medium having a desired purpose/function after the forming/fabrication/printing/weaving process.

The present invention further provides the following structural elements:

Volumetric Contact:

A device (electrode) comprising a volumetric-contact occupying a predetermined volume, the volumetric-contact having a porous structure with multiple conductive surfaces therein, for facilitating a delivery of an electric signal to/from a fluid environment via the multiple conductive surfaces within the volume of the volumetric-contact:
  The conductive surfaces of the volumetric-contact, having a cumulative conductive surface area larger than a cross-section area of the volumetric-contact.
  The volumetric-contact being formed/integrated within the electrode body/housing, within/forming a cavity/hollow therein.
  The volumetric-contact protruding from the surface of the electrode body/housing, forming a protrusion/bump of porous structure.
  The volumetric-contact having a protruding portion and an internal portion.
  The porous structure and conductive surfaces being made of various materials and combinations.
  The volumetric-contact being shaped as any desirable possible shape.
  Different capacitive charge values per volume.
  The electrode having multiple volumetric-contacts.
A system comprising the electrode as described above, with a stimulation signal generator and/or a signal reader/interpreter:

Volume Sharing:

An electrode with a first contact having a structure occupying a defined space (surface or volume) to form conductive surfaces with a plurality of voids therein, and a second contact with at least one conductive surface, being at least partially interleaved with the first contact to occupy at least one of the plurality of voids within the structure of the first contact, such that there is no direct electric contact between the at least one conductive surface of the second contact and the plurality of contact surfaces of the first contact:
  The second electrode having a structure occupying a defied space form conductive surfaces with a plurality of voids therein, such that at least some of the conductive surfaces of the first contact are positioned within at least some of the voids of the structure of the second electrode, and at least some of the conductive surfaces of the second contact are positioned within at least some of the voids of the structure of the first contact.
  The first contact and/or the second contact occupying a space defining a volume/space/line/spot/dot.
  The second contact being fully interleaved with the first contact
  The second contact and the first contact having an interleaved/shared space, and each having an independent space not interleaved with the other electrode structure.
  At least one of the contacts being a stimulation contact, and one of the contacts being a recording contact.
  Multiple interleaved contacts arrange to form an interleaved contact cascade.
  Structures of the interleaved contacts.
  Materials of the structures.
A system comprising the electrode as described above, with a stimulation signal generator and/or a signal reader/interpreter.
  The system being configured to select between interleaved contacts for directionality modification.
  The system being configured to intermittently select between interleaved stimulation contact and recording contact.
A method of using a device/system as described above
  To select between interleaved contacts for directionality modification.
  To intermittently select between interleaved stimulation contact and recording contact.

Contact Placement:

An electrode having on the surface thereof multiple guiding-marks having a predetermined/known spacing therebetween, and configured to facilitate measuring a distance from a reference point on the electrode:
  The multiple guiding-marks being threads/thread-beats/weaving patterns of the material forming the electrode.
  A weaving structure, and how the distance is measured.
  Alternative structures and measuring options.
  Performing a function based on the measured distance: placing an electrode, exposing a contact, deploying masking material.
A method for measuring the distance from a reference point on electrode using multiple guiding-marks on the surface of the electrode:
  The method being applying during the formation of certain layers within the electrode
  The method being applying during weaving Deposition of Material:

A method for fabricating/constructing/making/manufacturing an electrode that includes deposition of materials at predetermined location within the electrode structure and at predetermined times during the manufacturing process, and treating/transforming the deposited materials at a later stage to form a medium for achieving a desired property/function:

The deposited material comprising threads.

The desired property/function being robustness.

The desired function being isolation between at least two contacts.

The desired function being erection of the electrode structure.

The desired function being masking for further manufacturing steps.

The desired function being patterning within the electrode.

The deposition of the material being integrated with a weaving process of making the electrode.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising," when used in this specification, specify the presence of stated features, integers, steps, operations, elements, or components, but do not preclude or rule out the presence or addition of one or more other features, integers, steps, operations, elements, components, or groups thereof.

What is claimed is:

1. A medical thread structure, comprising:
a longitudinal lead body formed of a plurality of threads, at least one of said plurality of threads has an electrically conductive portion, said longitudinal lead body is arranged along a longitudinal axis;
a functional material at least partially incorporated between said plurality of threads and at least partially located circumferentially around at least a portion of said longitudinal lead body at a certain location along the longitudinal extent of said longitudinal lead body, wherein said functional material is configured to form insulation areas within said longitudinal lead body, and wherein said functional material is configured to insulate said at least portion of said longitudinal lead body upon application of heat onto said longitudinal lead body, thus causing melting of said functional material into a single continuous structure, and wherein said longitudinal lead body has:
a. a proximal end and a distal end, and
b. said plurality of threads being aligned vertically, in parallel to the longitudinal axis, at said proximal end, wherein at least a portion of said plurality of threads is structured to have horizontal portions, perpendicular to the longitudinal axis, and vertical portions, parallel to the longitudinal axis, such that a horizontal portion of one thread is configured to pass between vertical portions of other threads, thereby interlocking therewith, wherein a horizontal portion of one or more threads passing between vertical portions of other threads is a beat, and each beat determines a vertical distance along the longitudinal axis between said proximal end and said distal end;
and wherein at least one electrically conductive portion of at least one of said plurality of threads is coated with an electrically isolative layer and wherein at least one of said electrically conductive portions of at least one of said plurality of threads is exposed at predetermined locations for achieving a contact thereat.

2. The medical thread structure of claim 1, wherein a vertical portion of a thread is a warp portion, and a horizontal portion of a thread is a weft portion, and at least some of the threads are configured to be warps at certain locations, and wefts at other locations.

3. The medical thread structure of claim 2, wherein when threads pass from being warp to being weft they form a directional contact; during weft portions of threads the one weft beat can: (i) form a full circle and wrap around an entire fabricated interlocked lead or lead core; or (ii) does not form a full circle and does not wrap around the entire fabricated interlocked lead or lead core, but rather wrap only a portion of the warp(s) at a specific area of a fabricated electrode.

4. The medical thread structure of claim 2, wherein the plurality of threads are arranged to form an elongated shape, such that the axis of the elongated shape is the longitudinal axis between said proximal-end and said distal-end, and a horizontal cross-section thereof comprises a plurality of vertical thread portions arranged at various radial distances and wherein said vertical thread portions are configured to be formed by weaving or braiding.

5. The medical thread structure of claim 1, wherein horizontal portions of a plurality of threads pass through vertical portion of at least one other thread to form one beat.

6. The medical thread structure of claim 1, wherein the plurality of threads are arranged to form an elongated cylindrical shape, such that the axis of the elongated cylindrical shape is the longitudinal axis between said proximal end and said distal end.

7. The medical thread structure of claim 1, wherein said electrically conductive portion of said at least one thread is exposed at predetermined locations in horizontal portions, forming a two-dimensional contact at said predetermined locations.

8. The medical thread structure of claim 1, wherein a horizontal portion of at least one thread at a plurality of beats forms a three-dimensional structure along and within the medical thread structure.

9. The medical thread structure of claim 1, wherein said electrically conductive portion of said at least one thread is exposed at predetermined locations in horizontal portions, forming a three-dimensional contact.

10. The medical thread structure of claim 1 and wherein said functional material being integrally incorporated between at least part of said plurality of threads; and wherein said functional material is configured to form insulation areas in said medical thread structure.

11. The medical thread structure of claim 1 wherein said incorporation of said functional material comprises interlocking of said functional material between said plurality of threads.

* * * * *